(12) United States Patent
Huang et al.

(10) Patent No.: US 8,071,388 B2
(45) Date of Patent: *Dec. 6, 2011

(54) COMPOSITIONS AND METHODS FOR BIODETECTION BY NUCLEIC ACID-TEMPLATED CHEMISTRY

(75) Inventors: Yumei Huang, North Billerica, MA (US); James M. Coull, Westford, MA (US)

(73) Assignee: Ensemble Therapeutics Corporation, Cambridge, MA (US)

(*) Notice: Subject to any disclaimer, the term of this patent is extended or adjusted under 35 U.S.C. 154(b) by 21 days.

This patent is subject to a terminal disclaimer.

(21) Appl. No.: 12/391,898

(22) Filed: Feb. 24, 2009

(65) Prior Publication Data

US 2009/0275142 A1    Nov. 5, 2009

Related U.S. Application Data

(63) Continuation-in-part of application No. PCT/US2007/021094, filed on Sep. 28, 2007, and a continuation-in-part of application No. PCT/US2007/020223, filed on Sep. 18, 2007.

(60) Provisional application No. 60/905,364, filed on Mar. 7, 2007, provisional application No. 60/918,023, filed on Mar. 14, 2007, provisional application No. 60/847,859, filed on Sep. 28, 2006.

(51) Int. Cl.
*G01N 33/68* (2006.01)
*G01N 33/00* (2006.01)
*C07D 209/04* (2006.01)
*C07D 207/46* (2006.01)
*C07D 209/56* (2006.01)
*C07H 21/04* (2006.01)
*C07C 229/40* (2006.01)

(52) U.S. Cl. ............ 436/86; 436/96; 436/94; 536/23.1; 548/510; 548/467; 548/544; 548/427; 562/433

(58) Field of Classification Search .................. 548/510, 548/467, 544, 427
See application file for complete search history.

(56) References Cited

U.S. PATENT DOCUMENTS

| | | | |
|---|---|---|---|
| 2,398,999 | A | 4/1946 | Brooker et al. |
| 3,987,037 | A | 10/1976 | Bonham et al. |
| 6,890,741 | B2 | 5/2005 | Fan et al. |
| 7,070,928 | B2 | 7/2006 | Liu et al. |
| 7,223,545 | B2 | 5/2007 | Liu et al. |
| 7,442,160 | B2 | 10/2008 | Liu et al. |
| 7,491,494 | B2 | 2/2009 | Liu et al. |
| 7,557,068 | B2 | 7/2009 | Liu et al. |
| 7,771,935 | B2 | 8/2010 | Liu et al. |
| 2004/0180412 | A1 | 9/2004 | Liu et al. |
| 2005/0233381 | A1 | 10/2005 | Liu et al. |
| 2006/0223086 | A1 | 10/2006 | Liu et al. |
| 2007/0154899 | A1* | 7/2007 | Coull et al. ............... 435/6 |
| 2009/0280477 | A1 | 11/2009 | Coull et al. |
| 2010/0159446 | A1 | 6/2010 | Haff et al. |
| 2010/0159455 | A1 | 6/2010 | Landsman et al. |
| 2011/0059458 | A1 | 3/2011 | Huang et al. |

FOREIGN PATENT DOCUMENTS

| | | |
|---|---|---|
| EP | 0383092 | 8/1990 |
| EP | 0632102 | 1/1995 |
| EP | 1 423 400 A2 | 6/2004 |
| GB | 1229429 | 4/1971 |
| GB | 1480133 | 7/1977 |
| WO | WO-02057479 A2 | 7/2002 |
| WO | WO-2006/128138 A2 | 11/2006 |
| WO | WO 2006128138 A2 * | 11/2006 |
| WO | WO-2007008276 | 1/2007 |
| WO | WO-2008/036273 A2 | 3/2008 |

OTHER PUBLICATIONS

Brady et al., *J. Bio. Chem.* 2001, 276:18812-18818.
Bratenko et al., *Chemistry of Heterocyclic Compounds* 2004, 40:1279-1282.
Capaldi et al., *Nucleic Acid Res.* 2000, 28(7):e21.
Castiglioni et al., *Appl. Environ. Microbio.* 2004, 70(12):7161-72.
Doyon et al., *J. Am. Chem. Soc*, 2003, 125:12372-12373 and supporting online material, 8 pages.
Eitel et al., *Synthesis* 1989, 364-367.
Fang et al., *Chem.BioChem.* 2003, 4:829-34.
Gartner et al., 2004, *Science*, 305:1601-1605 and supporting online material, 10 pages.
Gerry et al., *J. Mol. Biol.* 1999, 292:251-62.
Green et al., *Biochemistry* 1996, 35:14413-24.
Hunsberger et al., *J. Org. Chem.* 1956, 21:394-399.
Jedrzejewska et al., *Dyes and Pigments* 2003, 58:47-58.
Kobayashi, et al., *J. Am. Chem. Soc.* 1998, 120:8287-8288.
Li et al., *Angew. Chem. Int. Ed.* 2004, 43:4848-4870.
Lindsey et al., *Tetrahedron* 1989, 45:4845-4866.
Lipsky et al., *Clinical Chemistry* 2001, 47(4):635-44.
Mase et al., *J. Am. Chem. Soc.* 2006, 128:734-735.
McIntosh et al., *Electrophoresis*, 2002, 23:1473-1479.
Sakurai et al., *J. Amer. Chem. Soc.*, 2005, 127:1660-1667 and supporting online material, 12 pages.
Thevenin et al., *Eur. J. Biochem* 1992, 206:471-477.
Wetmur, *Criti. Rev. in Biochem. And Mol. Biol.*, 1991, 26:227-259.
International Search Report for International Application No. PCT/US2007/021094, mailed Feb. 11, 2009, 4 pages.
Written Opinion for International Application No. PCT/US2007/021094, mailed Feb. 11, 2009, 6 pages.

\* cited by examiner

*Primary Examiner* — Yong Chu
(74) *Attorney, Agent, or Firm* — Goodwin Procter LLP

(57) ABSTRACT

The invention provides compositions and methods for the detection of biological targets, (e.g. nucleic acids and proteins) by nucleic acid-templated chemistry, for example, by generating fluorescent polymethine dyes.

13 Claims, 50 Drawing Sheets

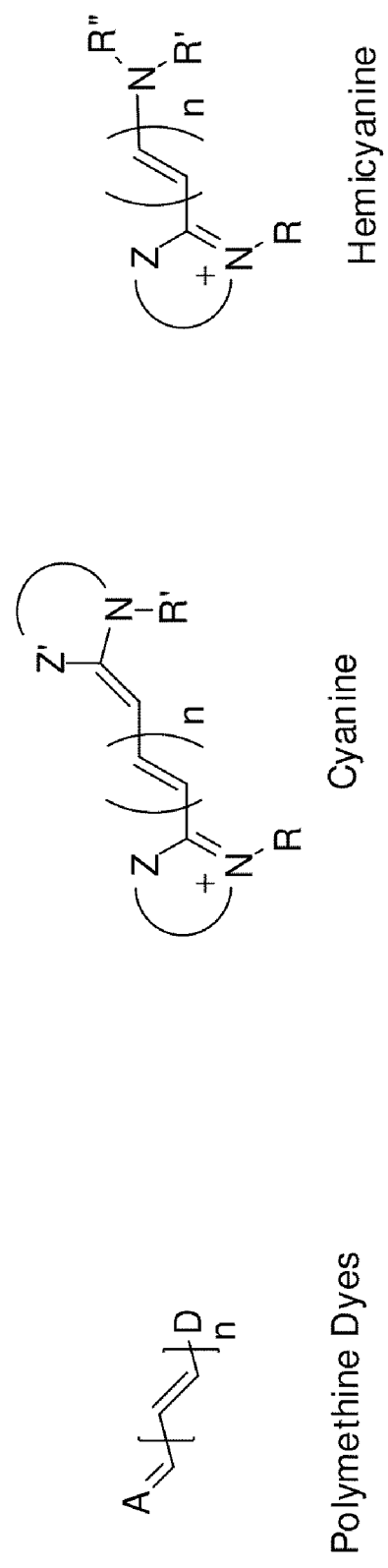
FIG. 1: General structure of polymethine dye, cyanine and hemicyanine

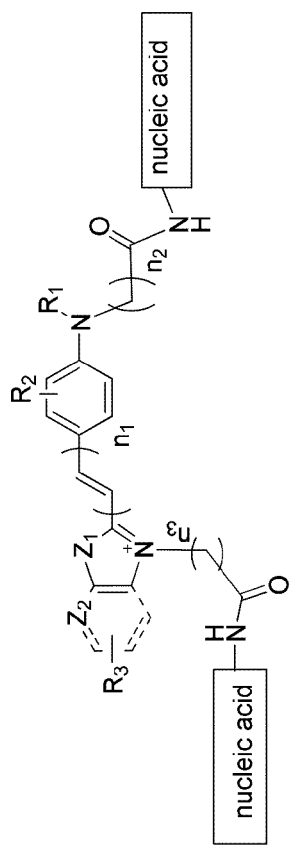
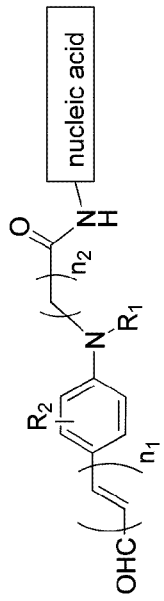
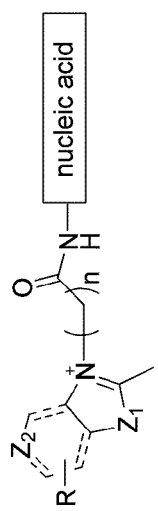
FIG. 2: General chemical structures of hemicyanine dyes useful for multiplex and their aldehyde and quaternary salt precursors.

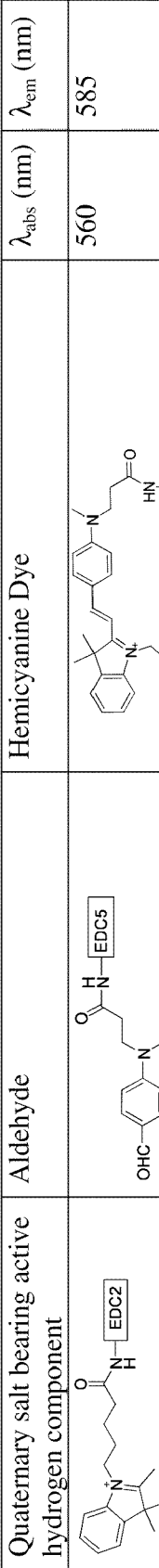
FIG. 3: Chemical structures of a four-plex hemicyanine_DNA dyes and their spectroscopic properties.

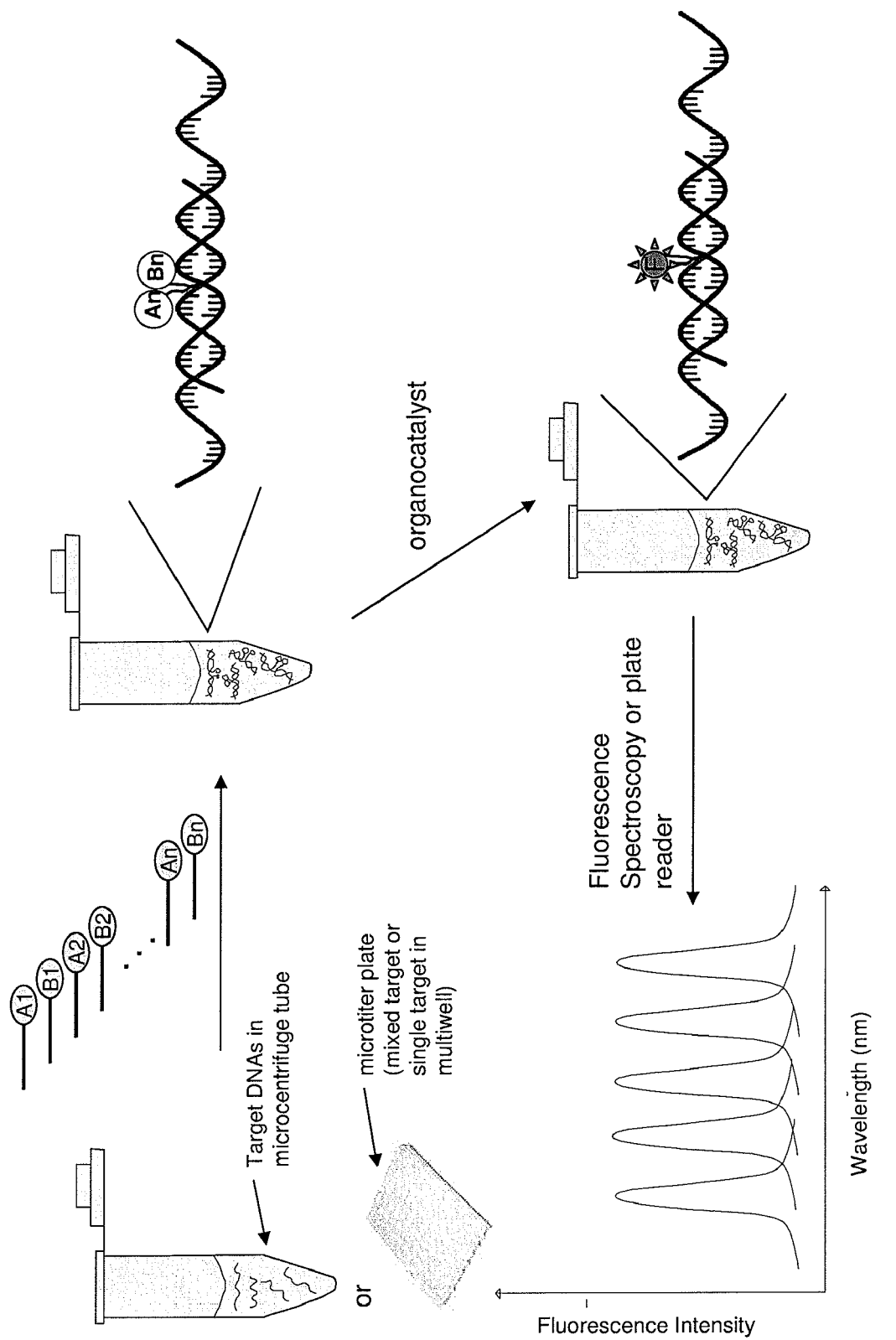
FIG. 4: Solution phase based DPC fluorescence assay for multiple analytes

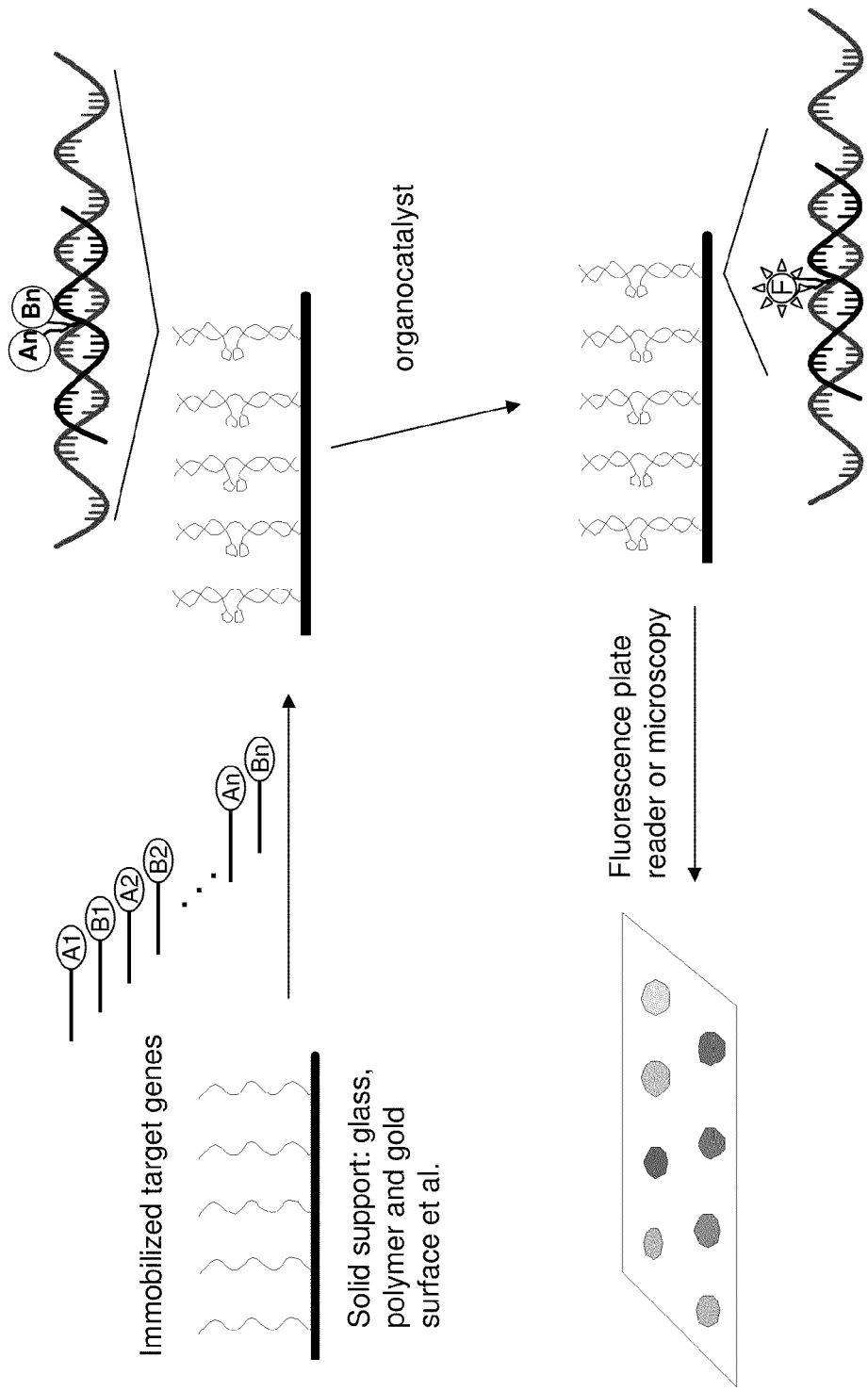
FIG. 5: Solid phase based DPC fluorescence assay for multiple analytes

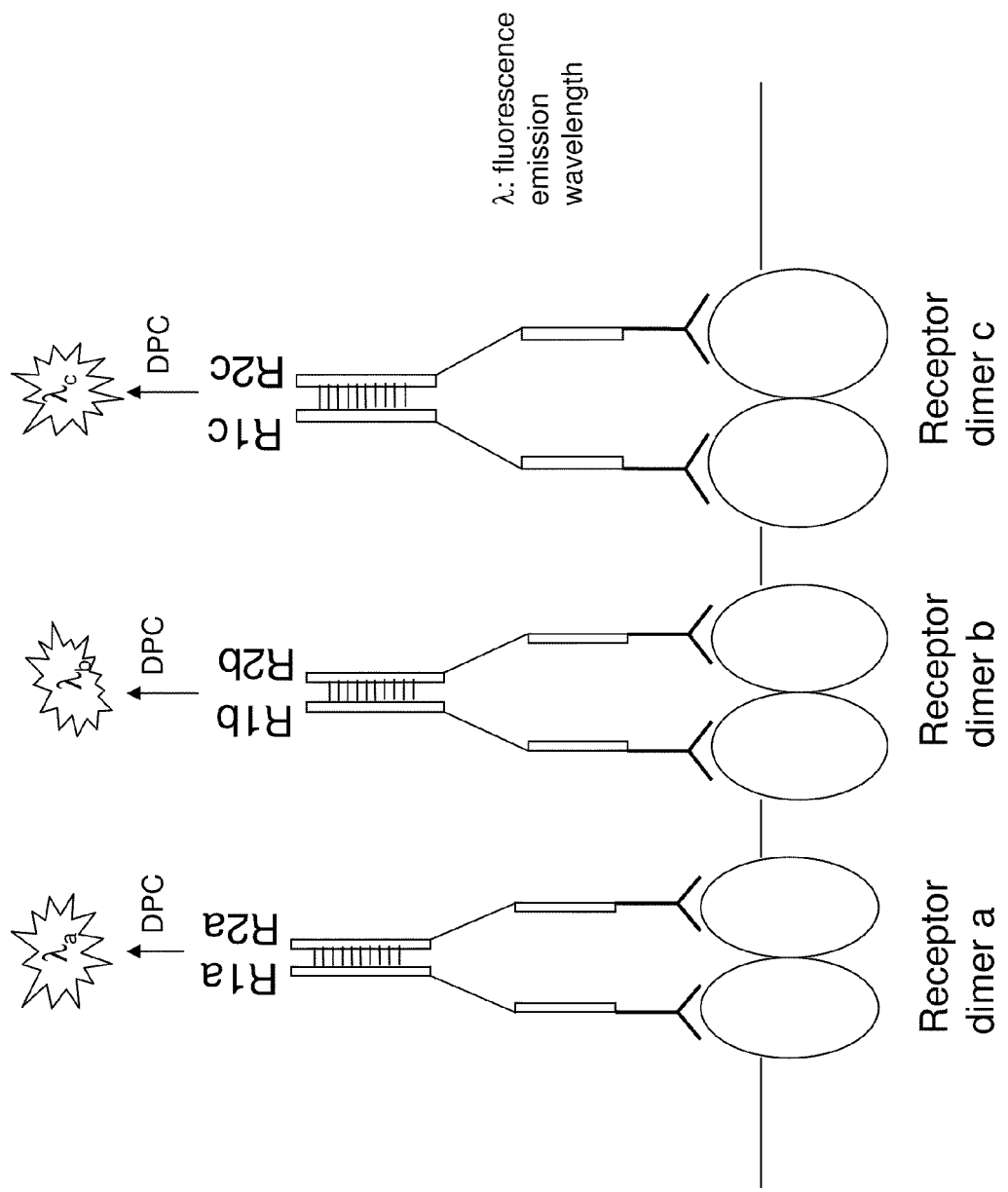
FIG. 6: Multiplexed IHC test for multiple family receptors dimer (non-zip-coded).

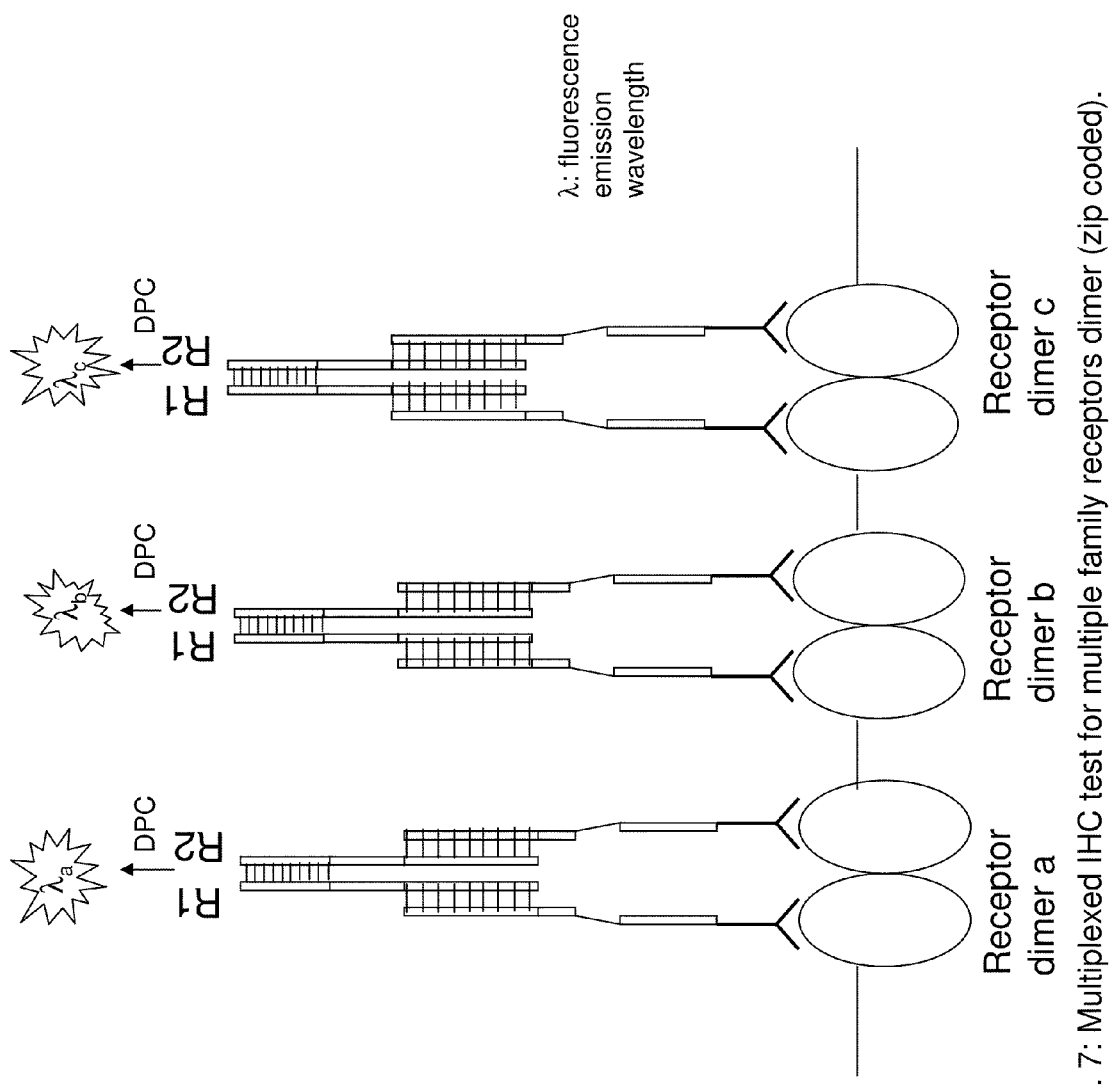
FIG. 7: Multiplexed IHC test for multiple family receptors dimer (zip coded).

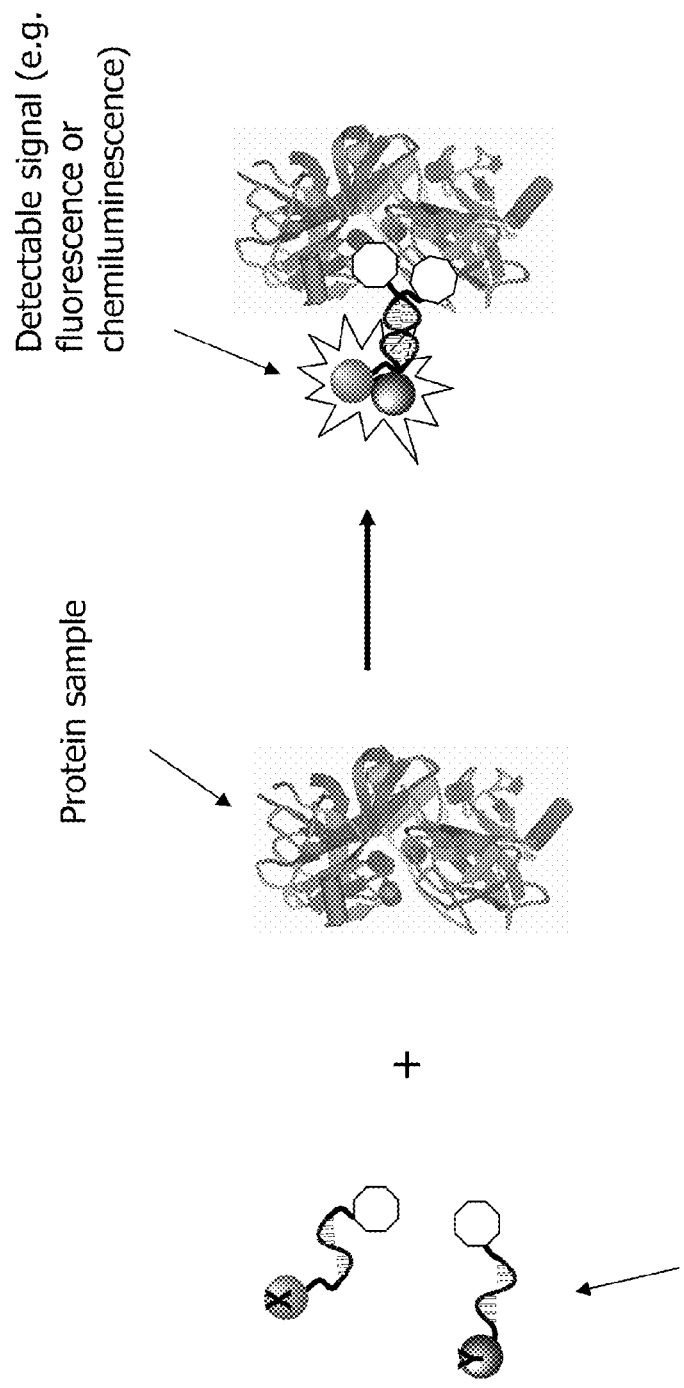

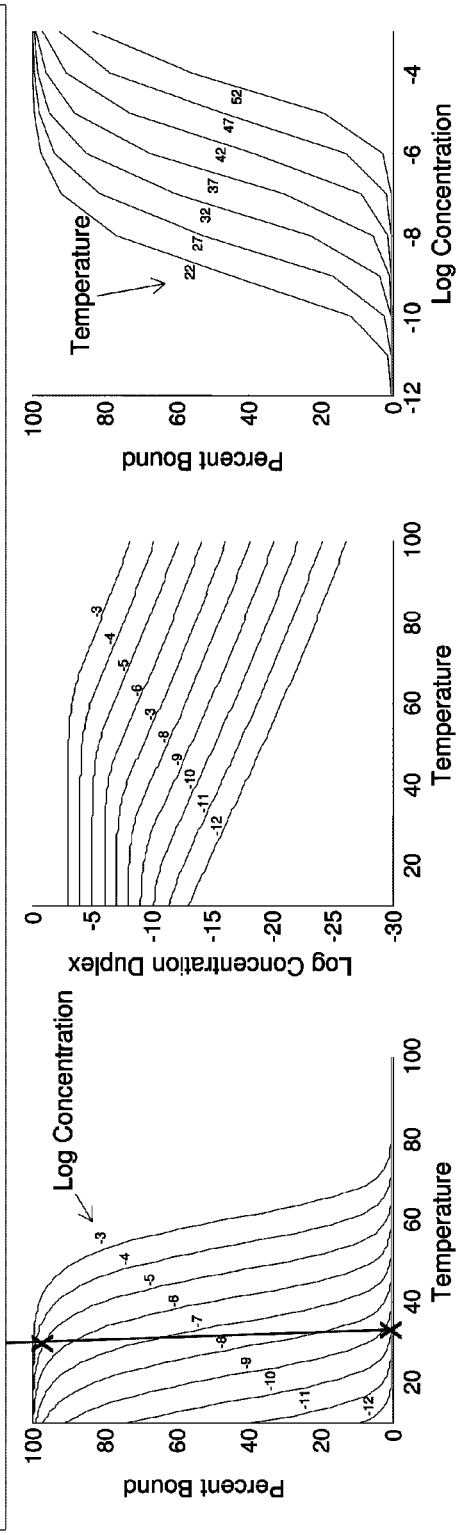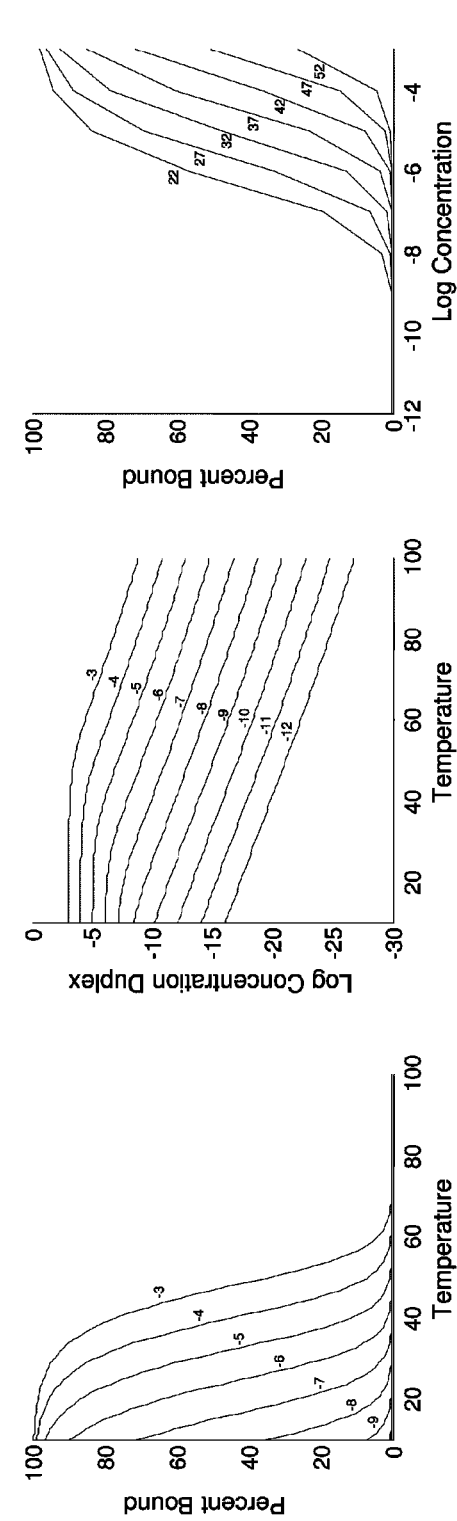
FIG. 10

FIG. 11

Oligos Used to Construct Melting Curves

Perfect Match:

5' (+) CAATGGATGTACTTCTTC (SEQ ID NO: 5)
        ||||||||||
(-) CTTCTTCAGTTACCTACA 5' (SEQ ID NO: 6)

Single Mismatch:

5' (+) CAATGGATGTACTTCTTC (SEQ ID NO: 7)
        ||| |||||
(-) CTTCTTCAGTTTCCTACA 5' (SEQ ID NO: 8)

- Illustrative exemplary of a Zip-Coded Splinted Architecture
- NNN... represents zip code sequence, and N'N'N'... represent complement of the zip code sequence (anti-zip codes)

FIG. 14

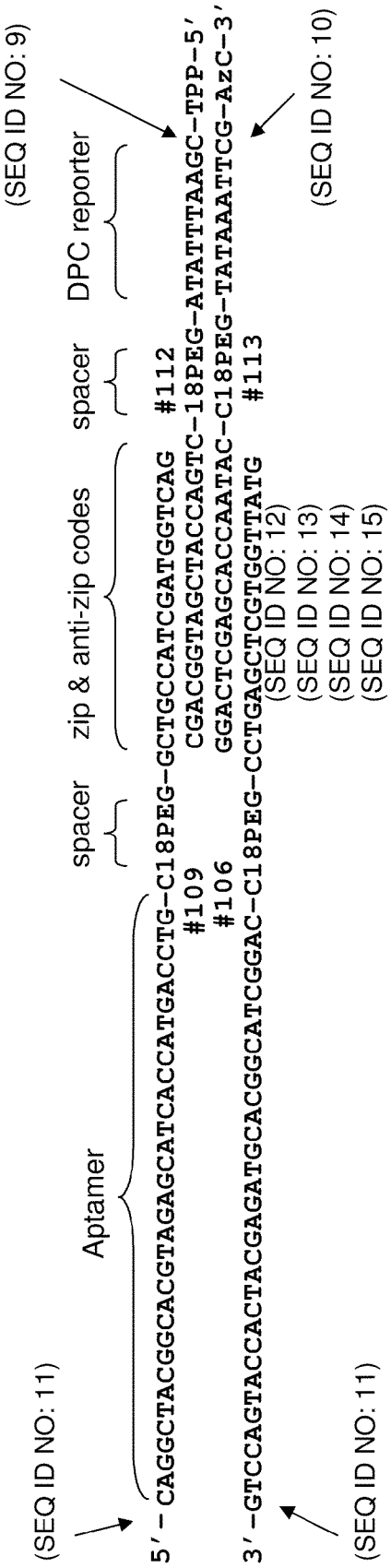

Example of splinted, zip-coded detection probes using aptamer binders

- The upper and lower two oligonucleotides include aptamer sequence linked to separate zip code sequences with a C18 PEG spacer.

- The inner two oligonucleotides (reporter oligonucleotides) include anti-zip codes (sequences each complementary to a zip code in one of the upper and lower oligoncleotides) linked through a C18 PEG spacer to a reporter oligonucleotide.

- One reporter oligonucleotide contains a 5'-terminal TPP residue, the other a 3' terminal AzC residue. Each zip code is complementary only to its anti-zip code.

- The reporter sequences are complementary only to each other.

FIG. 15

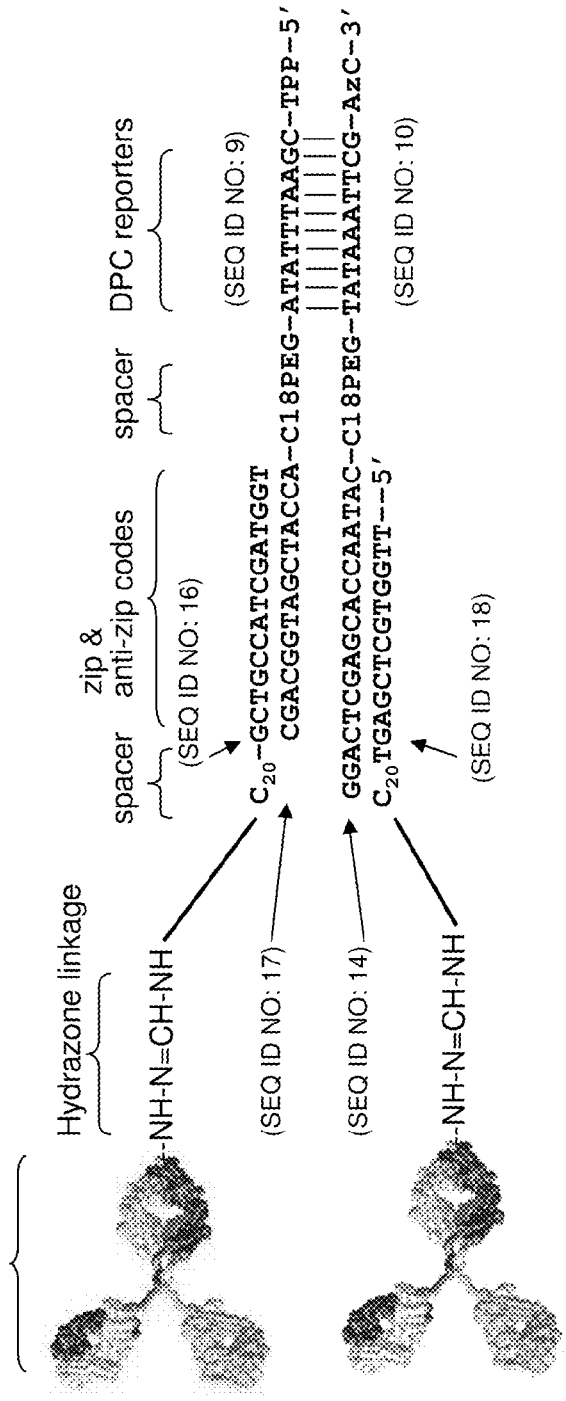

Example of splinted, zip-coded detection probes using antibodies

- Anti-PDGF-BB antibody covalently labeled via hydrazone linkages to a 15-base zip code sequence with a 20-base spacer of cytosine (C20).
- TPP reporter oligonucleotide with a complementary 15-base anti-zip code sequence linked via a C18 PEG spacer to a 10-base reporter sequence.
- AzC reporter oligonucleotide with an anti-zip code sequence and a 10-base reporter sequence complementary to the TPP reporter sequence. Anti-zip code sequence was 20 bases long, with 15 bases complementary to the zip code sequence.

FIG. 16

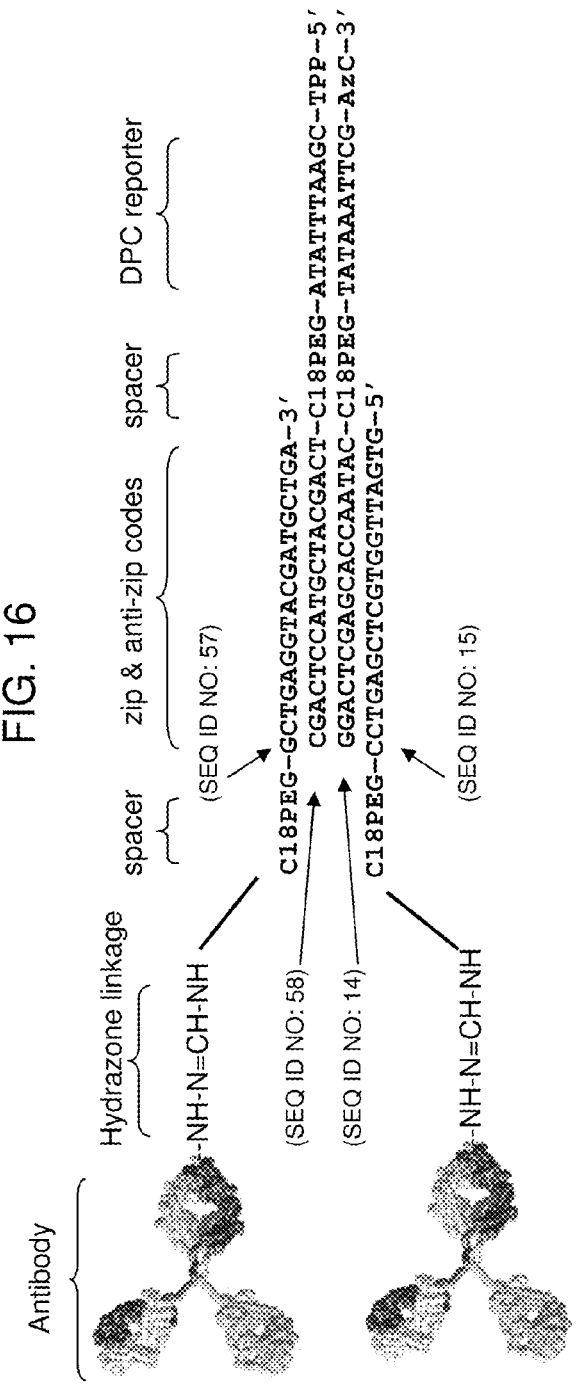

Exemplary assembly of Antibody-linked, zip-coded Detection Conjugates.

• Primary amino groups in the antibodies are activated to hydrazines and reacted with 3' and 5'-aldehyde-containing oligonucleotides to form hydrazone linkages.

• The upper and lower two oligonucleotides linked to the antibodies also contain separate zip code sequences separated from the antibody by a C18 spacer arm.

• The inner two oligonucleotides (reporter oligonucleotides) consist of anti-zip code sequences linked through a C18 PEG spacer to a reporter oligonucleotide.

• One reporter oligonucleotide contains a 5'-terminal TPP residue, the other a 3' terminal AzC residue. Each zip code is complementary only to its anti-zip code, and the DPC reporter sequences are complementary only to each other.

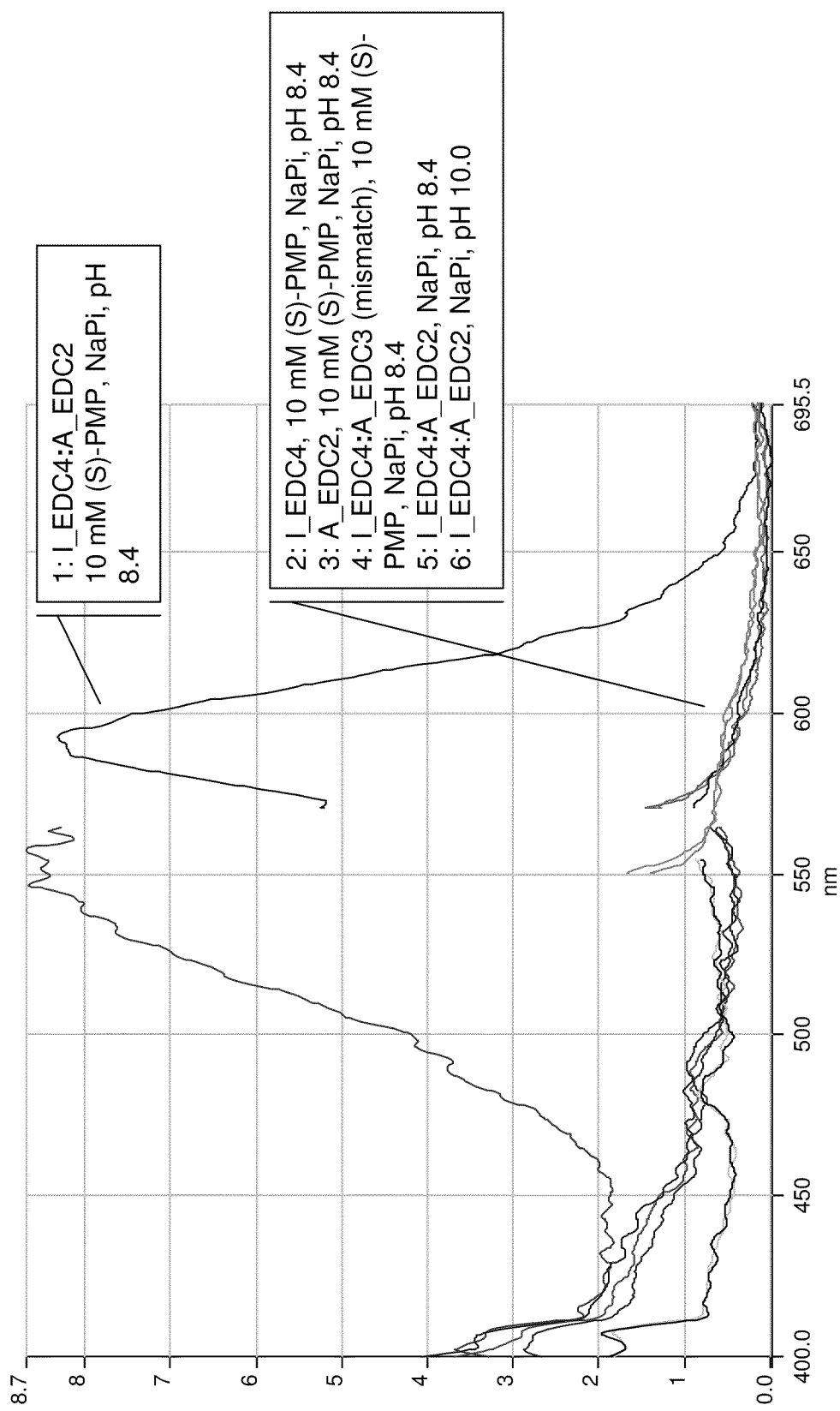
FIG. 17 Absorption and fluorescence emission spectra of DPC reaction mixtures (end of helix) after 2.3 hr at RT (200 nM each ssDNA, 1 M NaCl)

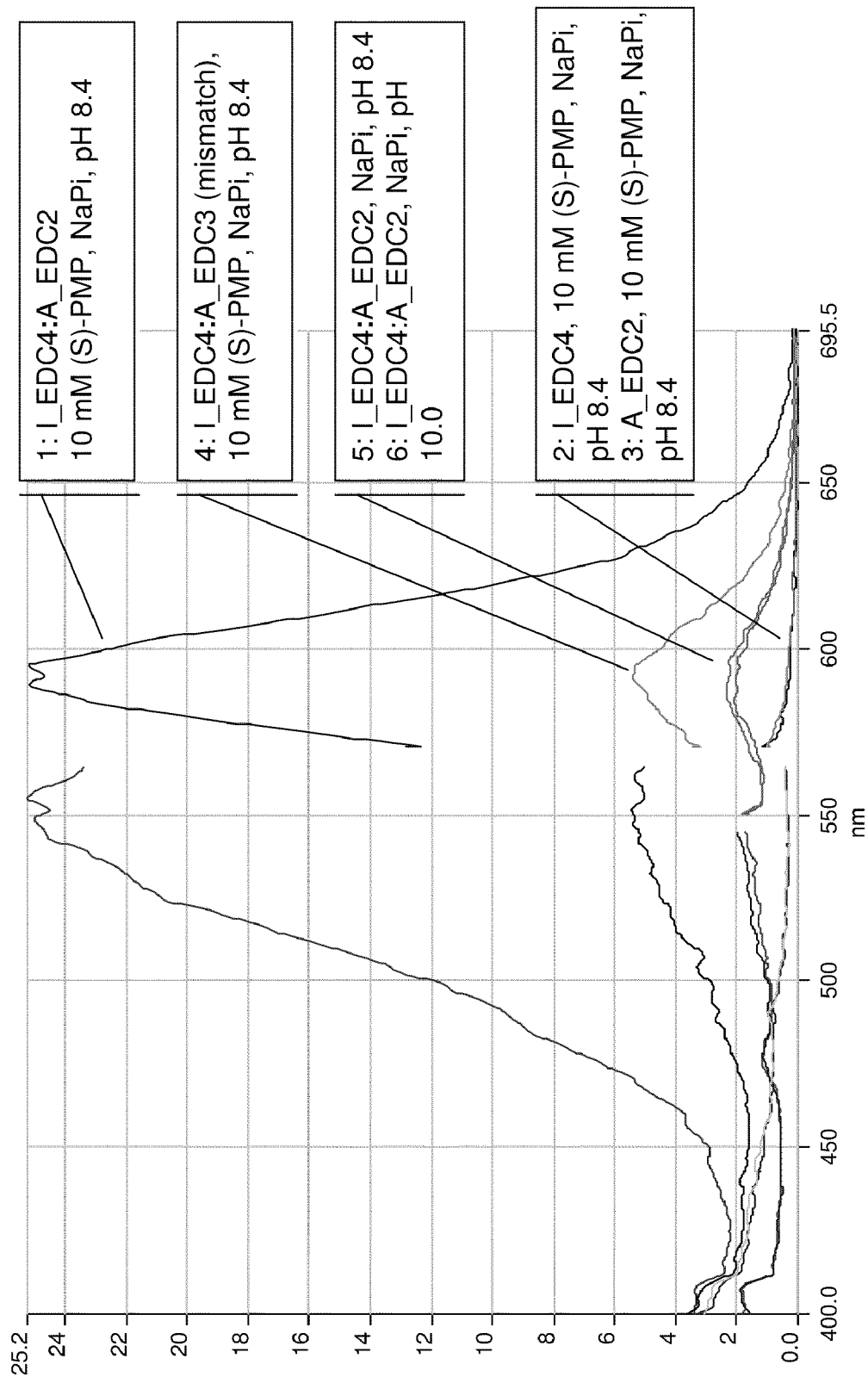
FIG. 18 Absorption and fluorescence emission spectra of DPC reaction mixtures (end of helix) after 16 hr at RT (200 nM each ssDNA, 1 M NaCl)

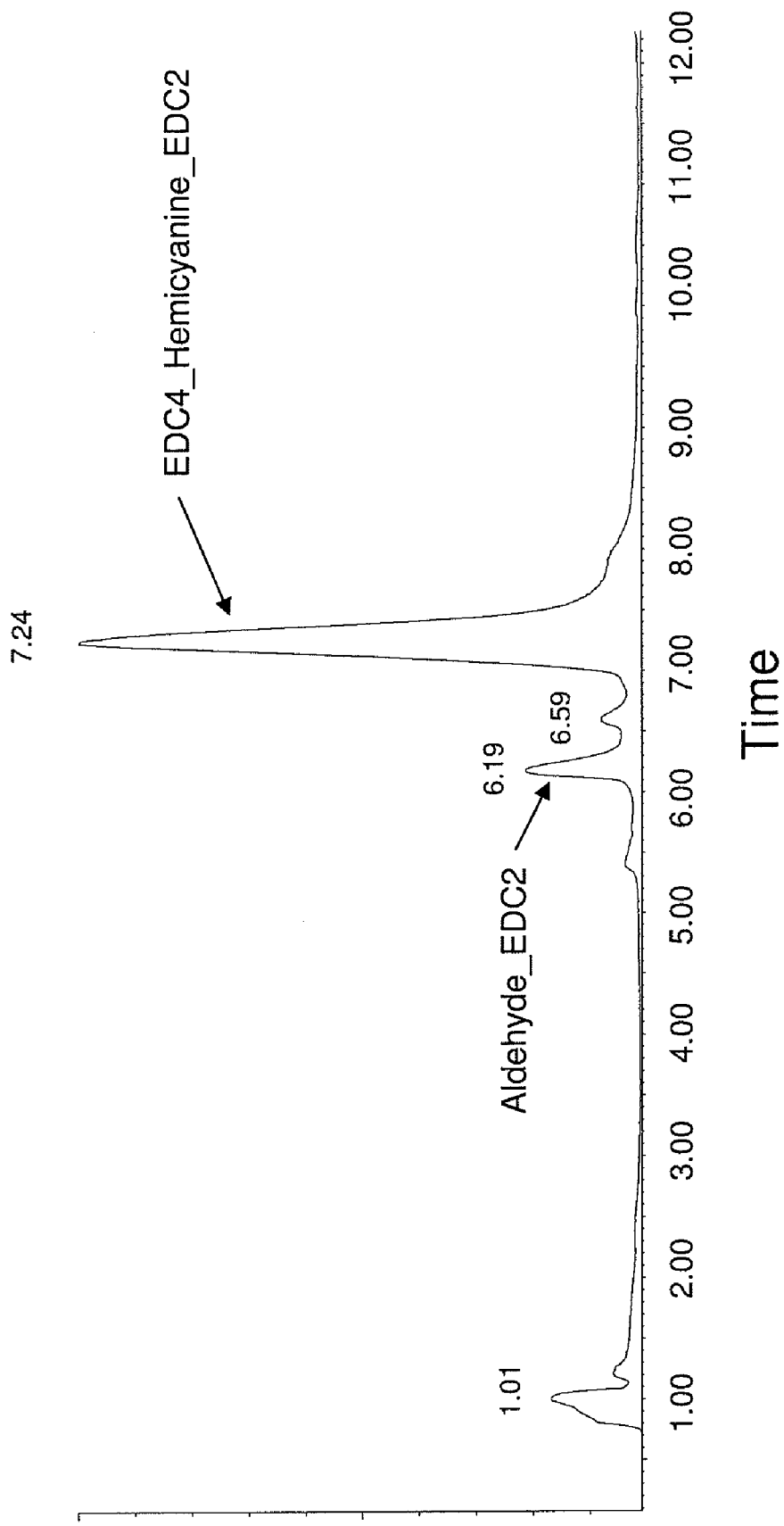
FIG. 19 LC-MS analysis of crude DPC reaction mixture of indolinium_EDC4:aldehyde_EDC2 after 16 hr at RT.

LC-MS ANALYSIS OF PURIFIED DPC PRODUCT EDC4_HEMICYANINE_EDC2.

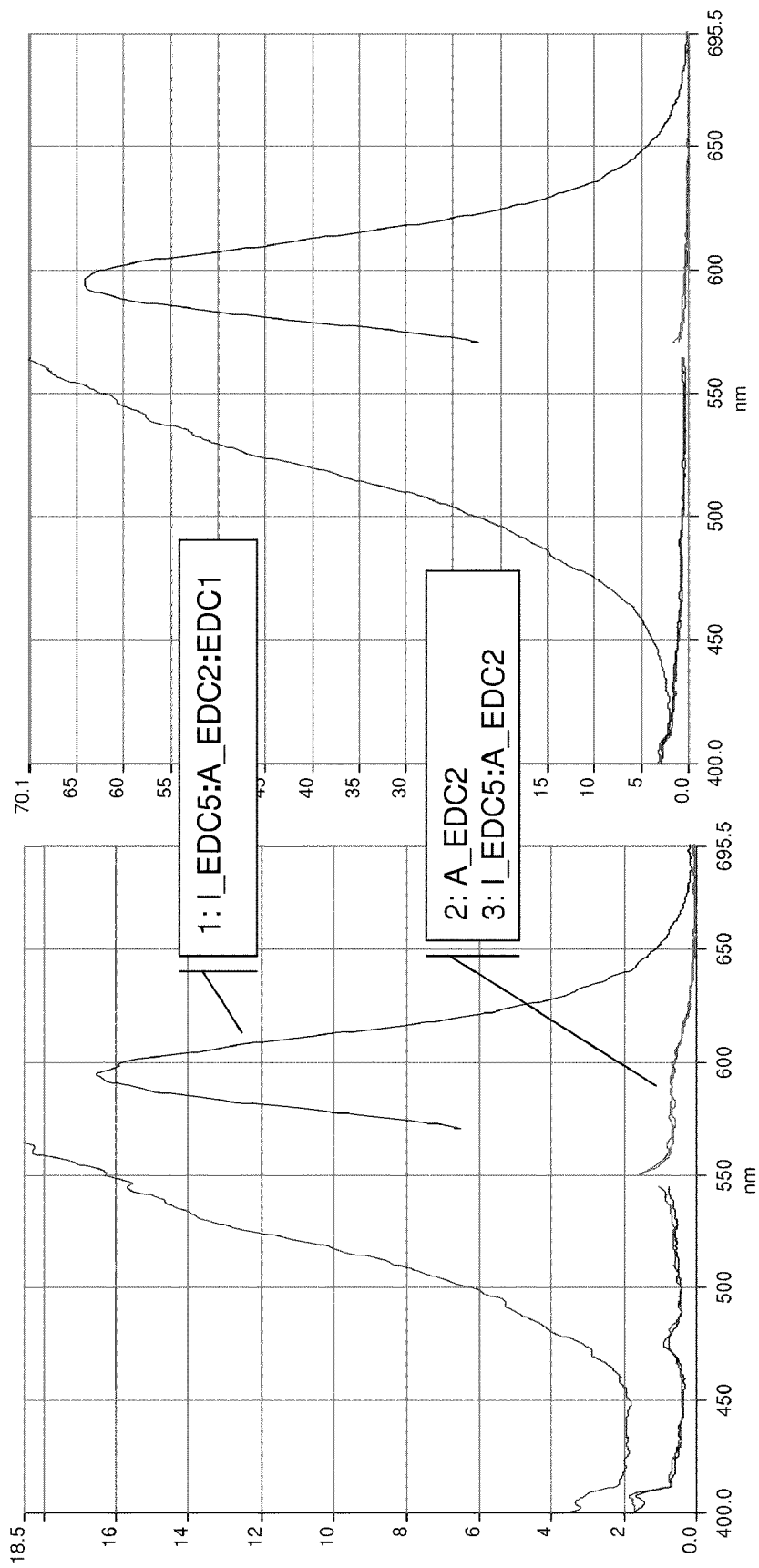
FIG. 21 Absorption and fluorescence emission spectra of DPC reaction mixtures (middle of helix) after 2.3 hr (left) and 16 hr (right) at RT (200 nM each ssDNA, 1 M NaCl, 50 mM NaPi, pH 8.4, 10 mM (S)-PMP)

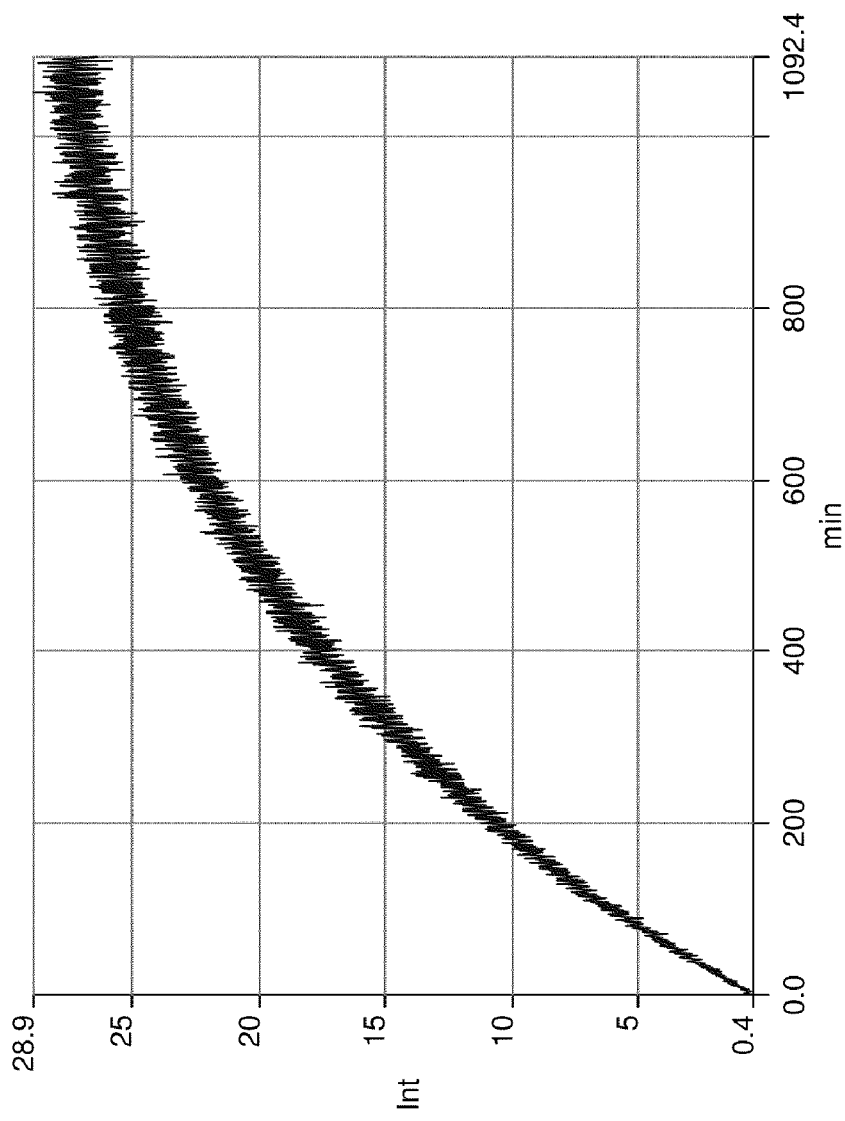
FIG. 23 Plot of fluorescence intensity at 590 nm vs time for DPC of Indolinium_EDC4 and Aldehyde_EDC2 (Excitation at 550 nm)

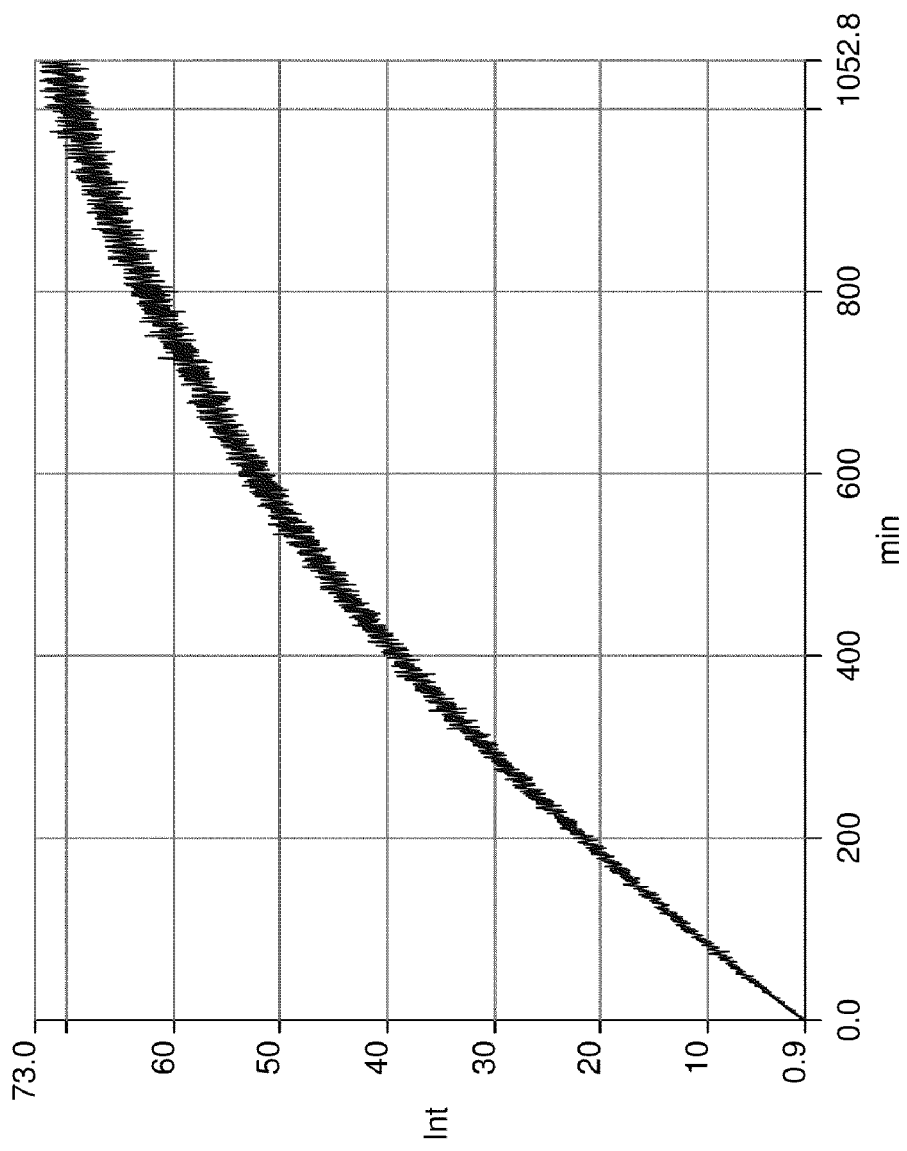
FIG. 24 Plot of fluorescence intensity at 590 nm vs time for DPC of Indolinium_EDC5, EDC1 and Aldehyde_EDC2 (Excitation at 550 nm).

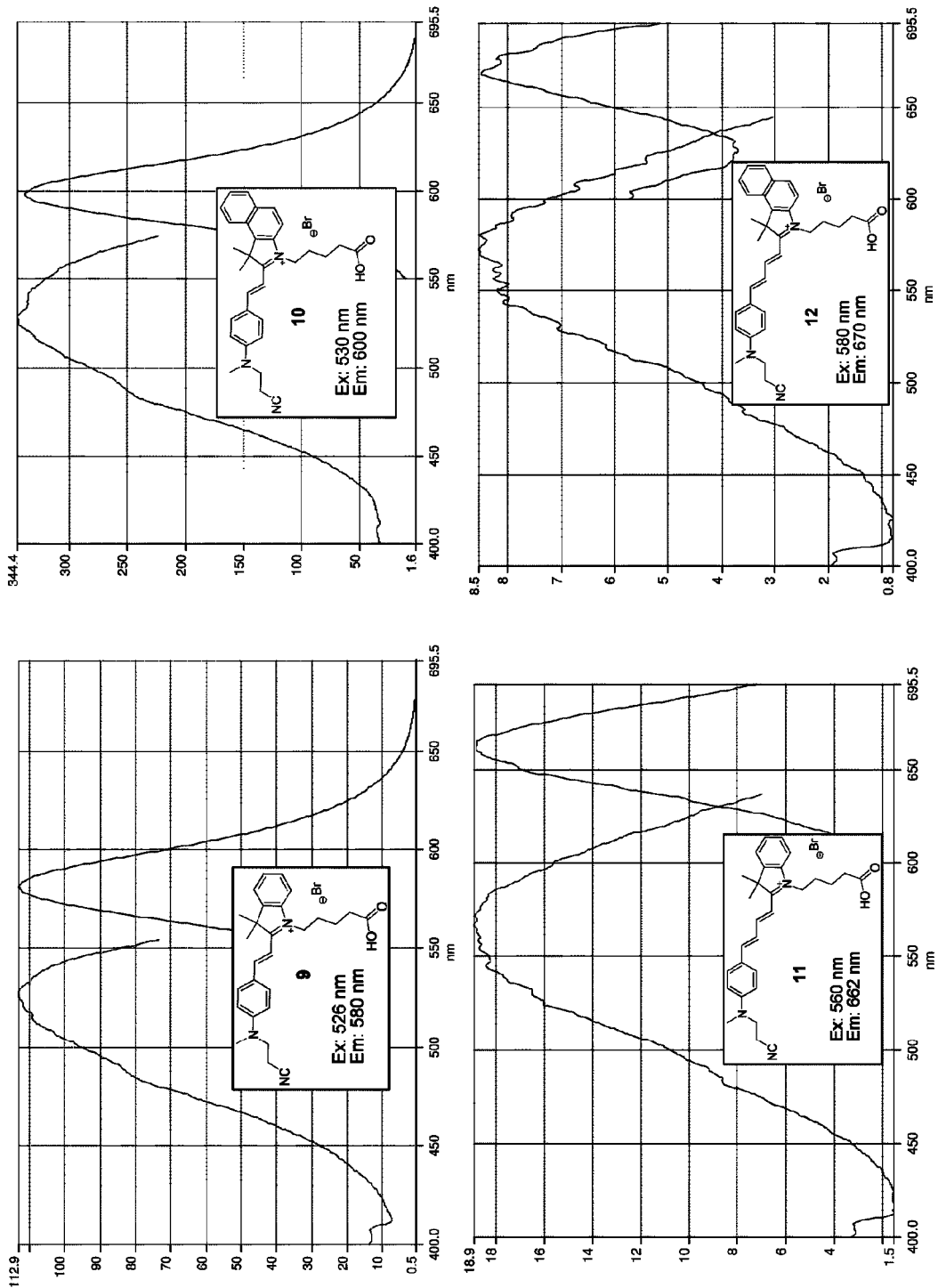
FIG. 25 Fluorescence excitation and emission spectra of four hemicyanine dyes.

| Sequence Name | EDC# | Sequence | [Seq] | Units | Function | structure |
|---|---|---|---|---|---|---|
| (693-687-688-493) | EDC1 | GTGGTAGTTGGAGCTGGTGGCGTAGG CAAGA (SEQ ID NO. 74) | 200 | nM | Target | I_H1_A0 |
| (693-687-56-16) | EDC10 | GTGGTAGTTGGAGCTGGAGCGGCAAC GGAGA (SEQ ID NO. 81) | 200 | nM | Target | I_H2_A1 |
| (37-101-688-493) | EDC11 | GACGTGTTCAAGGTGGTGGCGTAGG CAAG (SEQ ID NO. 82) | 200 | nM | Target | BI_H1_A0 |
| (37-101-56-16) | EDC12 | GACGTGTTCAAGGGTGGAGCGGCAAC GGAGA (SEQ ID NO. 83) | 200 | nM | Target | BI_H2_A1 |
| (693-687) | EDC2 | *AGCTCCAACTACCAC (SEQ ID NO. 75) | 600 | nM | Probe | Indolinium (I) |
| (688-493) | EDC5 | TCTTGCCTACGCCAC* (SEQ ID NO. 78) | 400 | nM | Probe | Aldehyde0 (A0) |
| (37-101) | EDC7 | *ACCCTTGAACACGTC (SEQ ID NO. 79) | 600 | nM | Probe | Benzoindolinium (BI) |
| (56-16) | EDC8 | TCTCCGTTGCCGCTC* (SEQ ID NO. 80) | 400 | nM | Probe | Aldehyde1 (A1) |

FIG. 26 DNA sequences for four-plex hemicyanine dye generation.

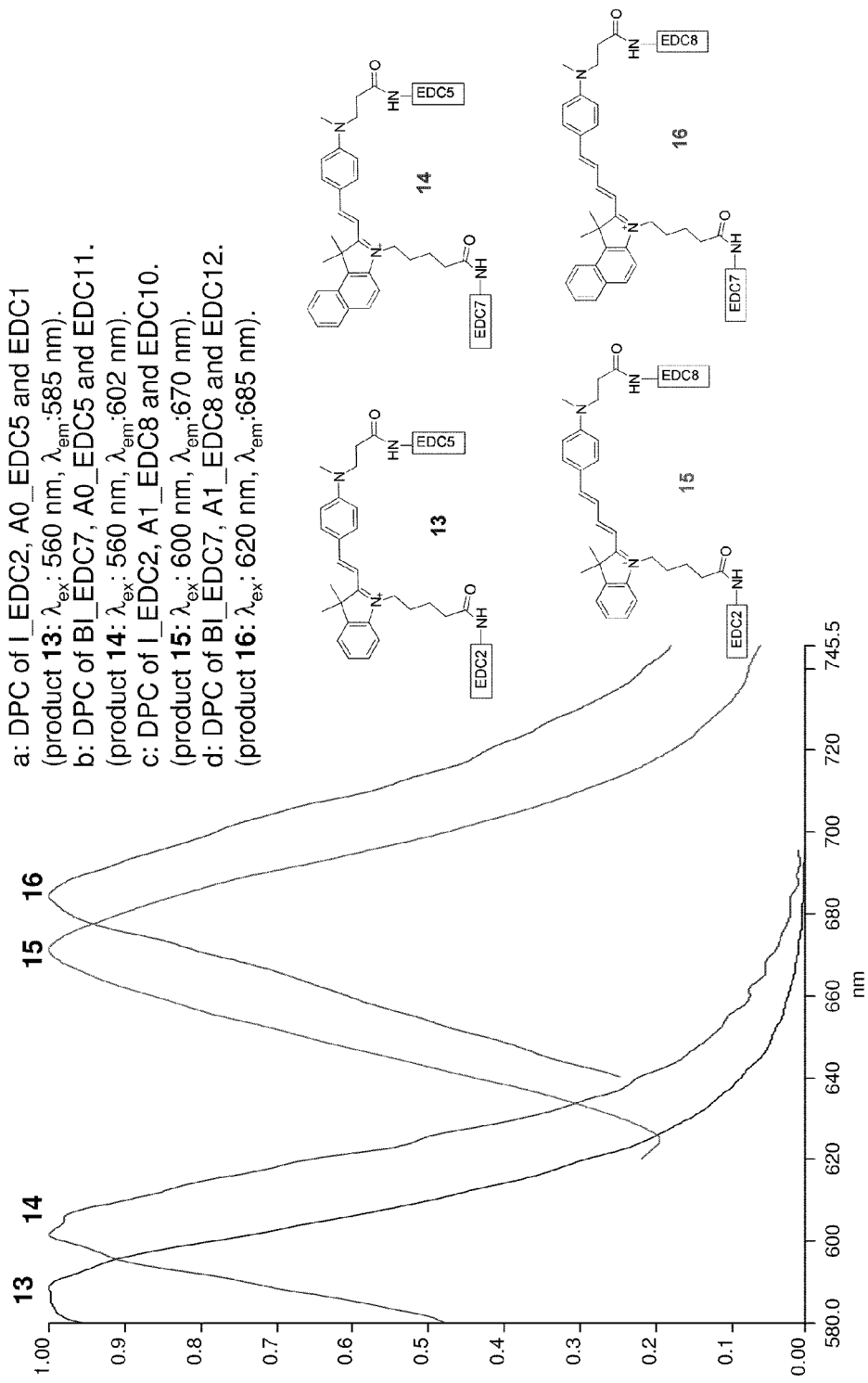
FIG. 27 Normalized fluorescence spectra of four individual DPC reactions (a to d) after 140 minutes at RT (the chemical structures of the DPC products 13 to 16 are shown on the right).

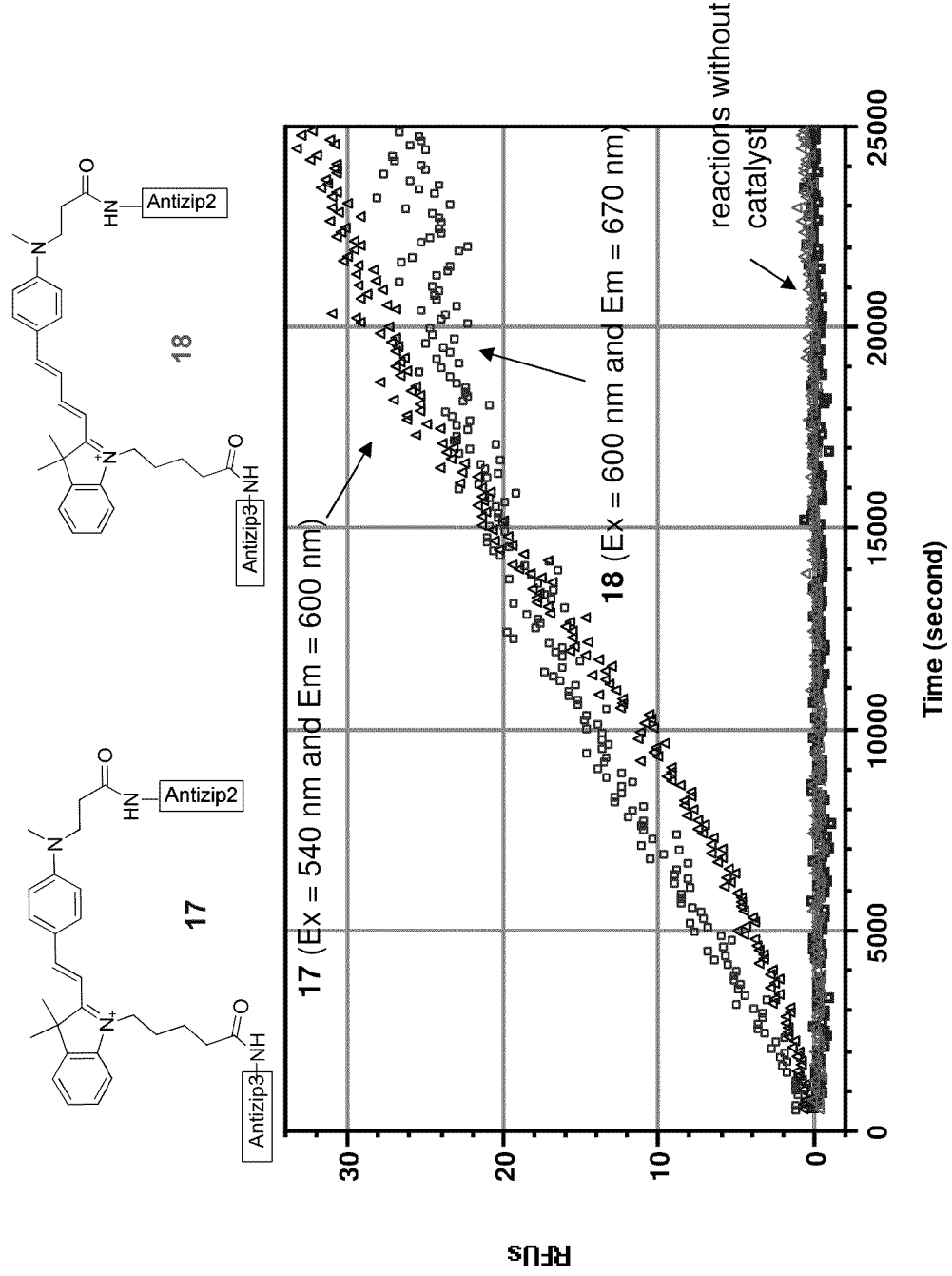
FIG. 28 Fluorescence kinetic analysis of DPC reactions of Antizip3_indolinium/Antizip2 reporter1_A0 (triangle) and Antizip3_indolinium/ Antizip2 reporter1_A1 (circle).

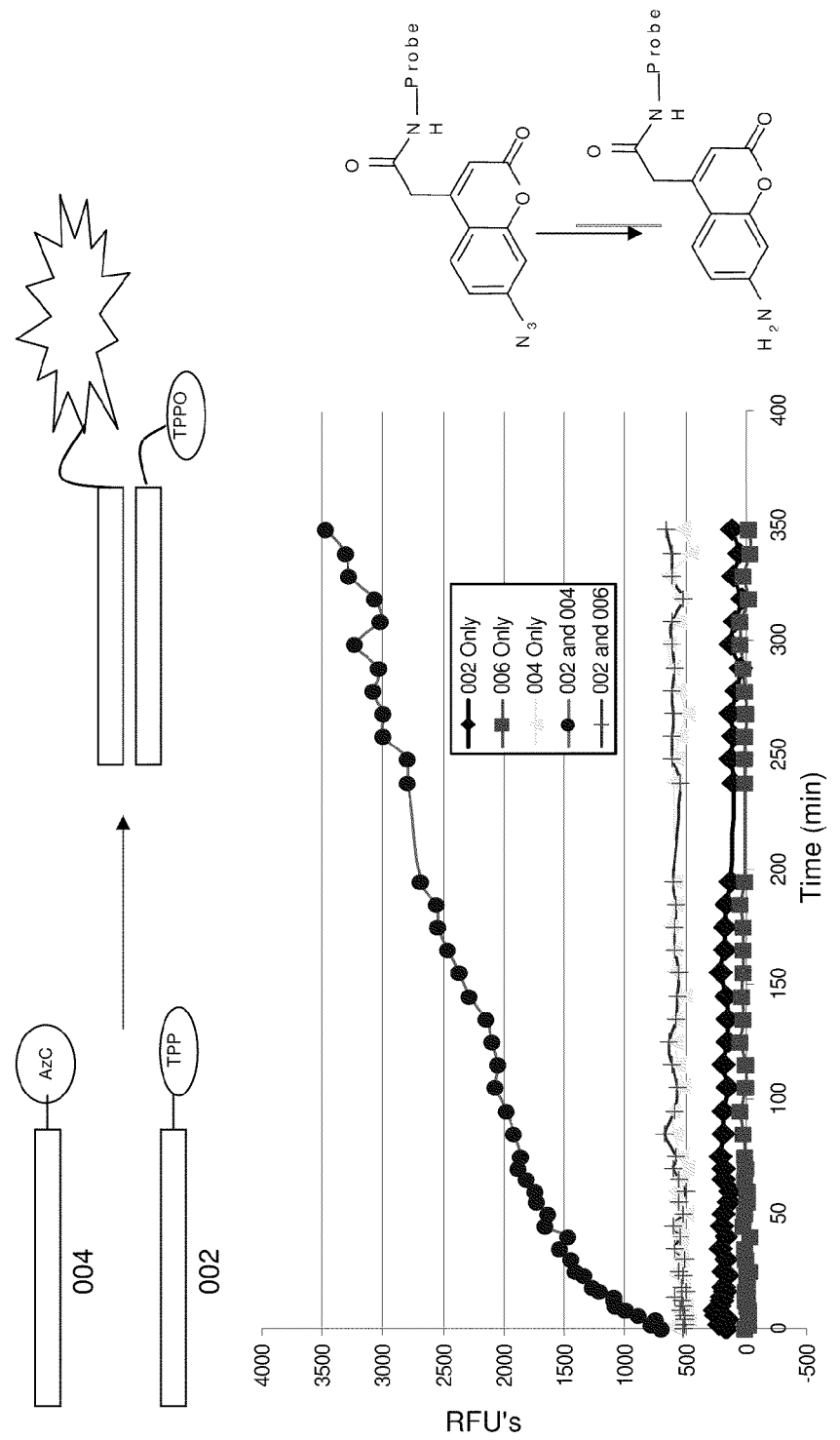

FIG. 32
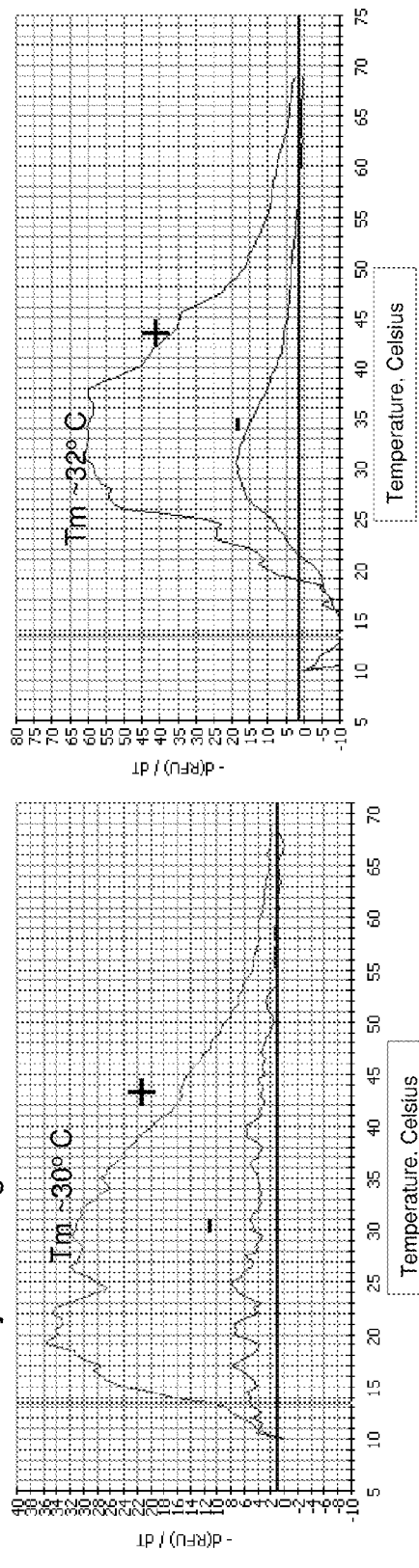
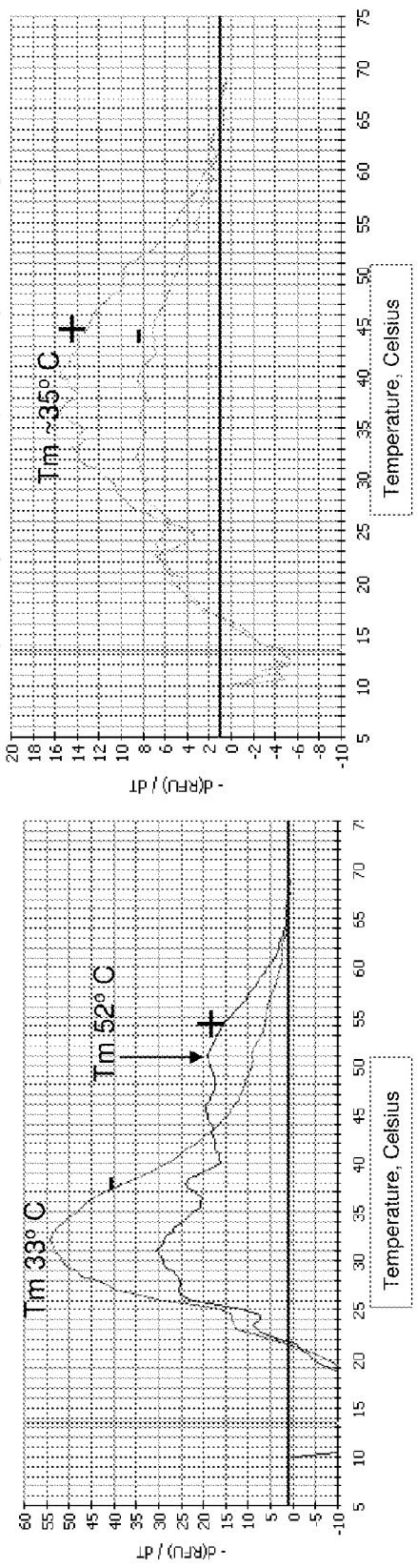
"Hot Start" DNA Hybrid Melting Curves +/- Avidin
100 nM oligos, 100 nM avidin, 25 mM salt FIG. 34   Salt Concentrations – Effect upon $T_m$ Melting Curves of 5' and 3' (-) Biotin-Strand Oligos duplexed with Biotin-5' (+) Strand Oligo Melting Curves of AT-rich Biotinylated Oligo Dimers +/- Target (+) 5'-TTTTTTTTTTTTTTAATTAAA-3'   (SEQ ID NO: 27)
(-) 3' AAATTAATTTTTTTTTTTTT-5'   (SEQ ID NO: 27)

Homogeneous Assay Detection of PDGF-AA with Aptamer-DPC Probes

- Dependence of the splinted architecture upon the presence of both aptamer and reporter oligonucleotides.
- All reactants were tested at 0 or 0.4 µM concentration, at 22°C, in 50 mM Tris/HCl pH 8.5 – 10 mM $MgCl_2$ – 35% v/v formamide.
- Fluorescence was measured in a Wallac Victor Luminometer with excitation at 350 nm and emission at 460 nm.

Reaction rates at various ratios of TPP to AzC aptamers oligonuceotides (A) or reporters to aptamers (B).

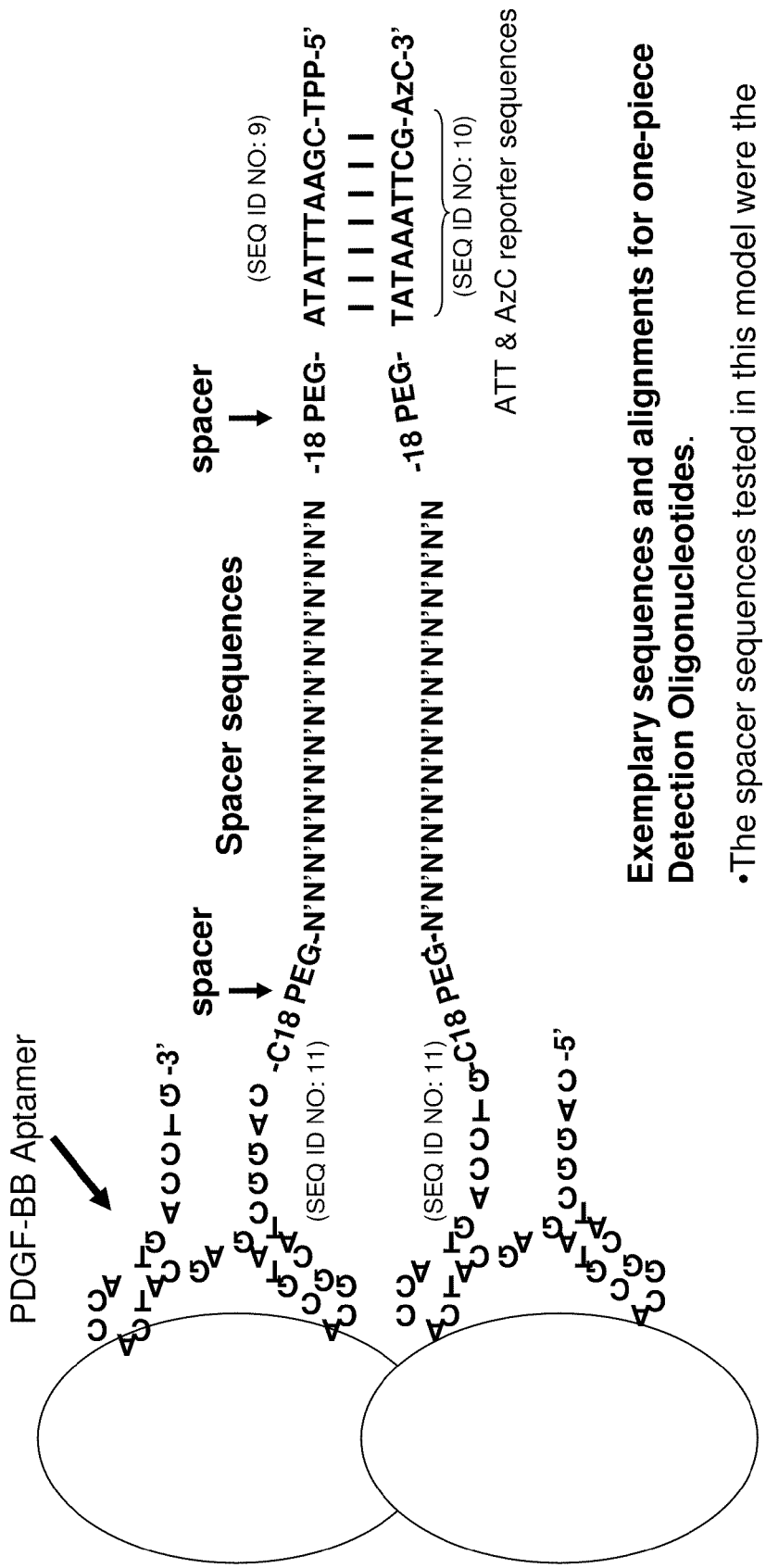

COMPOSITIONS AND METHODS FOR BIODETECTION BY NUCLEIC ACID-TEMPLATED CHEMISTRY

RELATED APPLICATIONS

This application is a continuation-in-part of International Patent Application Serial No. PCT/US2007/021094, filed Sep. 28, 2007, which claims the benefit of and priority to U.S. patent application Ser. Nos. 60/847,859, filed Sep. 28, 2006; 60/905,364, filed Mar. 7, 2007; and 60/918,023, filed Mar. 14, 2007; and International Patent Application Serial No. PCT/US2007/021094 is a continuation-in-part of International Patent Application Serial No. PCT/US2007/020223, filed Sep. 18, 2007, the entire disclosure of each of which is incorporated by reference herein for all purposes.

FIELD OF THE INVENTION

The present invention relates generally to probes and their use in biodetection and diagnostics. More particularly, the invention relates to compositions and methods for biodetection using nucleic acid-templated chemistry (e.g., synthesis of compounds having desired fluorescent, chemiluminescent or chromophoric properties in a multiplex detection of nucleic acids or proteins).

BACKGROUND

Fluorescent and colored compounds have been used in the fields of biological research and medicine to detect the presence, absence, state, quantity, and composition of biomolecules. Assays using fluorescent and colored compounds may be performed in vitro, in situ, or in vivo. Examples of commonly used in vitro assays for detection of DNA and RNA are real-time and end-point polymerase chain reaction (PCR), DNA sequencing, and DNA microarray technologies.

Recently, there has been an increased amount of literature published on detection methods for multiple analytes, most of which involves genetic analysis and some relates to protein detection. See, e.g., U.S. Pat. No. 6,890,741.

In a typical nucleic acid detection method used for diagnostic and molecular biology research, multiple gene probes complementary with a gene of interest are labeled with small molecules that can be detected by spectroscopic, electrochemical, biochemical or immunochemical means. PCR is generally incorporated for the amplification of targeted gene sequences. To achieve detection of multiple analytes, fluorescence-based technologies have been used often due to fluorescence dyes readily available. For example, primers have been labeled with different fluorescence dyes and the changes in fluorescence were monitored upon hybridization to their complements (e.g., WO 2002/057479). In other cases, the multiplex detection was achieved by using intercalating dyes as labels in DNA restriction fragment analysis and capillary electrophoresis with frequency-domain fluorescence lifetime detection method (McIntosh, et al., *Electrophoresis*, 2002, 23, 1473-1479). Since these methods use pre-labeled fluorescence dyes, the detection sensitivity relies largely on the separation of target bound and unbound fluorescence labeled probes. Though solid phase immobilization of the target gene (fluorescence in situ hybridization, for example) can improve the separation efficiency by simply washing away the unbound fluorescence labeled probes, this introduces an extra process. However, the potential background still can be high, and the procedure can be laborious. To address this problem, a non-fluorescence label moiety can be attached to the probes so that the fluorescence signal only occurs after the hybridization event. Recently, the development of DNA-programmed chemistry has provided a novel approach for generation of fluorescence dye in situ. See, e.g., Li, X.; Liu, D. R. *Angew. Chem. Int. Ed.* 2004, 43, 4848-4870; U.S. Pat. No. 7,070,928.

Polymethine dye has been widely used as laser dyes, photographic sensitizers and fluorescence probes due to its superior fluorescence and photochemical properties. However, polymethine dyes are generally synthesized by acid/base catalyzed condensation under anhydrous conditions which is not comparable to the nucleic acid-templated chemistry (Jedrzejewska, et al. *Dyes and Pigments* 2003, 58, 47-58). Recently, the literature has reported an improved aldol condensation in water using Lewis-acid (Kobayashi, et al., *J. Am. Chem. Soc.* 1998, 120, 8287-8288) and enamine-based organocatalyst (Mase, et al. *J. Am. Chem. Soc.* 2006, 128, 734-735). The quaternary salt of polymethine precursor (active hydrogen component) used for condensing with aldehyde, however, is different substantially from the precursor (alpha carbon of aldehyde) in a conventional aldol condensation.

Thus, there exists a need for new fluorescent and colorimetric technologies that address many of the shortcomings inherent in the above-mentioned biodetection methods. For example, there is a need for methods of polymethine dye synthesis from non-detectable precursors by nucleic acid-templated chemistry and adaptation of such chemistry to biodetection.

SUMMARY OF THE INVENTION

The present invention is based, in part, upon the discovery that nucleic acid-templated chemistry can be applied in detection of multiple biological targets simultaneously. The present invention is based, in part, upon the discovery that polymethine dyes can be synthesized by nucleic acid-templated chemistry. Assays of this invention may be performed in vitro, in situ, or in vivo.

In one aspect, the present invention relates to a method for making a polymethine dye comprising conducting an aldol condensation between an aldehyde and an active hydrogen component in an aqueous condition in the presence of an organocatalyst.

In some embodiments, the condensation reaction is:

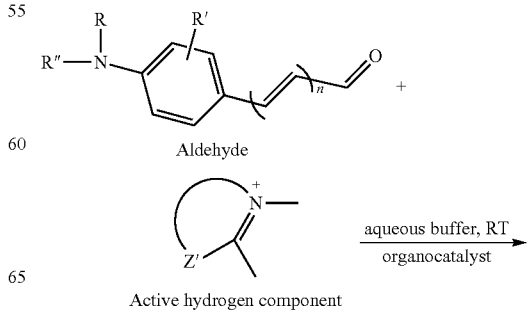

Aldehyde

Active hydrogen component

-continued

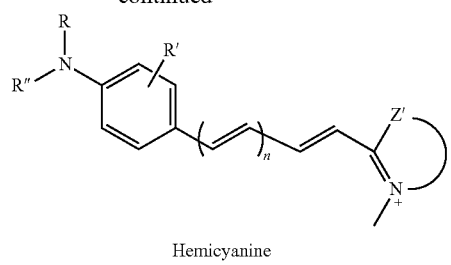

Hemicyanine wherein
Z' = O, S, Se, P, NH$_2$, NR, C(CH$_3$)$_2$ where R is alkyl group
n = 0, 1, 2 ...
R = H, alkyl
R" = H, alkyl, alkyl carboxylic acid
R' = Ph or N-heterocycle, H, alkyl, SO$_3$H, OH, CN, Cl, Br, NO$_2$, NH$_2$, N(R)$_2$, OR where R is alkyl group and wherein the organocatalyst is a secondary amine, a primary amine, a bifunctional amine-acid catalyst or a diamine. The secondary amine may be a pyrrolidine, a piperidine, a nornicotine, or an analog thereof, for example. The primary amine may be a valine or a peptide having fewer than 3 amino acid units, for example. The bifunctional amine-acid catalyst may be pyrrolidine/AcOH, for example. The diamine catalyst may be N1,N1-dimethylethane-1,2-diamine, propane-1,2-diamine, 1-(2-aminoethyl)-piperidine, or an analog thereof, for example.

In some embodiments, the organocatalyst is represented by:

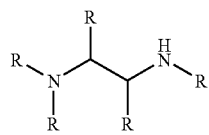

wherein each R is independently selected from hydrogen or C$_1$-C$_6$ straight or branched alkyl.

In another aspect, the invention generally relates to a hemicyanine dye having the chemical structure of (I), (II) or (III), for example, prepared by the methods disclosed herein.

(I)

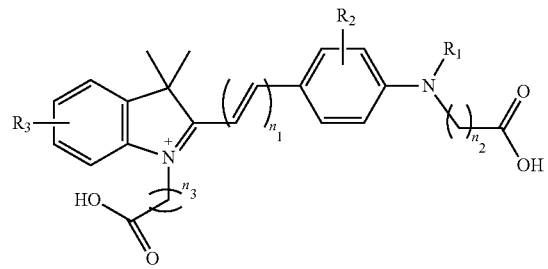

wherein
Z'=O, S, Se, P, NH$_2$, NR, C(CH$_3$)$_2$ where R is alkyl group
n=0, 1, 2 ...
R=H, alkyl
R"=H, alkyl, alkyl carboxylic acid
R'=Ph or N-heterocycle, H, alkyl SO$_3$H, OH, CN, Cl, Br, NO$_2$, NH$_2$, N(R)$_2$, OR where R is alkyl group (II)

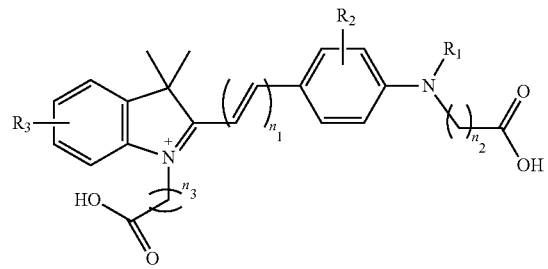

n1 = 1, 2, 3, 4, 5
n2, n3 = 0 to 16
R1 = alkyl
R2 = Ph, H, alkyl, SO$_3$H, OH, CN, Cl, Br, NO$_2$, NH$_2$, N(R$_1$)$_2$, OR$_1$ while R$_1$ is alkyl group
R$_3$ = Ph, H, alkyl, SO$_3$H, OH, CN, Cl, Br, NO$_2$, NH$_2$, N(R$_1$)$_2$, OR$_1$ while R$_1$ is alkyl group (III)

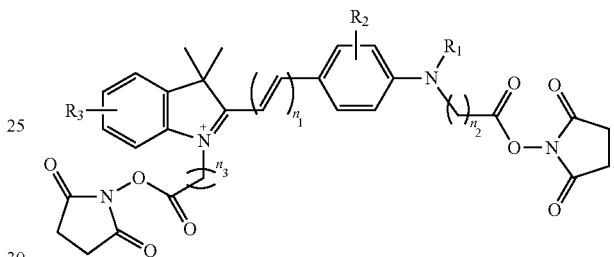

n1 = 1, 2, 3, 4, 5
n2, n3 = 0 to 16
R1 = alkyl
R2 = Ph, H, alkyl, SO$_3$H, OH, CN, Cl, Br, NO$_2$, NH$_2$, N(R$_1$)$_2$, OR$_1$ while R$_1$ is alkyl group
R$_3$ = Ph, H, alkyl, SO$_3$H, OH, CN, Cl, Br, NO$_2$, NH$_2$, N(R$_1$)$_2$, OR$_1$ while R$_1$ is alkyl group In yet another aspect, the invention generally relates to an aldehyde having the chemical structure of IV or V:

(IV)

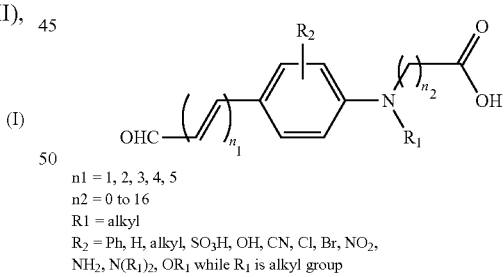

n1 = 1, 2, 3, 4, 5
n2 = 0 to 16
R1 = alkyl
R$_2$ = Ph, H, alkyl, SO$_3$H, OH, CN, Cl, Br, NO$_2$, NH$_2$, N(R$_1$)$_2$, OR$_1$ while R$_1$ is alkyl group (V)

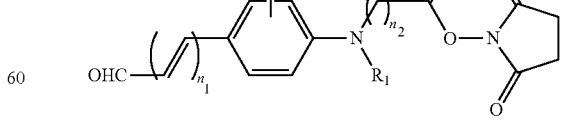

n1 = 1, 2, 3, 4, 5
n2 = 0 to 16
R1 = alkyl
R$_2$ = Ph, H, alkyl, SO$_3$H, OH, CN, Cl, Br, NO$_2$, NH$_2$, N(R$_1$)$_2$, OR$_1$ while R$_1$ is alkyl group In yet another aspect, the invention generally relates to a quaternary salt having the chemical structure of VI or VII:

(VI)

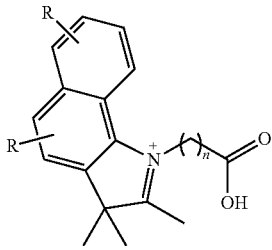

n = 0 to 16
R = H, alkyl, SO₃H, OH, CN, Cl, Br, NO₂, NH₂, N(R₁)₂, OR₁ while R₁ is alkyl group (VII)

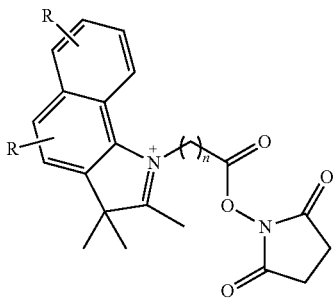

n = 0 to 16
R = H, alkyl, SO₃H, OH, CN, Cl, Br, NO₂, NH₂, N(R₁)₂, OR₁ while R₁ is alkyl group In yet another aspect, the invention generally relates to an quaternary salt-nucleic acid conjugate having the chemical structure of:

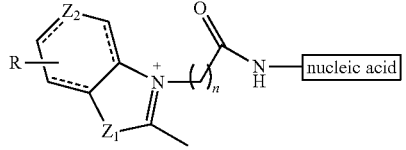

n = 0 to 16
Z₁ = O, S, Se, P, NH₂, NR₁, C(CH₃)₂ where R₁ is alkyl group
R = any substituted benzyl or higher fused benzyl rings, H, alkyl, SO₃H, OH, CN, Cl, Br, NO₂, NH₂, N(R₁)₂, OR₁ while R₁ is alkyl group
Z₂ = benzene or any N-heterocycles In yet another aspect, the invention generally relates to an aldehyde-nucleic acid conjugate having the chemical structure of:

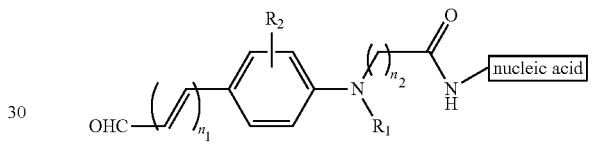

n1 = 1, 2, 3, 4, 5
n2 = 0 to 16
R1 = H, alkyl
R₂ = Ph, or N-heterocycle, H, alkyl, SO₃H, OH, CN, Cl, Br, NO₂, NH₂, N(R₁)₂, OR₁ while R₁ is alkyl group In yet another aspect, the invention generally relates to a hemicyanine dye-nucleic acid conjugate having the chemical structure of:

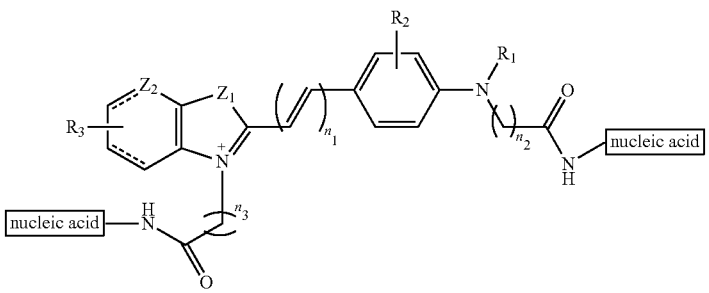

n1 = 1, 2, 3, 4, 5
n2 and n3 = 0 to 16
Z1 = O, S, Se, P, NH₂, NR₁, C(CH₃)₂ where R₁ is alkyl group
R₃ = any substituted benzyl or higher fused benzyl rings, H, alkyl, SO₃H, OH, CN, Cl, Br, NO₂, NH₂, N(R₁)₂, OR₁ while R₁ is alkyl group
Z₂ = benzene or any N-heterocycles
R1 = H, alkyl
R₂ = Ph or N-heterocycle, H, alkyl, SO₃H, OH, CN, Cl, Br, NO₂, NH₂, N(R₁)₂, OR₁ while R₁ is alkyl group In yet another aspect, the invention generally relates to making a hemicyanine-nucleic acid conjugate comprising conducting a nucleic acid-templated reaction between an aldehyde and quaternary salt disclosed herein to make a hemicyanine disclosed herein.

In some embodiments, the nucleic acid-templated reaction is in an end of helix architect. In some other embodiments, the nucleic acid-templated reaction is in a middle of helix architect.

In yet another aspect, the invention generally relates to a method for selecting a dye having a desired fluorescent property. The method includes (a) preparing a library of oligonucleotide-encoded dyes through nucleic acid-templated synthesis; (b) hybridizing the oligonucleotide-encoded dyes with spatially arrayed complementary oligonucleotide probes immobilized on a solid support; (c) measuring the absorption and fluorescence properties of the oligonucleotide-encoded dye directly on the solid support; (d) identifying the oligonucleotides that encode the dyes having the desired fluorescence properties based on the position of the immobilized complementary oligonucleotide probes, and (e) identifying and characterizing the chemical structure of the dyes having the desired fluorescence property.

In yet another aspect, the invention generally relates to a method for detecting multiple target nucleotide sequences. The method includes: (a) providing a number of probe pairs, the number equal to the number of target nucleotide sequences, wherein each probe pair comprises (1) a first probe comprising (i) a first oligonucleotide sequence and (ii) a first reactive group linked to the first oligonucleotide sequence, and (2) a corresponding second probe comprising (i) a second oligonucleotide sequence and (ii) a second reactive group linked to the second oligonucleotide sequence, wherein the first oligonucleotide sequence and the second oligonucleotide sequence are complementary to two separate regions of a corresponding target nucleotide sequence; (b) combining the probe pairs with a sample to be tested for the presence of the target nucleotide sequences under conditions where the first probes and the second probes hybridize to their respective complementary regions of the target nucleotide sequences if present in the sample thereby bringing into reactive proximity the first reactive groups and the corresponding second reactive groups; and (c) detecting one or more reactions between the first reactive groups and the corresponding second reactive groups thereby determining the presence of the target nucleotide sequences.

The number of target nucleotide sequences may be between about 2 to about 20, for example, 2 to 6. The target nucleotide sequences may be in solution phase. The target nucleotide sequences may be attached to a solid support. In some embodiments, the one or more reactions between the first reactive groups and the corresponding second reactive groups generate fluorescent compounds that may be detected. In some embodiment, the one or more reactions between the first reactive groups and the corresponding second reactive groups generate chemiluminescent compounds that may be detected.

The one or more reactions between the first reactive groups and the corresponding second reactive groups may comprise an aldol condensation reaction, for example. The one or more reactions between the first reactive groups and the corresponding second reactive groups may comprise a Wittig reaction.

The invention encompasses a kit that provides one, two or more of the probes described herein. More particularly, the invention encompasses a kit that provides one, two or more of the probes that utilize nucleic acid-templated chemistry for the generation of detectable signals as a way for detecting the presence of biological targets.

The foregoing aspects and embodiments of the invention may be more fully understood by reference to the following figures, detailed description and claims.

Definitions

The term, "DNA programmed chemistry" or "DPC", as used herein, refers to nucleic acid-templated chemistry, for example, sequence specific control of chemical reactants to yield specific products accomplished by (1) providing one or more templates, which have associated reactive group(s); (2) contacting one or more transfer groups (reagents) having an anti-codon (e.g., complementary sequence with one or more templates) and reactive group(s) under conditions to allow for hybridization to the templates and (3) reaction of the reactive groups to yield products. For example, in a one-step nucleic acid-templated reaction, hybridization of a "template" and a "complementary" oligonucleotide bring together reactive groups followed by a chemical reaction that results in the desired product. Structures of the reactants and products need not be related to those of the nucleic acids comprising the template and transfer group oligonucleotides. See, e.g., U.S. Pat. No. 7,070,928 and U.S. Application Publication No. 2004/0180412 A1, by Liu et al.; Gartner, et al., 2004, Science, vol. 305, pp. 1601-1605; Doyon, et al., 2003, JACS, vol. 125, pp. 12372-12373, all of which are expressly incorporated herein by reference in their entireties. See, also, "Turn Over Probes and Use Thereof" by Coull et al., PCT International Patent Application PCT/US06/16999, filed on May 3, 2006; U.S. patent application Ser. No. 11/441,804, "Biodetection by Nucleic Acid-Templated Chemistry" by Coull et al., filed on May 26, 2006.

The terms, "nucleic acid", "oligonucleotide" (sometimes simply referred to as "oligo") or "polynucleotide" or as used herein refer to a polymer of nucleotides. The polymer may include, without limitation, natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadeno sine, 7-deazaguano sine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages). Nucleic acids and oligonucleotides may also include other polymers of bases having a modified backbone, such as a locked nucleic acid (LNA), a peptide nucleic acid (PNA), a threose nucleic acid (TNA).

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions may be conducted simultaneously.

BRIEF DESCRIPTION OF THE FIGURES

The invention may be further understood from the following figures in which:

FIG. 1 illustrates the general chemical structures of polymethine, cyanine and hemicyanine dyes.

FIG. 2 illustrates the general chemical structures of hemicyanine dyes useful for multiplex and their aldehyde and quaternary salt precursors.

FIG. 3 illustrates the chemical structures of a four-plex hemicyanine-DNA dye system and their spectroscopic properties.

FIG. 4 is a schematic representation of solution phase-based DPC fluorescence assay for multiple analytes.

FIG. 5 is a schematic representation of solid phase-based DPC fluorescence assay for multiple analytes.

FIG. 6 is a schematic representation of immunohistochemistry test for multiple family receptor dimers in non-zip-coded architecture.

FIG. 7 is a schematic representation of immunohistochemistry test for multiple family receptor dimers in zip-coded architecture.

FIG. 8 is a schematic representation of a method for the detection of a biological target under one embodiment of the present invention.

FIG. 10 shows examples of hybridization as affected by concentration, temperature, and the presence or absence of a single base pair mismatch.

FIG. 11 shows exemplary oligonucleotides used in certain melting curve experiments.

FIG. 14 shows exemplary embodiment of a splinted, zip-coded detection system with aptamers as target binding moieties.

FIG. 15 shows exemplary embodiment of a splinted, zip-coded detection system with antibodies as target binding moieties.

FIG. 16 shows exemplary embodiment of a splinted, zip-coded detection system with antibodies as target binding moieties.

FIG. 17 shows absorption and fluorescence emission spectra of DPC reaction mixtures (end of helix).

FIG. 18 shows absorption and fluorescence emission spectra of DPC reaction mixtures (end of helix).

FIG. 19 shows LC-MS data of a crude DPC reaction mixture.

FIG. 21 shows absorption and fluorescence emission spectra of DPC reaction mixtures.

FIG. 23 shows certain fluorescence intensity data of a DPC reaction.

FIG. 24 shows certain fluorescence intensity data of a DPC reaction.

FIG. 25 shows fluorescence excitation and emission spectra of four hemicyanine dyes.

FIG. 26 shows exemplary DNA sequences useful for four-plex hemicyanine dye generation.

FIG. 27 shows normalized fluorescence emission spectra of four DNA conjugated hemicyanine dyes from middle of helix DPC reactions.

FIG. 28 shows fluorescence kinetic analysis of two DPC reactions in end of helix architecture.

FIG. 29 shows an example of fluorescence signal generation and biological target detection via triphenylphosphine (TPP) and azidocoumarin (AzC) reporter chemistry.

FIG. 32 shows certain examples with DNA hybridization melting curves of biotinylated oligonucleotides with and without avidin.

FIG. 48 illustrates an embodiment of a "one-piece" detection system for the detection of PDGF.

DETAILED DESCRIPTION OF THE INVENTION

Figure 9:
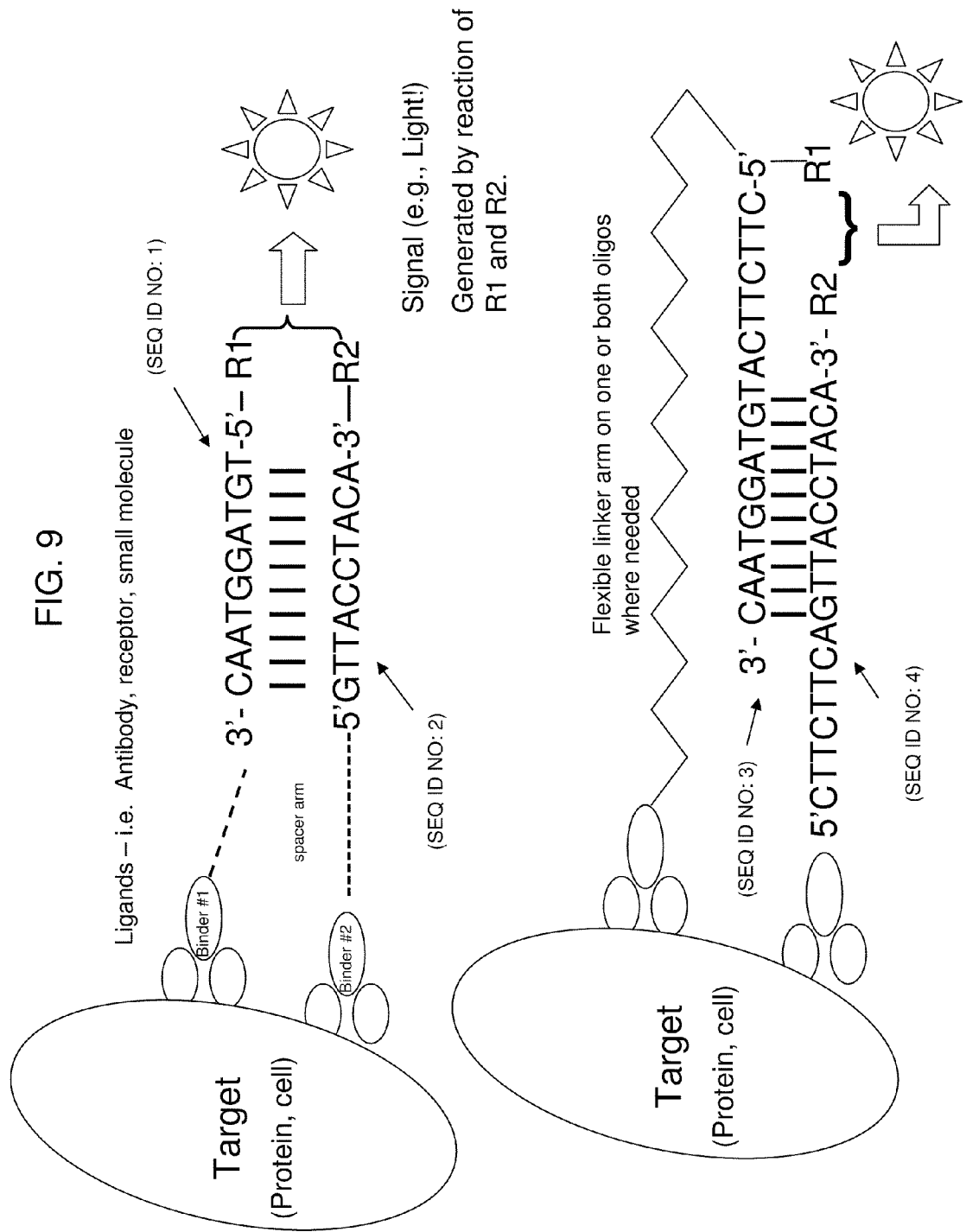
FIG. 9 is a schematic representation of a method for the detection of a biological target under one embodiment of the present invention.

In its simplest sense, the invention is to detect the presence of target analytes via nucleic acid-templated chemistry, for example, through measurement of fluorescence of polymethine dyes generated by nucleic acid-templated reactions templated by target nucleic acids or proteins. The present invention provides methods for analysis of multiple analytes in a convenient, accurate and sensitive way. For example, in the detection of nucleic acids, the method uses nucleic acid probes conjugated with non-fluorescence precursor (e.g., aldehydes and methyl quaternary salts) and polymethine multiplex dyes are generated through the chemical reaction of the probes upon hybridization with target nucleic acids. In addition, the invention provides novel chemical compositions of polymethine dyes and methods of synthesizing polymethine dyes in conventional reactions under aqueous conditions as well as via nucleic acid-templated chemistry.

Polymethine Dye Chemistry

Polymethine dye is characterized by a chain of methine (—CH=) groups with an electron donor (D) and an electron acceptor (A) at opposite ends of their polyene chain (FIG. 1, Zollinger, Color Chemistry: Syntheses, Properties, and Applications of Organic Dyes and Pigments, 3nd Edn., Verlag Helvetica Chimica Acta, Postfach, Switzerland, 2003). Typical A and D terminals for polymethine dyes (as shown in FIG. 1) include thiazoles, pyrroles, pyrrolines, indoles, 1,3,3-trimethylindolines, tetrazoles, pyrimidine, pyridines, quinolines, and higher fused N-heterocycles or any substituted benzyl rings. If the terminals are both N-atom containing heterocycles, the compound is named cyanine. If only one N-atom is part of the ring system, the compound is named hemicyanine. By changing the number of the vinyl group in the polyene chain, the fluorescence emission wavelength of the polymethine dye can be tuned from near-UV to near-IR. The terminal group may also provide mean for finer tuning.

Scheme 1 depicts hemicyanine formation through organocatalytic aldol condensation in aqueous buffer. Some of the general organocatalysts such as pyrrolidine analogues have been listed here. By using catalyst, the reaction condition for the hemicyanine formation can switch from anhydrous to aqueous condition. The percentage of the water content used depends only on the solubility of the starting materials.

Scheme 2 is a schematic illustration of hemicyanine dye generation through DPC in the presence of organocatalyst. The general chemical structures of component A (aldehyde_DNA), component B (quaternary salt bearing active hydrogen component) and hemicyaine_DNA conjugate have also been described. The fluorescence emission wavelength of the hemicyaine dye can be tuned by changing the number of the vinyl group in the polyene chain (n) or by using different substitute groups (R') and terminal groups in component B.

FIG. 2 shows the general chemical structures of hemicyanine dyes useful for multiplex and their aldehyde and quaternary salt precursors. An example of four-plex hemicyanine_DNA dyes derived from the general structure and their maximum UV absorption and fluorescence's emission wavelength has been described in FIG. 3.

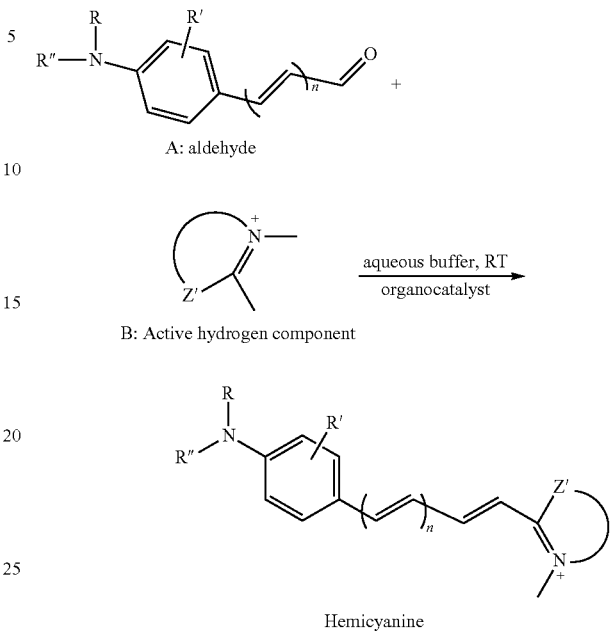

Scheme 1: Hemicyanine formation through organocatalytic aldol condensation in aqueous buffer.

A: aldehyde

B: Active hydrogen component

Hemicyanine

Organocatalysts:

1) Pyrrolidine, piperidine analogues
2) Amino acid such as valine or small peptide
3) Bifunctional amine-acid catalysts such as pyrrolidine/AcOH
4) Diamine such as dimethythe-1,2-diamine, propane-1,2-diamine

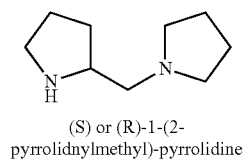

(S) or (R)-1-(2-pyrrolidnylmethyl)-pyrrolidine

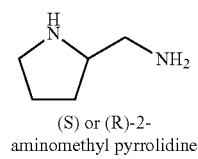

(S) or (R)-2-aminomethyl pyrrolidine

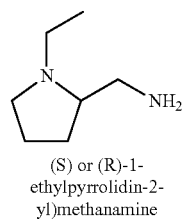

(S) or (R)-1-ethylpyrrolidin-2-yl)methanamine

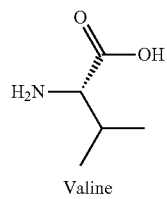

Valine

-continued

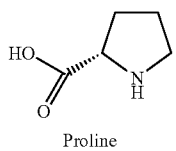
Proline

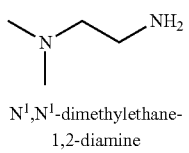
N¹,N¹-dimethylethane-
1,2-diamine
DMEDA

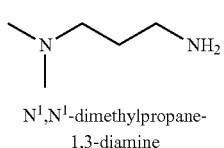
N¹,N¹-dimethylpropane-
1,3-diamine

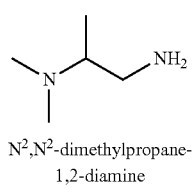
N²,N²-dimethylpropane-
1,2-diamine

-continued

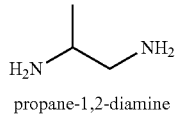
propane-1,2-diamine

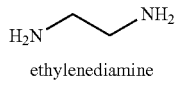
ethylenediamine

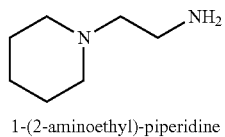
1-(2-aminoethyl)-piperidine

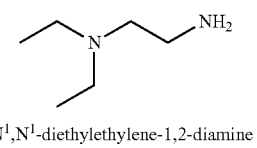
N¹,N¹-diethylethylene-1,2-diamine $Z' = O, S, Se, P, NH_2, NR, C(CH_3)_2$ where R is alkyl group
$n = 0, 1, 2 \ldots$
$R = H$, alkyl
$R'' = H$, alkyl, alkyl carboxylic acid
$R' = $ Ph or N-heterocycle, H, alkyl, $SO_3H$, OH, CN, Cl, Br, $NO_2$, $NH_2$, $N(R)_2$, OR where R is alkyl group Scheme 2: Hemicyanine dye generation through organocatalyst catalyzed DPC.

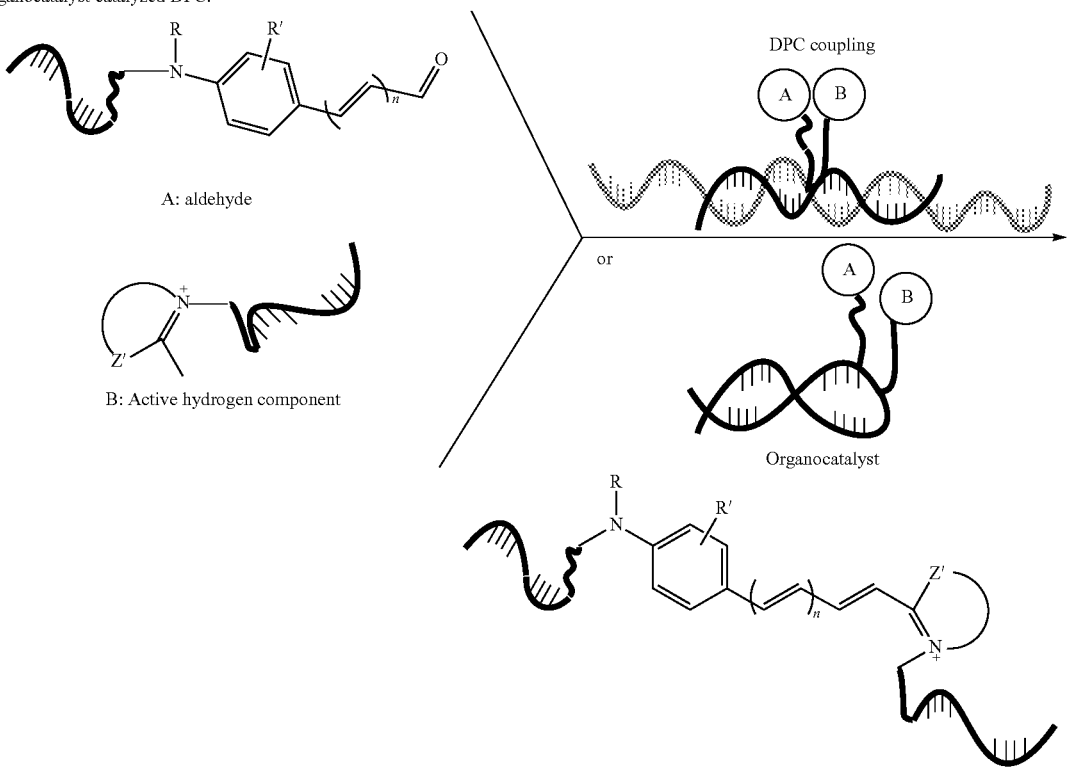

$Z' = O, S, Se, P, NH_2, NR, C(CH_3)_2$ where R is alkyl group
$n = 0, 1, 2 \ldots$
$R = H$, alkyl
$R' = $ Ph or N-heterocycle, H, alkyl, $SO_3H$, OH, CN, Cl, Br, $NO_2$, $NH_2$, $N(R)_2$, OR where R is alkyl group FIG. 4 is a schematic illustration of solution phase based DPC fluorescence assay for multiplex detection involving multiple analytes. Each pair is labeled with non-fluorescence precursors complementary to a sequence that is indicative of a specific polymorphic site or genotype in the diagnostic determination of infection with a virus which can be PCR-amplified products. After hybridization, DPC fluorescence product will be formed. By changing the hybridization conditions such as salt and temperature, only matched pairs will generate the fluorescence signal. No washing process is needed to remove any non-fluorescence precursors. This method is not only useful for analyzing or detecting polynucleotide sequences, it also can be used, for example, in an antibody based assay utilizing a nucleic acid conjugated antibody.

FIG. 5 is a schematic illustration of a solid phase based DPC fluorescence assay for multiple analytes. Different solid supports can be used to immobilize genes of interest, such as a glass plate, a polymer or a gold plate. After hybridization and fluorescence compound formation by catalyzed DPC, the solid support can be visualized directly by fluorescence microscopy or detected by a fluorescence reader without the need for washing.

FIG. 6 illustrates a multiplexed immunohistochemistry (IHC) test for multiple family receptor dimers. Multiple pairs of probes, each pair being directed at a particular homo- or hetero dimer and with a distinct DPC product (e.g., a distinct fluorescent signal from each pair as shown), can provide simultaneous detection and profiling of multiple receptor dimers. Both zip-coded, as illustrated in FIG. 7, and non-zip-coded probe pairs can be employed in a multiplex test. See, e.g., International Patent Application Serial No. PCT/US07/020223, filed Sep. 18, 2007.

There are a number of advantages to the detection methods disclosed here. 1) Zero background. There is no background fluorescence signal for aldehyde and quaternary salt precursors when excited at the polymethine product's excitation wavelength. Since the DPC reaction only happens in the presence of the catalyst and the aldehyde and quaternary salt precursors are very stable, no decomposition of precursors will be observed and thus there is no background fluorescence of the decomposed product. 2) Simplicity. The fluorescence generation is performed in one-pot and the detection is achieved in situ without isolation of the product. 3) Specificity. The fluorescence generation is based on the sequence specific nucleic acid interaction, so the signal generation is specific to the nucleic acid sequence. 4) A larger number of analytes can be detected as compared to conventional methods. The fluorescence emission wavelength of polymethine dye can be easily tuned from far UV to near IR, so multi-wavelength dyes can be generated in one-pot by utilizing multi-codon DNAs. The numbers of analyte that can be detected are not limited by the DPC and dye chemistry.

Various and general aspects of nucleic acid-templated chemistry are discussed in detail below. Additional information may be found in U.S. Pat. Nos. 7,070,928, and 7,223,545, European Patent No. 1,423,400 B1 and U.S. Application Publication No. 2004/0180412 A1 (U.S. Ser. No. 10/643,752) by Liu et al. Gartner, et al., 2004, Science, vol. 305, pp. 1601-1605; Doyon, et al., 2003, JACS, vol. 125, pp. 12372-12373, all of which are expressly incorporated herein by reference in their entireties. See, also, "Turn Over Probes and Use Thereof" by Coull et al., PCT WO07/008,276A2, filed on May 3, 2006.

DPC-Based Protein Detection

Methods and compositions of biodetection using nucleic acid-templated chemistry based probes are described in WO06128138A2 by Coull et al., which is incorporated herein by reference in its entirety.

FIG. 8 and FIG. 9 illustrate one embodiment of the invention for the detection of a protein target.

FIG. 8 shows an embodiment of detection of a protein target by DPC-based probes. Two probes contain target binding moieties, complementary oligonucleotides, and chemically reactive species X and Y, respectively. Upon hybridization, X and Y react to create a signal generating (e.g., fluorescent) compound, which may or may not covalently link both probes. The reaction product of X and Y may also be released as an unbound, soluble compound into the solution. The protein target may be attached to a solid-phase such as the surface of a bead, glass slide (microarray), etc., or be in solution. The target binding moieties may be aptamers, antibodies, antibody fragments (i.e., Fab), receptor proteins, or small molecules, for example.

More particularly illustrated in FIG. 9 is an example of the dual-probe approach with two probes, each carrying a "prefluorophore" precursor (R1 and R2) and containing a binding moiety for a target and an oligonucleotide sequence that is designed to anneal to each other. In this embodiment, the detection is performed under conditions such that the prefluorophore oligos will not anneal to each other in the absence of a target. These conditions are generally selected such that the ambient temperature is higher than the $T_m$ of the oligonucleotide pairs in the absence of the target (so that the oligo pairs will not anneal in the absence of the intended target analyte). In the presence of the intended target, however, the localized high concentration of the oligos then shifts the $T_m$ of their double stranded complex upwards so that hybridization occurs, which is followed by a signal-generating nucleic acid-templated reaction (a reaction between R1 and R2). The signal-generating nucleic acid-templated reaction is accelerated both due to the localized higher concentration of the prefluorophores, but may also be facilitated by the proximity and orientation of the prefluorophore groups towards one another. This configuration of signal generation has the potential to enable creation of kits for the detection of various biomolecules, cells, surfaces and for the design of in situ assays. The signal generation does not require enzymes and the homogeneous format requires no sample manipulation.

In FIG. 9, two oligonucleotides are shown, each of which is linked through an optional spacer arm to a separate binder, as shown in this case is an antibody but may be other binders such as aptamers or small molecules. Each antibody recognizes a separate epitope on a common target analyte such as a protein. Spacer arms can be added to one or both oligonucleotides between the oligo and the binder. In certain cases, this spacer arm may be required to meet proximity requirements to achieve a desired reactivity. Spacer arms in principle can be any suitable groups, for example, linear or branched aliphatic carbon chains C3 to C5, C10, C15, C20, C25, C30, C35, C40, or C100 groups, a DNA sequence of 1 to 10, 15, 20, 30, 50 or 100 bases long, or polyethylene glycol oligomers of the appropriate length.

The prefluorophores may reside in an "end of helix" configuration (FIG. 9 top), one attached to the 5' end of an oligo and other to the 3' end. (Other configurations can be applied, including placing the two prefluorophores within the sequence or having one oligo hybridize to a partial hairpin structure (e.g., 100 Angstroms long), for example.) In the first example, one oligonucleotide is attached to a 5' to a spacer arm and a target binder, and the other 3' is attached to a spacer arm and separate target binder. Spacer arms, which can consist of non-complementary DNA sequences, or synthetic spacer arms such as oligomers of ethylene glycol, can be added to meet proximity requirements. Such spacer arms can be very flexible, which has the advantage of overcoming any steric hindrance to binding that might occur with a rigid spacer. A suitably long spacer arm design can permit both oligonucleotides to be linked 5' to their binders (FIG. 9 bottom), or both linked 3', as long as the oligonucleotides can anneal in the antiparallel configuration and allow the reactive groups to react with each other. An optimal spacer arm length may be designed for each target. Spacer arms which are excessively long should be avoided as they may reduce specificity in the system or a reduced increased $T_m$ effect.

The proximity effect afforded by tethering the pair of oligonucleotides may affect the kinetics of annealing of two complementary oligonucleotide sequences compared to the two oligonucleotides free in solution. More importantly, a localized high concentration shifts the melting curve upwards compared to the free complex, i.e. increase the $T_m$ of the complex. In a bulk solution, it is known that $T_m$ has dependence upon total oligonucleotide concentration as illustrated in the equation below. Wetmur, *Criti. Rev. in Biochem. And Mol. Biol.*, 1991, 26, 227-259.

$$T_m = (1000 * \Delta H)/(A + \Delta S + R \ln(C_t/4)) - 273.15 + 16.6 \log Na^+)$$

where $\Delta H$ and $\Delta S$ are the enthalpy and entropy for helix formation, R is the molar gas constant, $C_t$ is the total concentration of oligomers, and $Na^+$ is the molar concentration of sodium ion in the solution.

FIG. 10 shows that the slope of $T_m$ vs. concentration within the range of short oligonucleotides in 0.1 M salt has a dependence of about +7° C. per 10-fold increase in concentration of oligonucleotides (sequences in FIG. 11) based on the above equation. So, for example, a 1000-fold increase in local concentration would be expected to raise $T_m$ by about +21° C.

Reaction products of R1 and R2 may be released from the hybridization complex as a result of the chemical transformation. Thus, the fluorophore or chromophore may be separated from the hybridization complex and analyzed independently, or the fluorophore or chromophore and the annealed oligonucleotides may be removed once detected so that additional rounds of interrogation of the sample can be conducted. The reaction between R1 and R2 may or may not be covalently linked to the two probes once the product(s) is formed.

Figure 12:
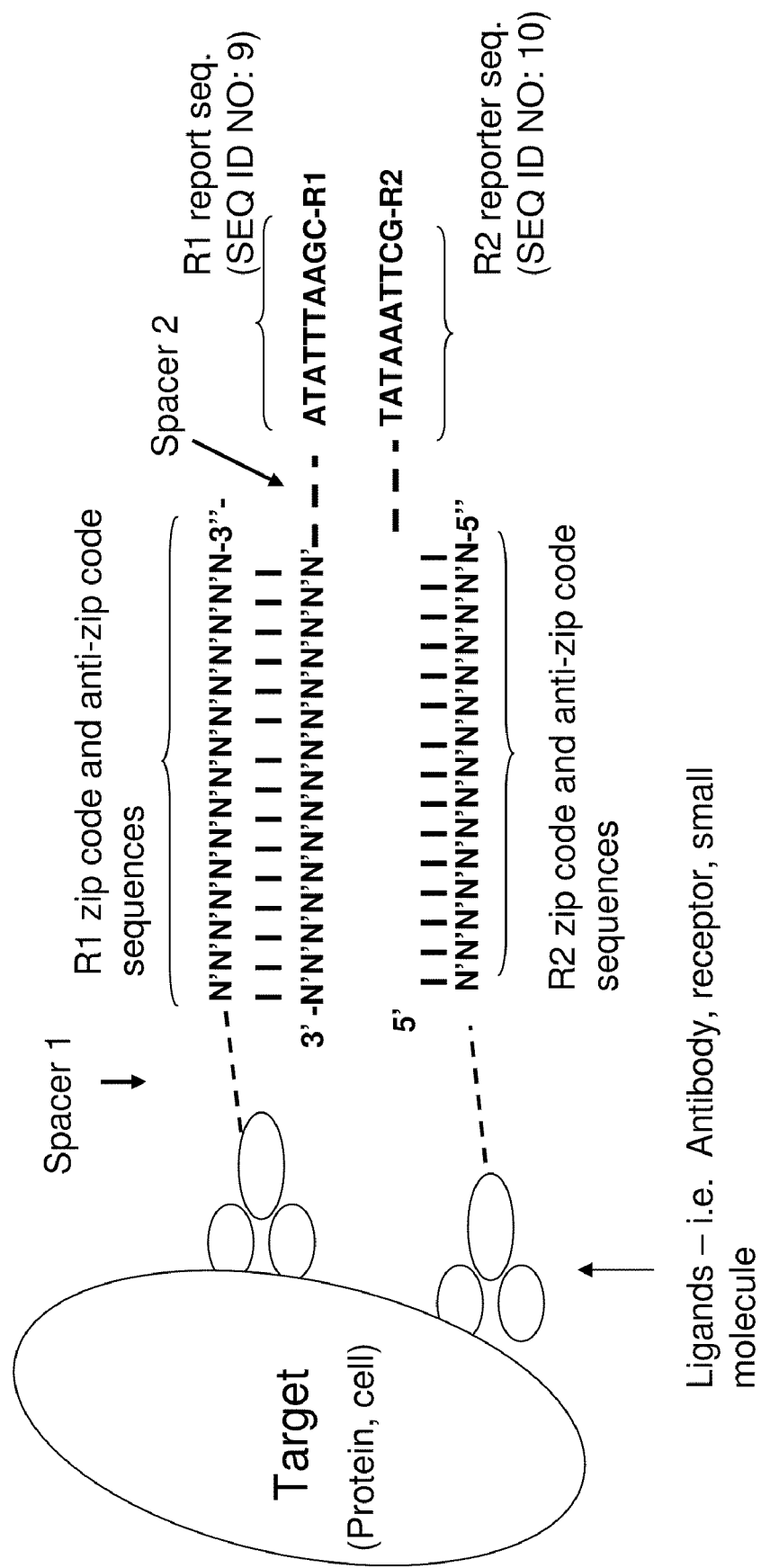
FIG. 12 is a schematic representation of a method for the detection of a biological target under one embodiment of the present invention.

FIG. 12 illustrates another embodiment of the invention, which employs a "zip-coded" splint architecture for nucleic acid template-based biodetection. In this embodiment, instead of the target binding moieties being directly linked (optionally via spacer groups) to the complementary oligonucleotides that hybridize and set up nucleic acid templated reactions, the target binding moieties is linked to a "zip code" oligonucleotide sequence. Each of the corresponding reporter oligonucleotides has a complementary, "anti-zip code" sequence (in addition to a "reporter" sequence that sets up nucleic acid-templated reaction). The nucleic acid-templated chemical reactions are set up by the hybridization of the reporter oligos, which are linked to reactive groups that react and generate detectable signals. It is important that each oligonucleotide sequence of the probes is complementary only to its intended hybridization partner and not complementary to other oligonucleotides in the detection system.

This zip-coded architecture supports creating a single reporter-oligonucleotide conjugate which would assemble with different downstream reporter oligonucleotides through an anti-zip code sequence. Libraries of different reporters linked to a unique anti-zip code may be tested simply by mixing each one with stoicheometric amounts of the binder-zip code oligonucleotide conjugate with its complementary zip code.

Figure 13:
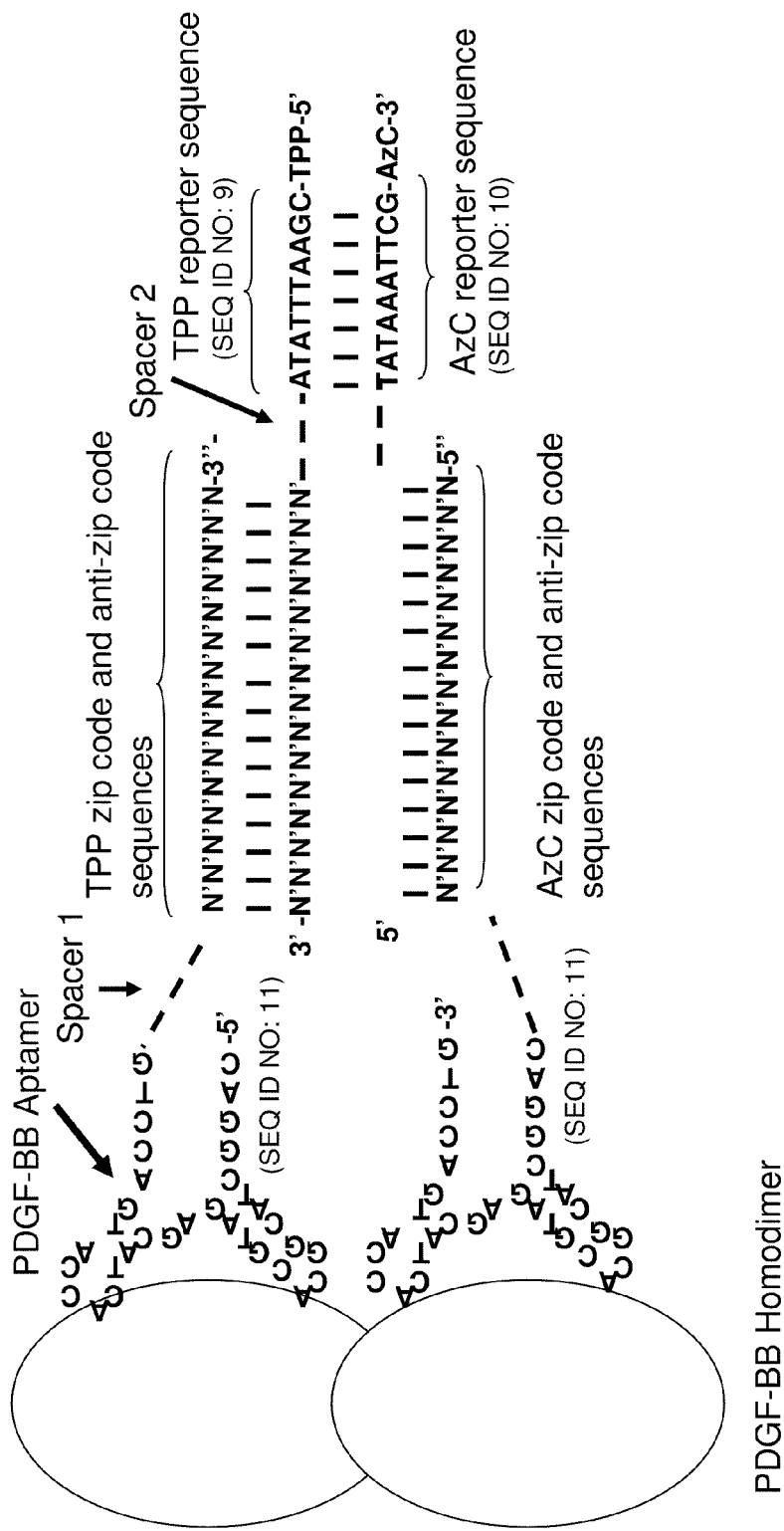
FIG. 13 is a schematic representation of a method for the detection of platelet derived growth factor (PDGF) under one embodiment of the present invention.

FIG. 13 is an illustration of a zip-coded splinted architecture approach where the target binding moieties are two aptamers. In this example for detection of platelet derived growth factor (PDGF) with illustrative oligo sequences and reporter chemistry (e.g., triphenylphosphine, TPP, and 7-azidocoumarin, AzC), the TPP reporter oligonucleotide self-assembles to the PDGF aptamer oligonucleotide through hybridization of zip code sequence (NNN . . . ) to the complementary anti zip code sequence (N'N'N' . . . ) on the TPP reporter oligonucleotide. The reporter oligonucleotide terminates with an exemplary 10-base reporter sequence and a 5'-TPP group. A separate pair of oligonucleotides, with different zip codes and anti-zip codes (complementary to each other pairwise), also self-assembles to provide the AzC reporter sequence and a 3'-AzC group. The AzC oligonucleotides are complementary and antiparallel to the TPP oligonucleotides so the TPP and AzC groups terminate end-to-end when the TPP and AzC oligonucleotides anneal to each other.

FIG. 14 illustrates in more detail the zip-coded splinted architecture approach for detection of PDGF with illustrative oligo sequences and reporter chemistry (TPP and AzC). The TPP pair includes, first, a PDGF-aptamer on the 5'-end, a C18 polyethylene-glycol based spacer, and an 18-mer zip code sequence. The TPP reporter sequence includes a complementary anti-zip code sequence on its 3' terminus, a C18 PEG spacer, and a ten base pair reporter sequence terminating in a 5' TPP group. The AzC pair of oligonucleotides includes a 3'-aptamer linked through a C18 PEG spacer to a separate zip code, and a detection oligonucleotide linked to a 5' anti-zip code, a C18 PEG spacer, and a reporter oligonucleotide (complementary to the TPP oligonucleotide) terminating in a 3' AzC group.

FIG. 15 illustrates an example of the corresponding architect where antibodies are used instead of aptamers as target binding moieties.

One advantage of the "zip coded" approach is the ability to create the reporter oligonucleotides separately, and have them assemble together with binders under conditions retaining the activities of both the binders and of the nucleic acid template-activated chemistry.

The zip-coded system is based upon two pairs of oligonucleotides, with each pair being held together by the base-pairing of a unique zip code and an anti-zip code pair. "Zip codes" are oligonucleotide sequences which bind specifically to their complementary sequences, and preferably are designed such they are not complementary to known genomic sequences (relevant if the sample may contain genomic DNA), have similar $T_m$ values, lack significant secondary structure, and do not anneal to other zip code or anti-zip code sequences in the detection system.

It is worth pointing out the methods of the invention do not require enzymatic or chemical ligation of the first and/or the second oligonucleotide sequences.

Factors that may be considered in optimizing a design of a zip-coded architecture include, for example, (1) spacer groups (e.g., oligonucleotides and/or non-base groups) between the aptamer/antibody and zip codes (spacer 1), e.g., to allow hybridization partners to reach each other, to prevent any steric hindrance; (2) Length of a zip code sequence in order to form a sufficiently stable annealing to the anti-zip code sequence to form the complex; and (3) Spacer groups (spacer 2) between the anti-zip code and the reporter sequence, e.g., to prevent any steric hindrance.

The binders (target binding moieties) attached to the oligonucleotides may be any chemical moieties that specifically bind to a target molecule and allow the design of the invention to work. Examples include a wide range of functionalities, such as (1) antibodies: e.g., IgG, IgM, IgA, IgE, Fab's, Fab', F(ab)$_2$, Dab, Fv or ScFv fragments; (2) small molecule binders, such as inhibitors, drugs, cofactors; (3) receptors for protein detection, and vice versa; (4) DNA, RNA, PNA aptamers; (5) DNA sequences for DNA-binding and regulatory proteins; (6) peptides representing protein binding motifs; (7) peptides discovered through phage display, random synthesis, mutagenesis; (8) naturally binding protein pairs and complexes; (9) antigens (for antibody detection); and (10) a single polyclonal antibody separately attached to two oligonucleotides may serve as two separate binders of different specificity.

The target binding moieties attached to the oligonucleotides may be of heterogeneous types directed against different sites within the same target. For example, the two binders may be two different antibodies, an antibody and a receptor, an antibody and a small molecule binder, a receptor and a peptide, an aptamer and a cofactor, or any other combination.

The target analytes can be of any type, provided the target supports two (or more) binding sites. Molecules which exist in equilibrium with a monomeric form and a homodimeric or higher polymerization phase may be detected by a pair of probes containing the same binder but different complementary DNA sequences. Suitable targets include proteins, cell surfaces, antibodies, antigens, viruses, bacteria, organic surfaces, membranes, organelles, in situ analysis of fixed cells, protein complexes. The invention may be particularly suited for the detection of fusion proteins (e.g., BCR-ABL in the presence of BCR and ABL).

In the design of the probes, one consideration is the $T_m$ of the two reporter sequences carrying the reactive groups. Since the $T_m$ of the duplex should be below room temperature in the absence of a target, this sequence normally should be short, for example 6-15 bases and/or A-T rich. A typical reporter length of 10 base pairs might have a $T_m$ of around 30° C. at a low salt concentration. Therefore, it is often necessary even with a short sequence to add 10% to 40% volume/volume formamide to further lower the temperature below assay temperature, or to elevate the assay temperature. Very short reporter oligonucleotides may suffer from a lack of specificity and exhibit some binding to zip code sequences (when these are employed) which is undesirable.

Another factor in the design of the probes is the length of oligonucleotide in between the binding moiety and the reporter sequence, including any zip code sequences. These must be long enough for the reporter oligonucleotides to reach each other and anneal. The sequences may be interspersed with polyethylene glycol (PEG) linkers that are flexible and may afford additional protection against any steric hindrance. For example, total lengths of oligonucleotides may be around 35 bases long. Oligonucleotides containing 0, 1, or 2 C18 PEG spacers, or homopolymer tracts may also be utilized (i.e. $C_{10}$).

A third consideration is the length of zip and anti-zip sequences when these are employed (i.e. FIG. 13 and FIG. 16). Aside from the need for each zip code to anneal only to its anti-zip code, and not any other zip code, anti-zip code, or reporter sequence, an important parameter is the $T_m$ of the duplex between the zip codes and anti-zip codes. The $T_m$ should be substantially higher than the highest temperature that will be used in the assay in order that the reporter oligonucleotides remain firmly attached to the binding moiety. In practice, zip codes of about twice the length of the reporter sequences (i.e. total length of 15-30 bases) are desirable and generally meet these criteria.

Regarding signal generation, nucleic acid-templated chemistry may be used to create or destroy a label that effects an optical signal, e.g., creating or destroying a fluorescent, chemiluminescent, or colorimetric molecule. Additionally, a detection reaction may be designed to create or destroy a product that directly or indirectly creates a detectable label, for example, a product that catalyzes a reaction that creates an optical label; inhibits a reaction that creates an optical label; is a fluorescence quencher; is a fluorescent energy transfer molecule; creates a Ramen label; creates an electrochemiluminescent label (i.e. ruthernium bipyridyl); produces an electron spin label molecule.

The following examples contain important additional information, exemplification and guidance that can be adapted to the practice of this invention in its various embodiments and equivalents thereof. Practice of the invention will be more fully understood from these following examples, which are presented herein for illustrative purpose only, and should not be construed as limiting in anyway.

EXAMPLES

Examples 1 to 4 are related to DNA probe preparation. Both the aldehyde and heterocyclic precursors bearing an active hydrogen component can be conjugated to DNA through amide bond formation. First, an acid heterocyclic or aromatic precursor is synthesized. The acid is then converted to the active N-hydroxysuccimide ester (NHS ester) that readily reacts with DNA bearing amine functionality.

Oligonucleotides were prepared using standard phosphoramidite chemistry and purified by reversed-phase C18 column (Glen Research, Sterling Va., USA). Oligonucleotides bearing 5'-amino groups were prepared using 5'-Amino-Modifier 5 and oligonucleotides bearing 3'-amino-groups were prepared using 3'-Amino-Modifier C7 CPG (Glen Research, Sterling Va., USA). Concentration of the DNA and heterocyclic conjugated DNA was determined by UV absorbance at 260 nm. The contribution of the UV absorbance at 260 nm from the heterocyclic moiety in the heterocyclic conjugated DNA was negligible and was not considered.

TABLE 2

Oligonucleotide Sequences

| Oligo | sequence (5'-3') | ID No. |
|---|---|---|
| Zip2 | TTGGTGCTCGAGTCCCCCCCCCCCCCCCCCCCCC-NH$_2$ | (SEQ ID NO: 66) |
| Zip3 | NH2-CCCCCCCCCCCCCCCCCCCCGCTGCCATCGATGGT | (SEQ ID NO: 67) |
| Zip5 | NH2-CCCCCCCCCCCCCCCCCCCGTGCCATCCATAGTCAG | (SEQ ID NO: 68) |
| Antizip2 reporter1 | GGACTCGAGCACCAATAC-X-TATAAATTCG-NH2 | (SEQ ID NO: 69) |

TABLE 2-continued

Oligonucleotide Sequences

| Oligo | sequence (5'-3') | ID No. |
|---|---|---|
| Antizip3 reporter | NH2-CGAATTTATA-X-CTGACCATCGATGGCAGC | (SEQ ID NO: 70) |
| Antizip5 reporter mismatch | NH2-CCAATTAATA-X-CTGACTATGGATGGCACG | (SEQ ID NO: 71) |
| Antizip5 reporter | NH2-CGAATTTATA-X-CTGACTATGGATGGCACG | (SEQ ID NO: 72) |
| Antizip2 report2 | GGACTCGAGCACCAATACXTATAAATTCGCCC | (SEQ ID NO: 73) |
| EDC1 | GTGGTAGTTGGAGCTGGTGGCGTAGGCAAG | (SEQ ID NO: 74) |
| EDC2 | H2N-AGCTC CAACTACCAC | (SEQ ID NO: 75) |
| EDC3 | H2N-AGATCCCACTAGCAC | (SEQ ID NO: 76) |
| EDC4 | GTGGTAGTTGGAGCT-NH2 | (SEQ ID NO: 77) |
| EDC5 | TCTTGCCTACGCCAC-NH2 | (SEQ ID NO: 78) |
| EDC7 | NH2-ACCCTTGAACACGTC | (SEQ ID NO: 79) |
| EDC8 | TCTCCGTTGCCGCTC-NH2 | (SEQ ID NO: 80) |
| EDC10 | GTGGTAGTTGGAGCTGGAGCGGCAACGGAGA | (SEQ ID NO: 81) |
| EDC11 | GACGTGTTCAAGGGTGGTGGCGTAGGCAAGA | (SEQ ID NO: 82) |
| EDC12 | GACGTGTTCAAGGGTGGAGCGGCAACGGAGA | (SEQ ID NO: 83) |

X = Spacer Phosphoramidite 18 (Glen Research, Sterling VA, USA)

Example 1

DNA Conjugated Quaternary Salt

Scheme 3 gives one example of synthesizing DNA conjugated quaternary salt bearing active hydrogen component (indolinium_DNA). 2,3,3-trimethylindolenine is commercially available. The acid functionality is introduced to the indoline ring through N-quaternization.

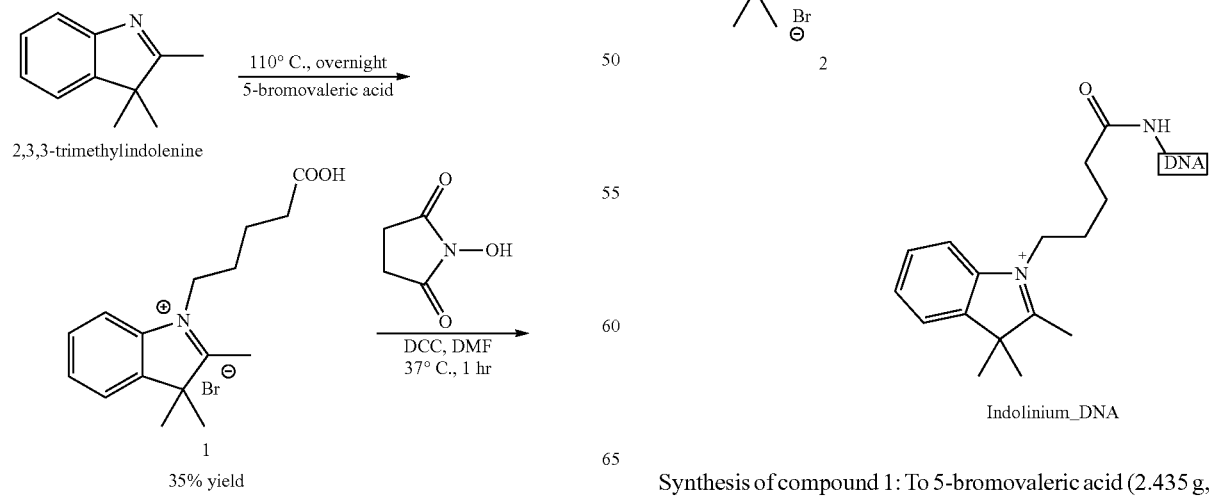

Scheme 3: Example of synthesizing DNA conjugated quaternary salt bearing active hydrogen component (indolinium_DNA).

Synthesis of compound 1: To 5-bromovaleric acid (2.435 g, 13.45 mmole) was added 2,3,3-trimethylindolenine (2.141 g, 13.45 mmole). The reaction mixture was heated with rigorous stirring at 110° C. overnight. The dark red sticky oil obtained was transferred to a Gregar extractor and extracted with EtOAc overnight. A light red solid was obtained. The solid was redissolved in 30 mL of MeOH. MeOH was removed under reduced pressure and the remaining residue was treated with 10 mL of EtOAc. Brownish solid was precipitated out and filtrated. The solid was washed with 2×50 mL of acetone and 2×100 mL of EtOAc. Total 1.590 g of light brownish solid was obtained (35% yield). $^1$H NMR (DMSO) $\delta_{ppm}$: 7.98 (m, 1H), 7.84 (m, 1H), 7.61 (m, 2H), 4.49 (t, 2H), 2.84 (s, 3H), 2.30 (t, 2H), 1.84 (m, 2H), 1.63 (m, 2H), 1.53 (s, 6H). MALDI-MS (positive mode): 260.2419.

Synthesis of compound 2: Compound 1 (0.1 g, 0.294 mmole), N-hydroxy succimide (0.068 g, 0.588 mmole) and N,N'-dicyclohexylcarbodiimide (DCC) (0.085 g, 0.411 mmole) were dissolved in 1.5 mL of dimethyl formamide (DMF). The reaction mixture was stirred at 37° C. for 1 hr. The precipitated dicyclohexylurea (DCU) was removed by filtration, and the filtrate was treated with 15 mL of ether. Light orange solid was washed three times with 10 mL of ether and dried under vacuum for several hours. The solid obtained was used directly for the next reaction. MALDI-MS (positive mode): 357.1590.

Labeling DNA with indolinium compound: To a 1.5 mL of centrifugation vial containing 20 nmole of DNA was added 41.6 μL of 0.1 M sodium phosphate buffer (NaPi), pH 7.8, 41.6 μL of compound 2 in N-methyl 2-pyrrolidone (NMP) (96 mM) and 41.6 μL of NMP. The vial was placed in a shaker and shaked for 4 hr at 37° C. The reaction mixture was desalted by gel filtration using Sephadex G-25 and then purified by reversed-phase C8 column. Indolinium_EDC2 (DNA: SEQ ID NO: 75): 15% yield. LC-MS (negative mode): Calcd for $C_{163}H_{212}N_{57}O_{90}P_{15}$ (monoisotopic): 1216.7379 [M-5H]$^{-4}$; Found: 1216.9552 [M-5H]$^{4-}$; Indolinium_EDC4 (DNA: SEQ ID NO: 77): 22% yield. LC-MS (negative mode): Calcd for $C_{172}H_{221}N_{60}O_{96}P_{15}$ (monoisotpic): 1280.5002 [M-5H]$^{-4}$; Found: 1280.7356 [M-5H]$^{-4}$; Indolinium_EDC5 (DNA: SEQ ID NO: 78): 15% yield. LC-MS (negative mode): Calcd for $C_{166}H_{220}N_{51}O_{95}P_{15}$ (monoisotpic): 1226.7426 [M-5H]$^{-4}$; Found: 1226.9657 [M-5H]$^{-4}$. Indolinium_antizip5 (DNA: SEQ ID NO: 72): 10% yield. LC-MS (negative mode): Calcd for $C_{307}H_{401}N_{108}O_{180}P_{29}$ (average): 1340.2614 [M-8H]$^{7-}$; Found: 1340.2705 [M-8H]$^{7-}$. Indolinium_antizip5m (DNA: SEQ ID NO 71): 10% yield. LC-MS (negative mode): Calcd for $C_{308}H_{404}N_{109}O_{177}P_{29}$ (monoisotopic): 1336.4969 [M-8H]$^{7-}$; Found: 1336.673 [M-8H]$^{7-}$ Indolinium_antizip3 (DNA: SEQ ID NO: 70): 5% yield. LC-MS (negative mode): Calcd for C307H404N107O178P29 (monoisotopic): 1332.4034 [M-8H]7−; Found: 1332.6293 [M-8H]7−.

Example 2

DNA Conjugated Quaternary Salt

Scheme 4 provides another example of synthesizing DNA conjugated quaternary salt bearing active hydrogen component (benzoindolinium_DNA) following the similar route as indolinium_DNA.

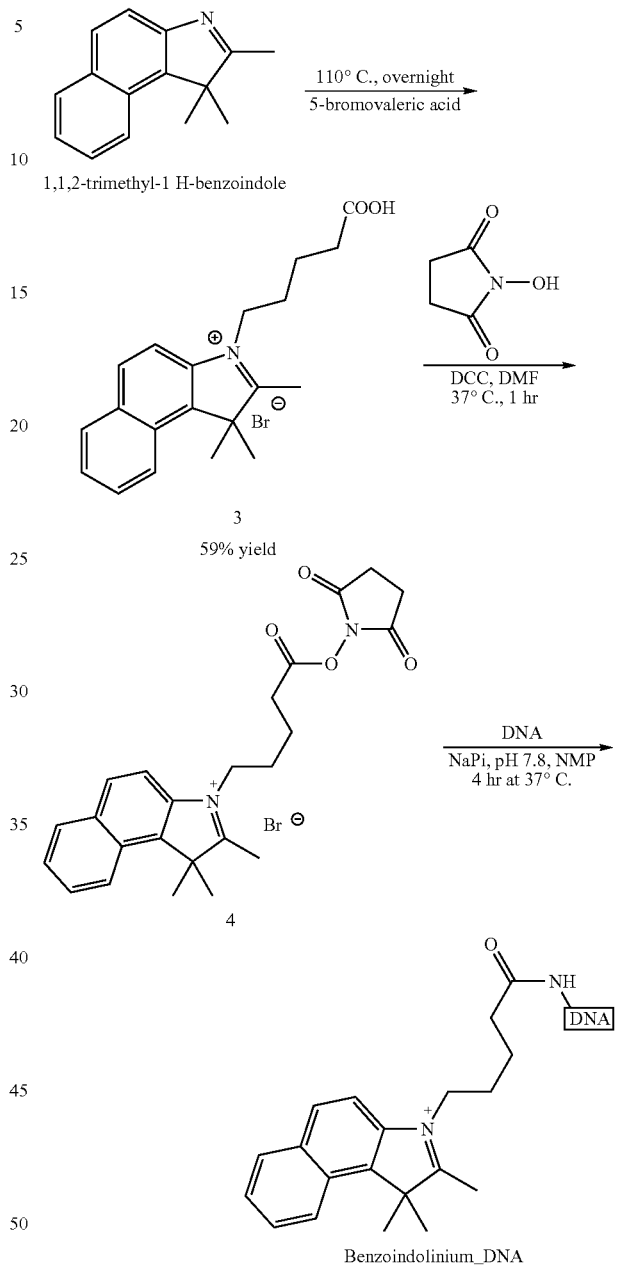

Scheme 4: Example of synthesizing DNA conjugated quaternary salt bearing active hydrogen component (benzoindolinium_DNA).

Synthesis of compound 3: (same procedure of synthesizing compound 1): 1,1,2-trimethyl-1H-benzoindole (2.73 g, 13 mmole) and 5-bromovaleric acid (2.36 g, 13 mmole) was heated with rigorous stirring at 110° C. overnight. Total 3.016 g of 4 was obtained after working up as off-white solid (59% yield). $^1$H NMR (CD$_3$OD) $\delta_{ppm}$: 8.30 (m), 8.15 (m), 8.05 (d), 7.7 (m), 4.66 (t, 2H), 2.45 (t, 2H), 2.1 (m, 2H), 1.85 (m, 2H), 1.85 (s, 3H), 1.83 (s, 6H). MALDI-MS (positive mode): 310.209.

Synthesis of compound 4: Compound 4 was synthesized following the same procedure of synthesizing compound 2 and was used directly for labeling DNA after ether precipitation.

Labeling DNA with benzoindolinium compound: Following the same procedure of synthesizing indolinium_DNA, total 11.2 nmole of Benzoindolinium_EDC7 (DNA: SEQ ID NO: 79) was obtained starting from 50 nmole of EDC7: 22% yield. LC-MS (negative mode): Calculated for $C_{168}H_{216}N_{56}O_{92}P_{15}^{+}$ (monoisotopic): 1650.0003 [M-4H]-3; Found: 1650.0359 [M-4H]3⁻.

Example 3

DNA Conjugated Aldehyde

Scheme 5 provides one example of synthesizing DNA conjugated aldehyde. The acid functionality in aldehyde precursor is introduced through hydrolysis of a cyano group by hydrogen peroxide (Brady, J. D.; Robins, S. P. J. Bio. Chem. 2001, 276, 18812-18818.).

Scheme 5: Example of synthesizing DNA conjugated aldehyde (A0_DNA).

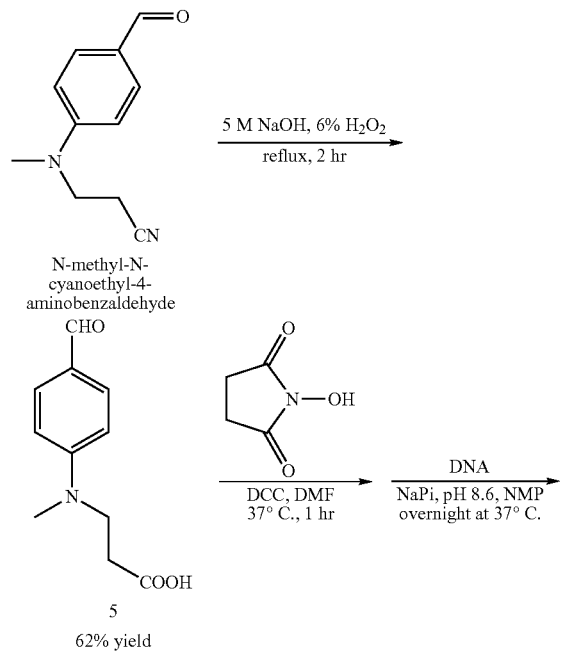

Synthesis of compound 5: In a 50 mL of round-shaped flask containing N-methyl-N-cyanoethyl-4-aminobenzaldehyde (1.024 g, 5.44 mmole) was added 27.2 mL of 5 N NaOH solution and 6.8 mL of 30% $H_2O_2$. The reaction mixture was refluxed for 2 hr. After cooling down, the reaction mixture was neutralized by the addition of concentrated HCl (37% w.t.) and extracted with 2×100 mL of EtOAc and 1×100 mL of $CH_2Cl_2$. The organic layers were combined and washed once with 50 mL of brine and concentrated to dryness. The crude product was purified by a 40 g RediSep silica-gel column on a CombiFlash Companion chromatography system (EtOAc/MeOH). Total 0.702 g of light pinkish solid was obtained (62%). Electrospray MS: M+H 208.0735. (Brady, et al., J. Biol. Chem. 2001, 276, 18812-18818).

Labeling DNA with aldehyde: The NHS ester of 5 was synthesized following the same procedure of compound 2. After removing the DCU by filtration, the filtrate was used directly for DNA conjugation (calculated as 0.2 M product in DMF). To a 1.5 mL of centrifugation vial containing 50 nmole of DNA was added 104 μL of 0.1 M NaPi, pH 8.6, 125 μL of the above filtrate and 83 μL of NMP. The vial was placed in a shaker and shaked overnight at 37° C. The reaction mixture was desalted by gel filtration using Sephadex G-25 and then purified by reversed-phase C8 column. Aldehyde_EDC2 (DNA: SEQ ID NO: 75) (44% yield). LC-MS: Calcd for $C_{158}H_{204}N_{57}O_{91}P_{15}$ (monoisotopic): 1203.9710 [M-4H]$^{-4-}$; 1605.6306 [M-3H]$^{3-}$ Found: 1203.9664 [M-4H]$^{4-}$; 1605.6305 [M-3H]$^{3-}$; Aldehyde_EDC3 (DNA: SEQ ID NO: 76): (49% yield). LC-MS: Calcd for $C_{159}H_{204}N_{59}O_{91}P_{15}$ (monoisotopic): 1213.9725 [M-4H]$^{4-}$; 1618.9660 [M-3H]$^{3-}$ Found: 1213.9620 [M-4H]$^{4-}$; 1618.9590 [M-3H]$^{3}$. Aldehyde_antizip2 reporter1 (DNA: SEQ ID NO: 69) (30% yield). LC-MS: Calcd for $C_{303}H_{396}N_{110}O_{177}P_{29}$ (monoisotopic): 1328.2458 [M-7H]7⁻; Found: 1328.3051 [M-7H]$^{7-}$.

Example 4

DNA Labeled α,β-unsaturated Aldehyde

Scheme 6 provides an example of synthesizing DNA labeled α,β-unsaturated aldehyde 1. Wittig reagent was used for the two-carbon homologation of aldehydes into the corresponding α,β-enals (Eitel, M.; Pindur, U. Synthesis 1989, 364-367. The acid functionality in aldehyde precursor is introduced through hydrolysis of a cyano group by concentrated HCl (Bratenko, M. K.; Chomous, V. A.; Vovk, M. V. Chemistry of Heterocyclic Compounds 2004, 40, 1279-1282).

Scheme 6: Example of synthesizing DNA conjugated aldehyde (A1_DNA).

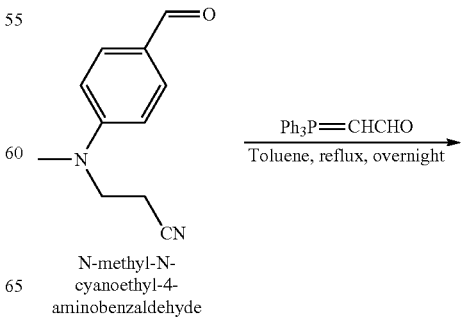

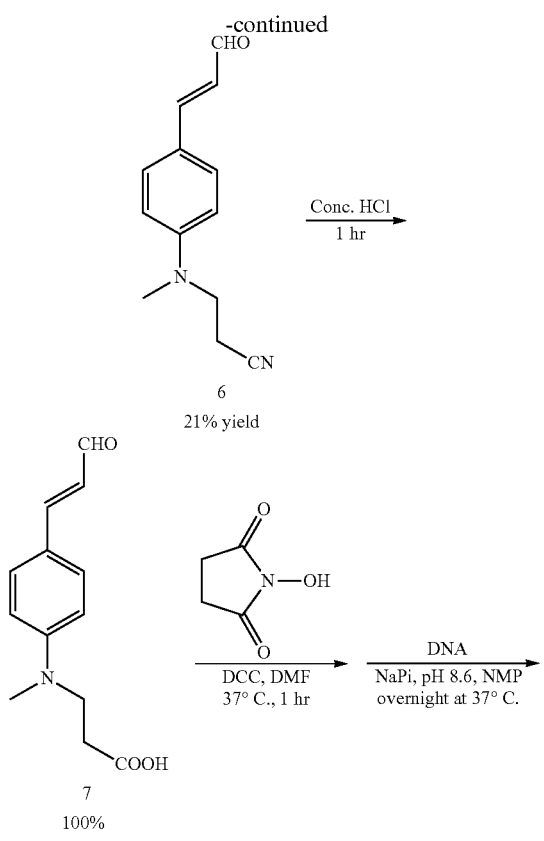

removing most of the HCl, the compound was dissolved in water and lyophilized to dryness to afford the product.

Labeling DNA with α,β-unsaturated aldehyde: The NHS ester of compound 7 was synthesized following the same procedure as compound 2, however was purified by silica-gel chromatography (EtOAc/Hexanes) instead. After drying under vacuum for several hours, the NHS ester of compound 7 was dissolved in NMP (96 mM) and was used to label DNA following the same procedure as labeling aldehyde_DNA. Aldehyde1_EDC8 (DNA: SEQ ID NO: 80): yield 46%. Calcd for $C_{163}H_{215}N_{48}O_{99}P_{15}$ (monoisotopic): 1629.9698 $[M-3H]^{-3}$; Found: 1629.9995 $[M-3H]3^-$. Aldehyde1_antizip2 reporter1 (DNA: SEQ ID NO: 69): yield 40%. Calcd for $C_{305}H_{398}N_{110}O_{177}P_{29}$ (monoisotopic): 1331.96239 $[M-7H]^7$; Found: 1332.0778 $[M-7H]^{-7}$.

Example 5 to 8 are related to the preparation of indole and indolinium analogues for DNA conjugation.

Indole analogues can be synthesized following the general Fischer-indole synthesis by converting aryl hydrazones to indoles under acidic conditions (Scheme 7). First, a primary aromatic amine and nitrous acid reacts to give a diazonium salt. The diazonium salt is then reduced to a hydrazine (Hunsberger et. al. *J. Org. Chem.* 1956, 21, 394-399). Finally hydrazine reacts with 3-methylbutan-2-one to form the aryl hydrazone which upon isomerization and elimination of $NH_3$ forms indole (Lindsey et. al. *Tetrahedron* 1989, 45, 4845-4866).

Scheme 7: General synthetic routes to the indole and indolinium analogues.

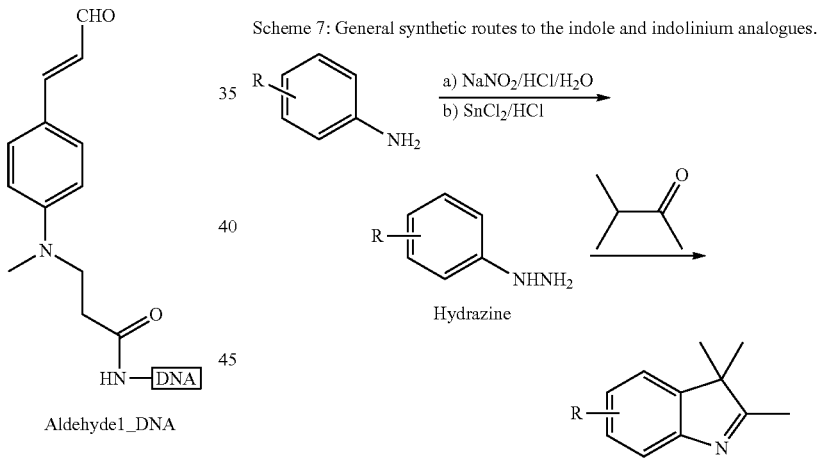

Synthesis of compound 6: In a 100 mL of round-shaped flask containing N-methyl-N-cyanoethyl-4-aminobenzaldehyde (1.116 g, 5.9 mmole) and ylide (2.71 g, 8.9 mmole) was added 57 mL of dry toluene. The reaction mixture is heated under reflux for overnight, allowed to cool, and filtered through filter paper. After removing the solvent from the filtrate, the residue was first purified by a 40 g RediSep silica-gel column on a CombiFlash Companion chromatography system (Toluene/Ether) and then Preparative HPLC C18 column (Agilent Prep-C18, 30×100 mm, 10 um) to afford 0.27 g of pure product (21%). MALDI-MS (positive mode): 215.226.

Synthesis of compound 7: In a 50 mL of round-shaped flask containing compound 6 (0.1 g, 0.47 mmole) was added 30 mL of concentrated HCl. The reaction mixture was heating to boiling and left at room temperature (RT) for 1 hr. HPLC analysis indicated that only one product was formed and no starting material remained in the reaction mixture. After Examples:

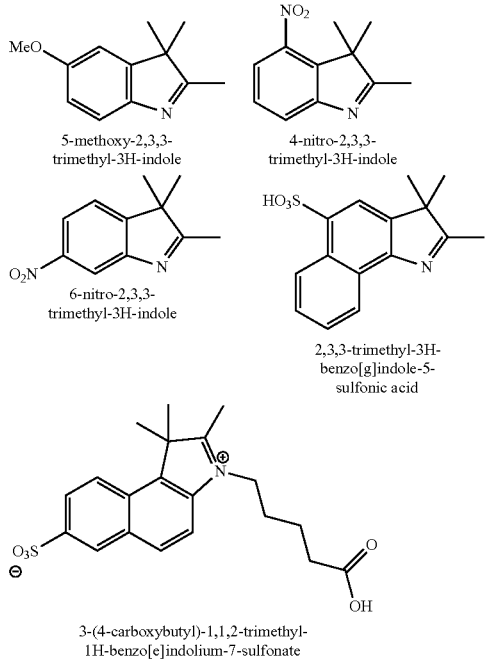

5-methoxy-2,3,3-trimethyl-3H-indole 4-nitro-2,3,3-trimethyl-3H-indole 6-nitro-2,3,3-trimethyl-3H-indole 2,3,3-trimethyl-3H-benzo[g]indole-5-sulfonic acid 3-(4-carboxybutyl)-1,1,2-trimethyl-1H-benzo[e]indolium-7-sulfonate Example 5

Synthesis of 5-methoxy-2,3,3-trimethyl-3H-indole

To a solution of 4-methoxyaniline (2.46 g, 20 mmol) in 60 mL of conc. HCl was added dropwise the solution of $NaNO_2$ (1.38 g, 20 mmol) in 35 mL of $H_2O$ at 0° C. After stirring for 0.5 h at 0° C., the reaction mixture was added dropwise to a solution of $SnCl_2$ (9.03 g, 40 mmol) in 35 mL of conc. HCl at 0° C., then stirring was continued for 1.5 h at 0° C. 2N NaOH was then added to quench the reaction until pH=9 to 10. The aqueous layer was extracted with DCM (50 mL×3) and the organic layer was dried over $Na_2SO_4$. After filtration and concentration, the desired product, (4-methoxyphenyl)hydrazine was obtained (0.98 g, 35% yield), which was used directly for next step.

A mixture of (4-methoxyphenyl)hydrazine (0.98 g, 7.1 mmol) and 3-methylbutan-2-one (1.53 g, 17.8 mmol) in 20 mL of HOAc was heated at 100° C. overnight. The mixture was concentrated and 1N NaOH was added until pH 9 to 10. The aqueous solution was extracted with ethyl acetate (50 mL×3). The combined organic layers were dried over $Na_2SO_4$. After filtration and concentration, the residue was purified by flash column chromatography to give 610 mg of 5-methoxy-2,3,3-trimethyl-3H-indole (45%). $^1$H NMR ($CDCl_3$) $\delta_{ppm}$: 7.43 (dd, 1H), 6.81 (m, 2H), 3.83 (s, 3H), 2.26 (s, 3H), 1.28 (s, 6H). LC-MS (M+H): 190.16

Example 6

Synthesis of 4(6)-nitro-2,3,3-trimethyl-3H-indole (3-nitrophenyl)hydrazine (MW=189.6, 685 mg, 3.6 mmol) and 0.75 ml 3-methyl-2-butanone were stirred in 8 mL of EtOH at RT for 10 minutes, then at 40° C. for 15 minutes. Ethanol was removed under reduced pressure. The residue was taken up in 20 mL of conc. HCl and heated at 100° C. for 2 h. The aq. HCl was then removed under reduced pressure. The solid was triturated with 2 mL of iced water, filtered and washed with 2 mL of iced water. After drying in the air, the solid weighed 300 mg. However, TLC indicated that it contained a mixture of two products. The aqueous layers were neutralized with 1N NaOH to pH~8.0, extracted with EtOAc (50 mL×3). The organic layers and the solid obtained previously were combined, dried over $Na_2SO_4$ overnight. The organic solution was filtered, washed with EtOAc, and concentrated under reduced pressure. The residue was purified by flash chromatography ($SiO_2$, 70 g), eluted with 8-15% EtOAc in hexane to give two fractions. The first fraction was obtained in 217 mg (30% yield) as a light yellow oil, which was identified as compound 4-nitro-2,3,3-trimethyl-3H-indole by $^1$H NMR. $^1$H NMR ($CDCl_3$) $\delta_{ppm}$: 8.0 (dd, 1H), 7.89 (dd, 1H), 7.50 (t, 1H), 2.73 (s, 3H), 1.50 (s, 6H). The second fraction was obtained in 245 mg (33% yield) as a yellow solid, which was identified as 6-nitro-2,3,3-trimethyl-3H-inodle by $^1$H NMR. $^1$H NMR ($CDCl_3$) $\delta_{ppm}$: 8.33 (d, 1H), 8.12 (dd, 1H), 7.50 (t, 1H), 7.38 (d, 1H), 2.33 (s, 3H), 1.27 (s, 6H).

Example 7

Synthesis of 2,3,3-trimethyl-3H-benzo[g]indole-5-sulfonic acid

A solution of sodium 4-aminonaphthalene-1-sulfonate (2.45 g, 10 mmol) in $H_2O$ (15 mL) was added a solution of $NaNO_2$ (0.70 g, 10 mmol) in $H_2O$ (2 mL) at 10-15° C. The solution was then added to a cold solution of conc. $H_2SO_4$ (0.54 g, 5.5 mmol) in 0.5 mL of $H_2O$. The temperature was maintained below 10° C. and the mixture was stirred for 1.5 h after the addition was complete. The mixture was then added dropwise to a cold solution of SnCl2 (3.8 g, 17 mmol) in 2.5 mL of conc. HCl and 1.5 ml of $H_2O$. The reaction temperature was kept below 10° C. and allowed to sit onemoght. It was filtered and washed thoroughly with $H_2O$. The cake was removed twice from the Buchner funnel and suspended in $H_2O$ and filtered. The solid obtained was dried under vacuum to give 1.4 g of 4-hydrazinylnaphthalene-1-sulfonic acid (59%). The material was used directly for next step. A solution of 4-hydrazinylnaphthalene-1-sulfonic acid (0.7 g, 2.9 mmol) in 3 ml of HOAc was added 3-methylbutan-2-one (0.5 ml, 1.5 eq), NaOAc (0.47 g, 2.0 eq.). The mixture was stirred at 110° C. for 3.5 h. After cooling and addition of ether, the precipitate was filtered to give 700 mg. The solid was dissolved in DCM and purified by flash chromatography on $SiO_2$ using 10% MeOH in DCM to give 273 mg of product. The mother liquor was concentrated and was also purified by flash chromatography on silica gel to give additional 372 mg of product. The overall yield was 77%. $^1$H NMR (DMSO) $\delta_{ppm}$: 8.8 (dd, 1H), 8.4 (dd, 1H), 8.0 (s, 1H), 7.5 (m, 2H), 3.1 (s, 5H), 2.3 (s, 4H), 1.3 (s, 6H). LC-MS: 288.2 [M−H].

Example 8

Synthesis of 3-(4-carboxybutyl)-1,1,2-trimethyl-1H-benzo[e]indolium-7-sulfonate

To a solution of 6-aminonaphthalene-2-sulfonic acid (2.23 g, 10 mmol) in 15 ml of $H_2O$ was added 2N NaOH (0.75 ml). The mixture was stirred for 5 min at RT and conc. $H_2SO_4$ (0.68 g, 6.9 mmol) was added to it dropwise at 0° C. 2 ml of iced $H_2O$ was added, followed by a solution of $NaNO_2$ (1.04 g, 15 mmol) in 2 ml of H2O. After the solution was stirred at 0° C. for 2 h, the diazonium salt was removed by filtration and washed with cold water. The salt was then added in portions to a cold (<0° C.) solution of SnCl2 (4.9 g, 22 mmol) in 3.2 ml of conc. HCl and 1.8 ml of $H_2O$. The mixture was stirred overnight. The solid was filtered and washed twice with water, dried under vacuum to give 1.84 g of 6-hydrazinylnaphthalene-2-sulfonic acid (77%), which was used directly for next step.

To a solution of 6-hydrazinylnaphthalene-2-sulfonic acid (0.7 g, 2.9 mmol) in 3 ml of HOAc was added 3-methylbutan-2-one (0.5 ml, 1.5 eq), NaOAc (0.47 g, 2.0 eq.). The mixture was stirred at 110° C. for 3.5 h. After cooling, the solvent was removed under reduced pressure. The residue was dissolved in MeOH and 3.0 g of $SiO_2$ was added. MeOH was removed and the silica gel was loaded on a silica gel column and eluted with 10% MeOH in DCM to give the desired product, 1,1,2-trimethyl-1H-benzo[e]indole-7-sulfonic acid (874 mg, >95% yield). LC-MS: 288.2 [M−H]

To a solution of 1,1,2-trimethyl-1H-benzo[e]indole-7-sulfonic acid (723 mg, 2.5 mmol) in methanol (5 mL) was added a saturated solution of potassium hydroxide in isopropanol (3.134%, 4.913 g, 1.1 eq.) and the resulting suspension was heated at reflux for 2 h. Then the mixture was concentrated and the corresponding potassium salt was obtained. Under nitrogen atmosphere, a mixture of potassium 1,1,2-trimethyl-1H-benzo[e]indole-7-sulfonate and 5-bromovaleric acid (585 mg, 3 mmol) in 3-methyl-2-butanone (5 mL) was heated at 140° C. for 20 h. Removal of the solvent and purification by chromatography (dichloromethane/methanol) afforded 3-(4-carboxybutyl)-1,1,2-trimethyl-1H-benzo[e]indolium-7-sulfonate (70 mg, isolated yield 7.2%). LC-MS: 390.18 [M+].

Example 9

Organocatalyzed Hemicyanine Synthesis in Aqueous Buffer

Scheme 8 provides an example of synthesizing hemicyaine 8 in aqueous buffer in the presence of various catalysts. The extent of hemicyanine formation was easily monitored by analytical reversed-phase HPLC (UV at 545 nm). Hemicyanine 8 has fluorescence excitation wavelength maximum at 535 nm and emission maximum at 580 nm. MALDI-MS analysis of the product confirms the structure (M+: 449.1992). The experimental data indicates (S)-pyrrolidinemethylpyrrolidine ((S)-PMP) has better catalytical ability than other catalysts.

Scheme 8: Hemicyanine formation in aqueous buffer in the presence of catalysts

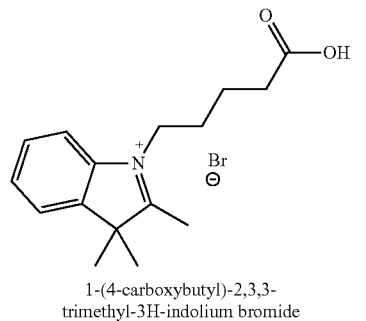

1-(4-carboxybutyl)-2,3,3-trimethyl-3H-indolium bromide

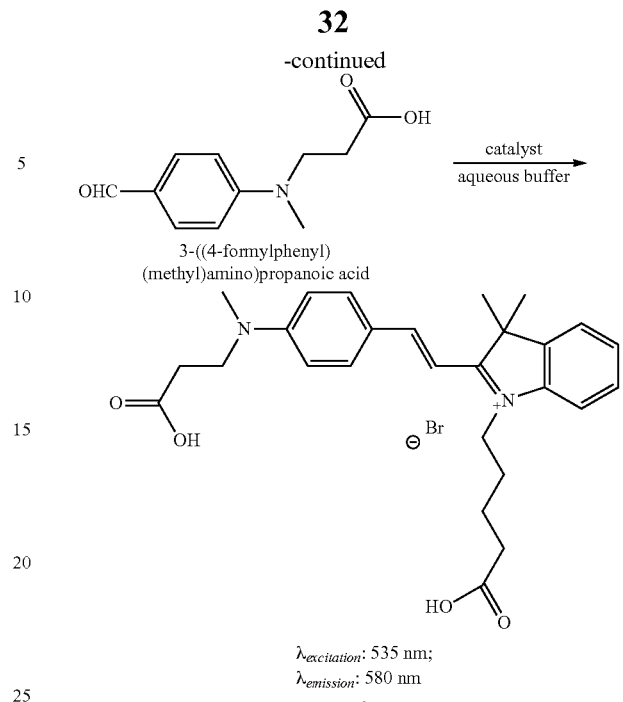

3-((4-formylphenyl)(methyl)amino)propanoic acid $\lambda_{excitation}$: 535 nm;
$\lambda_{emission}$: 580 nm

8

Catalysts:
(1) L-valine (0.3 equiv. water); (2) L-proline (0.3 equiv. water);
3) (S)-Pyrrolidinemethylpyrrolidine (0.3 equiv. 50 mM sodium phsphate buffer; pH 8.5); (4) (S)-2-pyrrolidinemethanol (0.3 equiv. watr); (5) Zinc-proline or Zn(Pro)2 (0.1 equiv. 20 M sodium phosphate buffer, pH 8.5);
(6) Pyrroldine/acetic acid (0.4/0.2 equv. waer); (7) Pyrrolidine/10-camphorsulfonic acid (0.4/0.2, watr)
Reaction condions: 25 mM each of the starting material, 20% NMP in water or sodium phosphate buffer plus required catalysts, RT for 16 hr.

Examples 10-13 are related to DPC of hemicyanine formation.

Example 10

DPC Hemicyanine Formation (End of Helix Architect)

Scheme 9 gives an example of DPC hemicyanine formation through end of helix architecture. Upon annealing, the two hemicyanine precursors were placed in reactive proximity at the end of helix and a hemicyanine linked to both DNA was formed after condensation.

Scheme 9: Example of synthesizing hemicyanine_DNA dye 1 through DPC (end of helix).

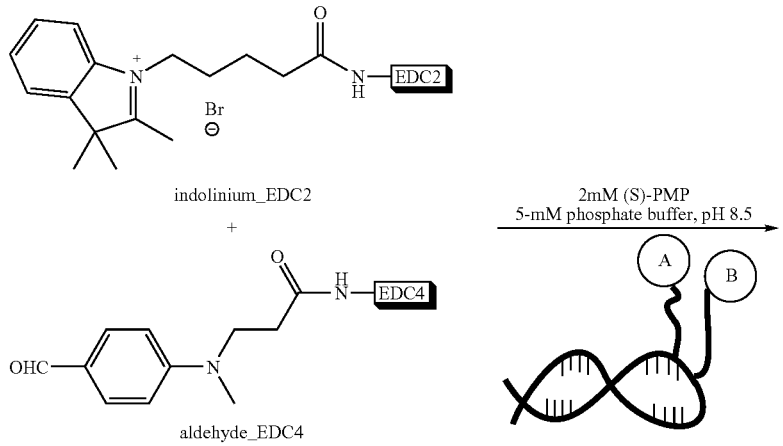

-continued

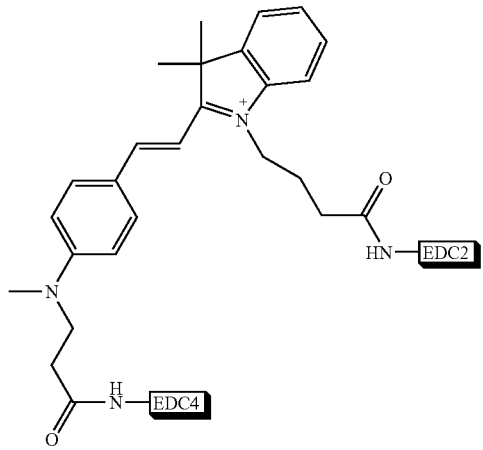

| Name | Sequence (5'-3') |
|------|------------------|
| EDC2 | H2N-AGCTC CAACT ACCAC(SEQ ID NO: 75) |
| EDC4 | GTGGT AGTTG GAGCT-NH2 (SEQ ID NO: 77) |
| EDC3 | H2N-AGATC CCACT AGCAC (mismatch) (SEQ ID NO: 76) |

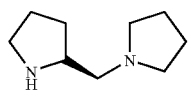

(S)-1-(2-pyrrolidnylmethyl)-pyrrolidine (PMP)

Figure 20A:
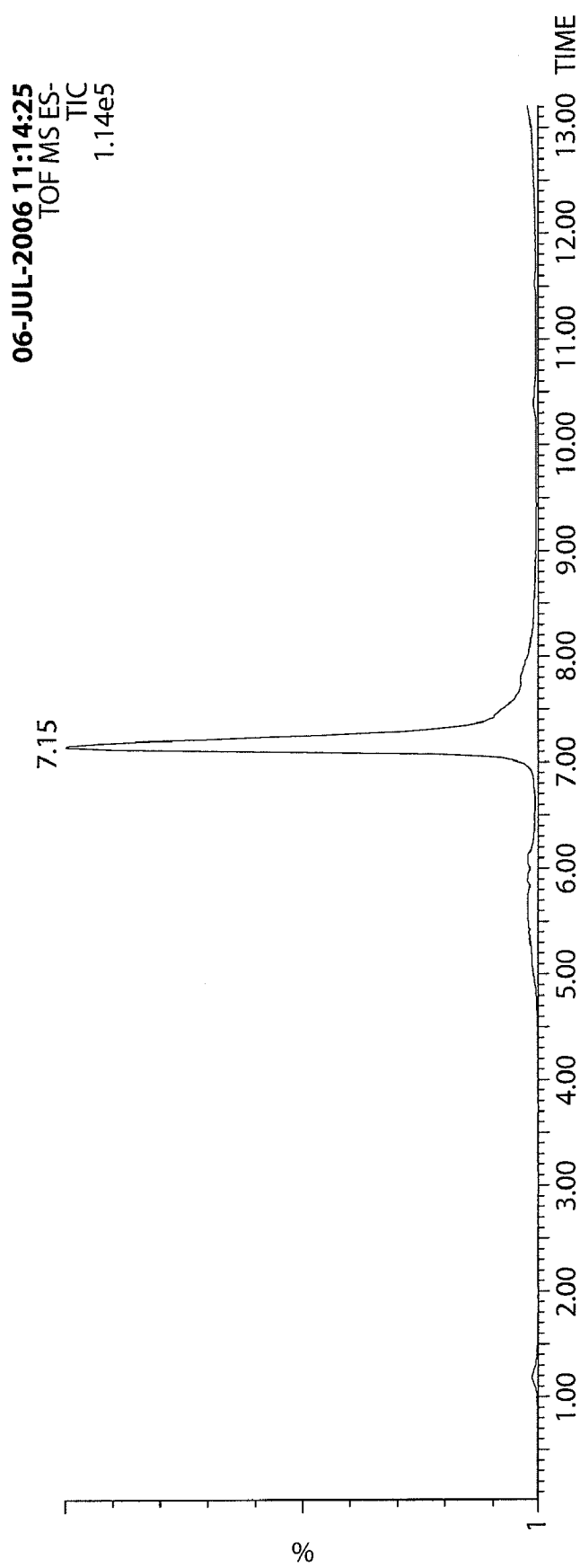
FIG. 20A shows LC-MS chromatograph data of a DPC reaction product.
Figure 20B:
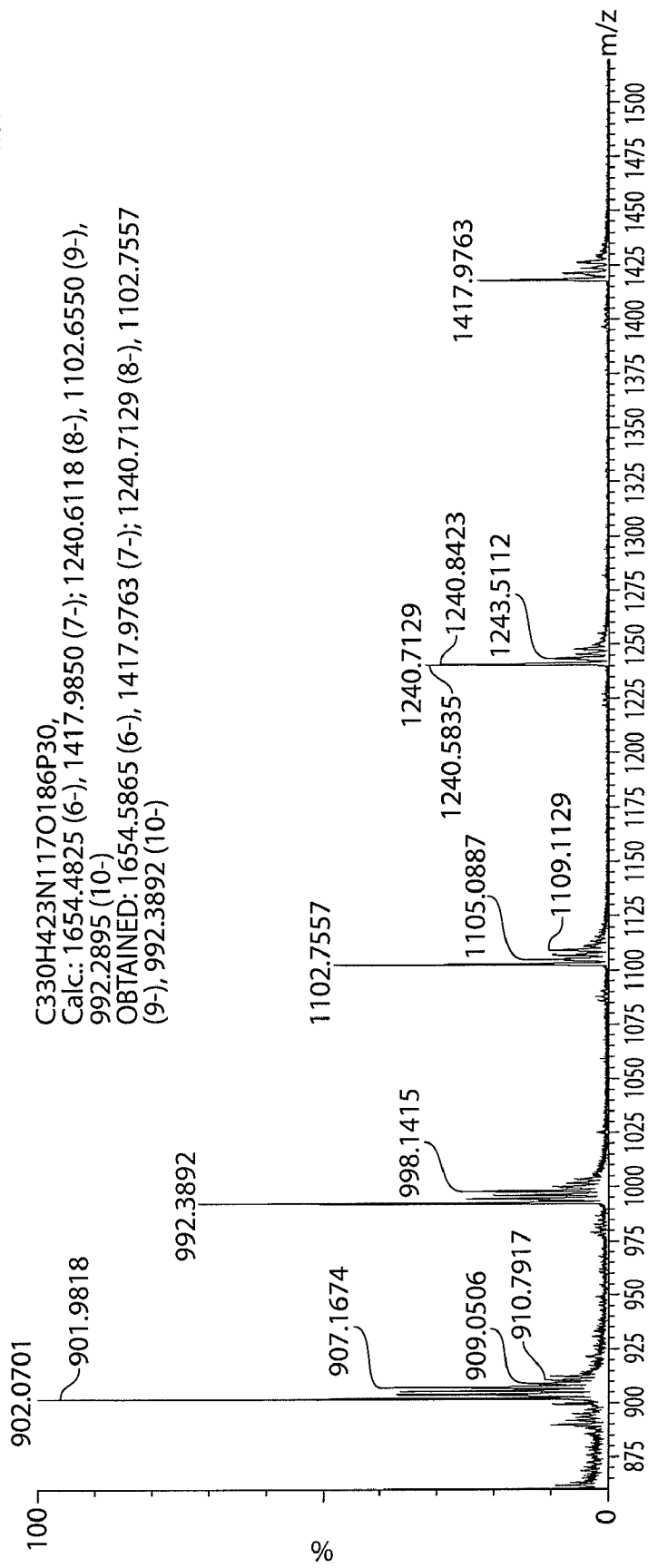
FIG. 20B shows the mass spectrum of a DPC reaction product.

The progress of DPC reaction was monitored by fluorescence spectroscopy. FIG. 17 shows the fluorescence emission of DPC reaction mixture of indolinium and aldehyde DNA (I_EDC2 and A_EDC4) (DNA: SEQ ID NO: 75; SEQ ID NO: 77) at various conditions. First, there is no background fluorescence emission for hemicyanine precursor I_EDC2 (DNA: SEQ ID NO: 75) and A_EDC4 alone in the reaction buffer (2 & 3 in FIG. 17). Second, the DPC reaction is catalyst dependent and not pH dependent. Without the addition of (S)-PMP, there is no fluorescence signal. Simply increasing the pH of the reaction conditions from pH 8.4 to 10.0 did not generate any signal (5 & 6 in FIG. 17). Finally, DPC reaction is Watson-Crick sequence-specific (nucleic acid dependent). By switching EDC4 with three mismatched nucleobases DNA (EDC3, DNA: SEQ ID NO: 76), no fluorescence signal was generated after 140 minutes. Only trace amount of fluorescence signal detected after 16 hr (FIG. 18). After 16 hr, LC-MS shows almost 90% conversion of the product for reaction 1 (FIG. 19). FIG. 20 gives the electrospray mass data of purified DPC product (EDC4_H_EDC2) (DNA: SEQ ID NO: 77; SEQ ID NO: 75) which confirms the structure. The relative quantum yield measured for EDC2_H_EDC4 (DNA: SEQ ID NO: 75; SEQ ID NO: 77) is around 0.1 in water using sulforhodamine 101 as fluorescence standard. The extinction coefficient of EDC2_H_EDC4 (DNA: SEQ ID NO: 75; SEQ ID NO: 77) at 550 nm is around 87000 in water.

DPC reaction: Reactions were performed with 200 nM each of reagent in 10 mM (S)-PMP, 50 mM sodium phosphate buffer, pH 8.4, 1 M NaCl at RT unless otherwise specified. Catalyst (S)-PMP was added after mixing both reagents together in reaction buffer.

Example 11

DPC Hemicyanine Formation (Middle of Helix Architect)

Figure 22A:
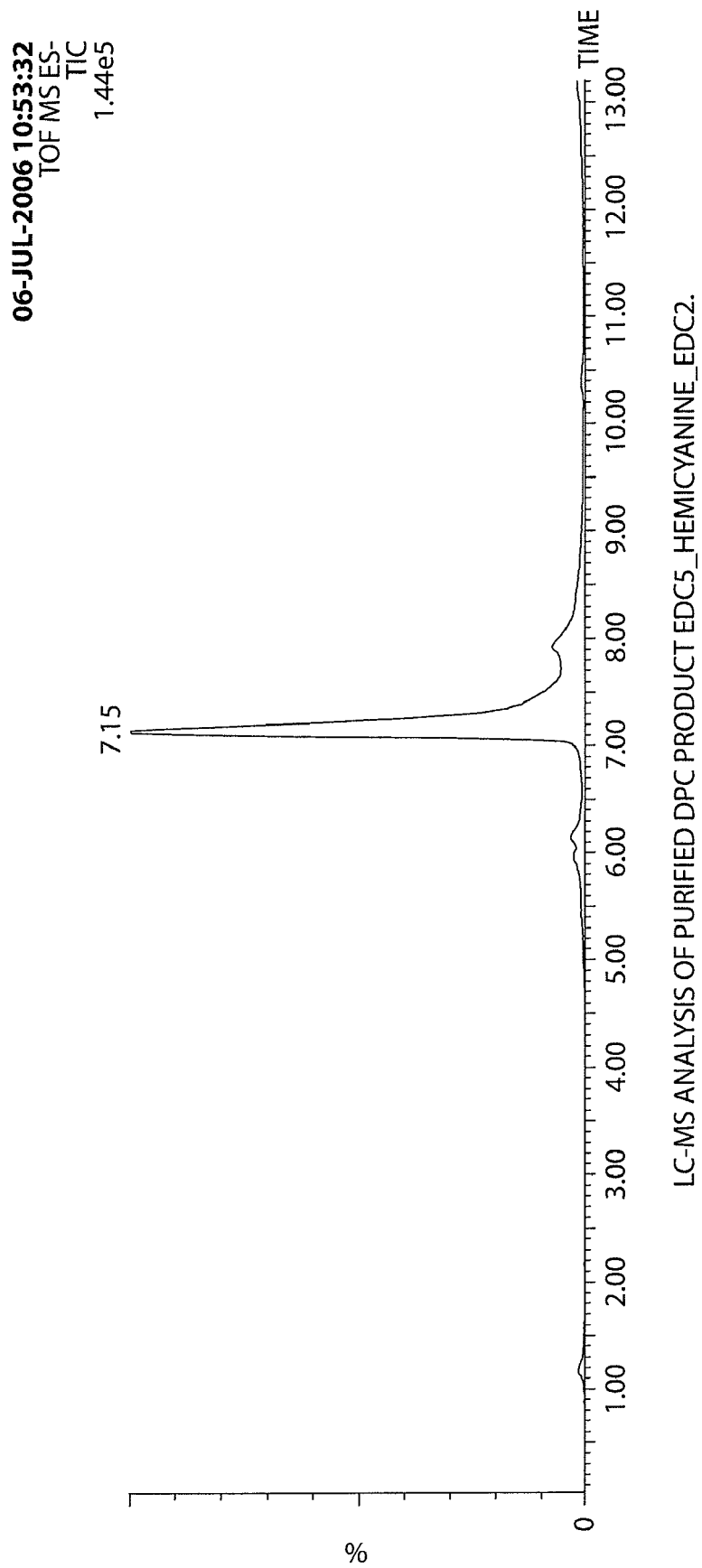
FIG. 22A shows LC-MS chromatograph data of a DPC reaction product.
Figure 22B:
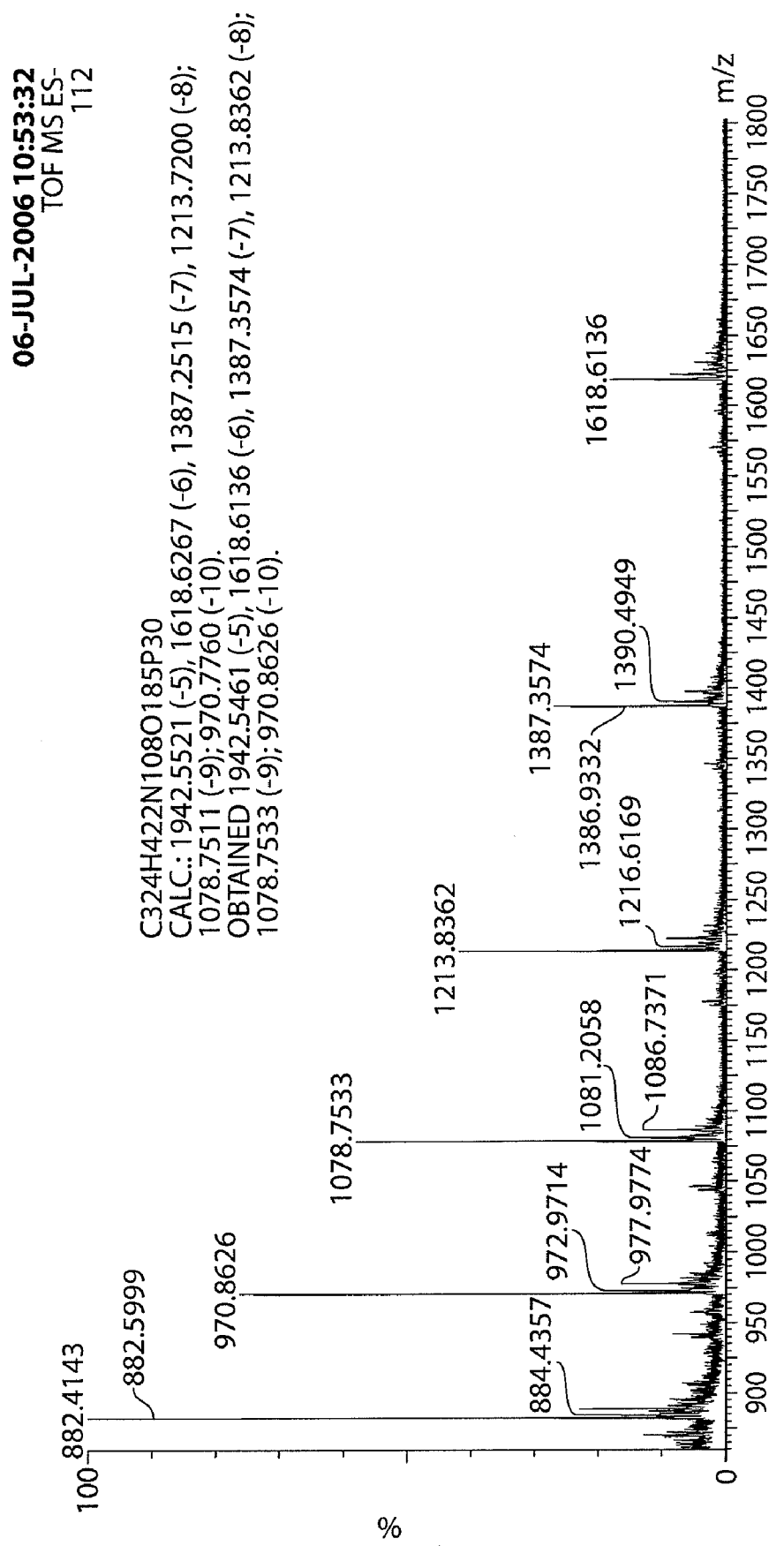
FIG. 22B shows the mass spectrum of a DPC reaction product.

Scheme 10 provides another example of DPC hemicyanine formation through middle of helix architecture where the reactants were labeled to two probes which can complementary with a single template. Upon annealing, the two hemicyanine precursors were placed in reactive proximity at the middle of helix and a hemicyanine linked to both DNA was formed. The experimental data indicate only in the presence of the template, fluorescence signal is generated (FIG. 21). EDC2_H_EDC5 (DNA: SEQ ID NO: 75; SEQ ID NO: 78) was purified and its structure was confirmed by mass data (FIG. 22). The relative quantum yield measured for EDC2_H_EDC5 (DNA: SEQ ID NO: 75; SEQ ID NO: 78) alone is similar to EDC2_H_EDC4 (DNA: SEQ ID NO: 75; SEQ ID NO: 77) (0.1 in water). The extinction coefficient of EDC2_H_EDC5 (DNA: SEQ ID NO: 75; SEQ ID NO: 78) at 550 nm is around 75000 in water.

Scheme 10: Example of synthesizing hemicyanine_DNA dye 2 through DPC (middle of helix).

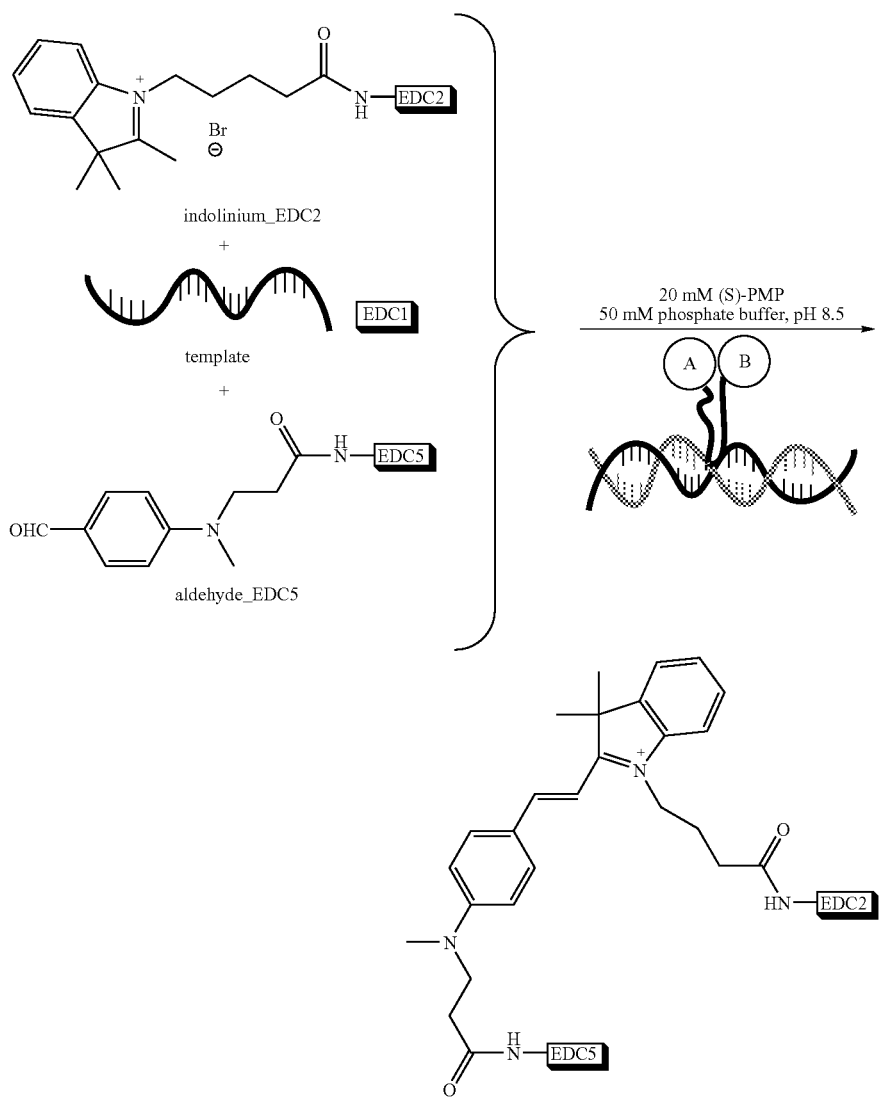

Name Sequence (5'-3')
EDC1 GTGGT AGTTG GAGCT GGTGG CGTAG GCAAG A (SEQ ID NO: 74)
EDC2 H₂N-AGCTC CAACT ACCAC (SEQ ID NO: 75)
EDC5 TCTTG CCTAC GCCAC-NH₂ (SEQ ID NO: 78)

DPC reaction: Reactions were performed with 200 nM each of indolinium_EDC5 (DNA: SEQ ID NO: 78), aldehyde_EDC5 (DNA: SEQ ID NO: 78), EDC1 (DNA: SEQ ID NO: 74) in 10 mM (R) —PMP, 50 mM sodium phosphate buffer, pH 8.4, 1M NaCl at RT. (S)-PMP was added after mixing both reagents and template together in the reaction buffer.

Example 12

Kinetic Studies of Hemicyanine DPC

The reaction rate for both end-of-helix (Example 10) and middle-of-helix (Example 11) DPC were investigated by fluorescence spectroscopy (FIG. 23 and FIG. 24). The kinetic profiles for both reactions are very similar. After around 16 hr, the fluorescence signal reached plateau which indicated the completion of the reaction.

Example 13

Generation of Four Fluorescent Hemicyanine Dyes Via Middle-of-helix DPC

FIG. 3 gives an example of four-plex hemicyanine_DNA dyes that can be generated through DPC. In this example, total two quaternary salt precursors (indolinium I and benzoindolinium BI) and two aldehydes (A0, A1) are needed to generate four DNA hemicyanine dyes. These precursors share the structural similarity, thus DPC conditions for quaternary salt and aldehyde should be similar. According to literature data, benzoindolinium compound generally gives 20 nm of red shift while one extra double bond conjugation shifts the fluorescence emission wavelength towards to visible range (~80 nm for hemicyanine dye). FIG. 3 lists the spectroscopic properties of these four hemicyaine_DNA dyes.

Small molecule hemicyanine dyes (9 to 12) were first synthesized and their fluorescence excitation and emission spectra were recorded (FIG. 25). As predicted, one extra phenyl substitution shifted the fluorescence emission 20 nm to the red (compound 9 and 10), while each additional vinyl group in the polyene chain shifted around 80 nm (9 and 11; 10 and 12). To maximize the utility of the DNA codons and simplify the DNA probe preparation, only two DNA strands was used to label I and BI and two DNA strands for aldehydes with four template strands (FIG. 26). Each template had two unique codons that can only Watson-Crick base pair with one set of aldehyde and quaternary salt precursor to generate one hemicyanine dye. The DPC was performed in a combinatory fashion in one-pot. FIG. 27 shows normalized fluorescence emission spectra of four individual DPC reactions between indolinium/aldehyde (a) and benzoindolinium/aldehyde (b), indolinium/α,β-unsaturated aldehyde 1 (c) and benzoindolinium/α,β-unsaturated aldehyde 1 (d) using above mentioned DNA codon (FIG. 26). Four colors were generated from these DPC reactions. Similar to the fluorescence data from small molecule hemicyanine dyes (FIG. 25), around 15 nm of fluorescence emission wavelength difference was observed for one extra phenyl substitution (compound 13 and 14, 15 and 16). One additional vinyl group in the polyene chain shifted around 80 nm of fluorescence emission wavelength (compound 13 and 15, 14 and 16).

DPC reaction: Reactions were performed with 200 nM each of strands and template in 10 mM N,N-dimethyl ethylenediamine (DMEDA), 50 mM sodium phosphate buffer, pH 8.4, 150 mM NaCl at RT. Catalyst was added after mixing both reagents and template together in the reaction buffer.

Example 15

Generation of Two Fluorescent Hemicyanine Dyes Via End of Helix DPC

Two hemicyanine products were formed by mixing antizip3_indolinium with antizip2 reporter1_A0 and antizip2 reporter1_A1 respectively (DNA: SEQ ID NO: 69). The product (17) formed between antizip3_indolinium (DNA: SEQ ID NO: 70) and antizip2 reporter1_A0 (DNA: SEQ ID NO: 69) has excitation maximum at 540 nm and emission maximum at 600 nm, while the product (18) formed between antizip3_indolinium (DNA: SEQ ID NO: 70) and antizip2 reporter1_A1 (DNA: SEQ ID NO: 69) had excitation maximum at 600 nm and emission maximum at 670 nm (FIG. 28).

DPC reaction: Reactions were performed with 200 nM each of reagent in 15 mM DMEDA, 50 mM sodium phosphate buffer, pH 8.0, 2.5 mM MgCl2 at 30° C. Total reaction volume was 50 μL. Catalyst DMEDA was added after mixing both reagents together in reaction buffer. Fluorescence was recorded immediately after the addition of catalyst DMEDA. General Examples on Dpc-Based Protein Detection Example 16

Creation of Fluorescence by Hybridization Induced Azidocoumarin Reduction

Five oligonucleotides were prepared using standard phosphoramidite chemistry (Glen Research, Sterling Va., USA). Oligonucleotides bearing 5'-amino groups (Oligo2 and Oligo6) were prepared using 5'-Amino-Modifier 5 and Oligonucleotides bearing 3'-aminogroups (Oligo4 and Oligo5) were prepared using 3'-Amino-Modifier C7 CPG (Glen Research, Sterling Va., USA)

```
                                          (SEQ. ID. NO. 19)
Oligo1    5'-GTGGTAGTTGGAGCTGGTGGCGTAGGCAAGA-3'

(SEQ. ID. NO. 20)
Oligo2    5'-H2N-AGCTCCAACTACCAC-3'

(SEQ. ID. NO. 21)
Oligo4    5'-GTGGTAGTTGGAGCT-NH2-3'

(SEQ. ID. NO. 22)
Oligo5    5'-TCTTGCCTACGCCAC-NH2-3'

(SEQ. ID. NO. 23)
Oligo6    5'-H2N-AGATCCCACTAGCAC-3'
```

Oligo1, Oligo4 and Oligo5 were removed from the synthesis support and purified by reversed-phase HPLC. The amino groups of Oligo2 and Oligo6 were converted while resin-bound to their triphenyl phosphine derivatives and these were purified and isolated (Sakurai et al., J. Amer. Chem. Soc., 2005, 127, pp 1660-1667) to give Oligo2-TPP and Oligo-6TPP, respectively.

Amino group bearing Oligo4 and Oligo5 were converted to their azidocoumarin derivatives (Oligo-4-AzC and Oligo5-AzC, respectively) by reaction of each oligo with the N-hydroxysuccinimide ester of 7-azido-4-methylcoumarin-3-acetic acid (Thevenin et al., Eur. J. Biochem (1992) Vol. 206, pp-471-477). The reaction was performed by adding 1 μL of trifluoroacetic acid to 5 μL of N-methylmorpholine to prepare a buffer to which was added 10 μL of water containing 6.6 nmol of Oligo 4 or Oligo 5, followed by addition of 30 μL of a 0.16 M solution of the coumarin NHS-ester in dimethylformamide. Each reaction was allowed to proceed for 2 hours at room temperature, whereupon 50 μL of 0.1 M aqueous triethylammonium acetate was added. The mixtures were applied to a NAP-5 desalting columns (Amersham Biosciences, Piscataway N.J. USA) and eluted according to the manufacturers instructions the eluate was purified by RP-HPLC to provide Oligo-4-AzC and Oligo5-AzC, in yields of 77% and 70%, respectively. Product identity was confirmed by Maldi-ToF mass spectrometry.

To demonstrate the hybridization-specific creation of fluorescence, various combinations of complementary and non-complementary oligonucleotides bearing azido-coumarin and triphenyl phosphine moieties were allowed to react at room temperature in a buffer comprised of 30% aqueous formamide, 50 mM NaCl, and 10 mM sodium phosphate, pH 7.2. The reaction progress was monitored over time using a Victor Multilabel fluorimeter (EG&G Wallach, Turku Finland) set to excite the sample at 360 nm and monitor light emission at 455 nm FIG. 29 shows that when Oligo-4-AzC and Oligo2-TPP are combined to final concentrations of 200 nM and 400 nM respectively, a rapid increase in fluorescence is observed. In this figure 004 denotes Oligo-4-AzC, 002 denote Oligo2-TPP, and 006 denotes Oligo6-TPP. The fluorescence does not occur when Oligo6-TPP is substituted for Oligo2-TPP. Whereas Oligo2-TPP is perfectly complementary in its base-pairing ability to Oligo-4-AzC, Oligo6-TPP is not, as it contains three mismatched nucleotides. The results support the conclusion that the creation of fluorescence is due to the ability of Oligo2-TPP to hybridize to Oligo-4-AzC thus facilitating a reaction between the TPP and azidocoumarin moieties in the resulting hybrid. The lack of signal in the case of reaction of Oligo6-TPP with Oligo-4-AzC is consistent with inability of these two oligonucleotides to form a duplex, therefore the reaction is not facilitated. Control reactions containing each single oligonucleotide were performed to rule out any non-specific effects.

Figure 30:
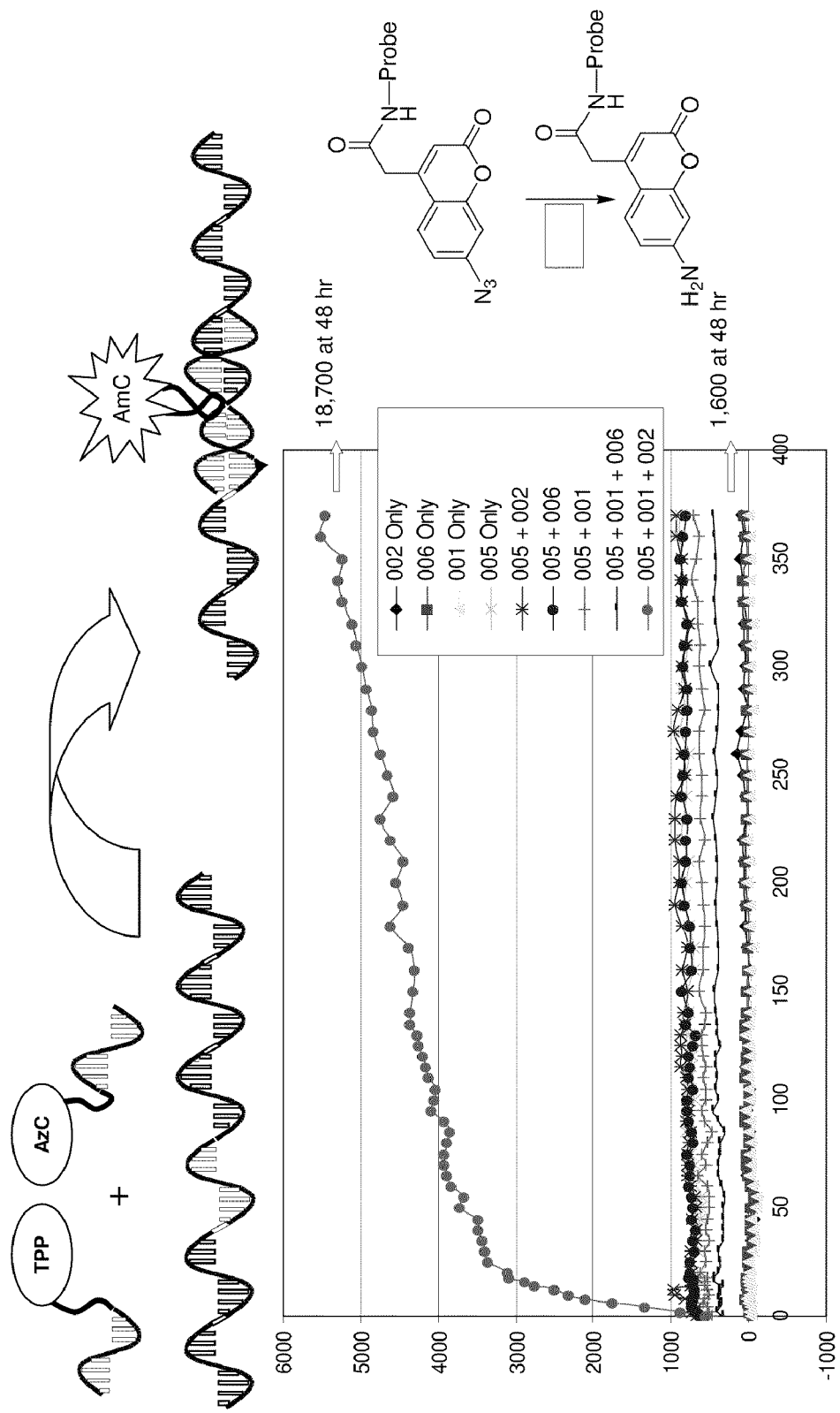
FIG. 30 shows an example of fluorescence signal generation and biological target detection via TPP and AzC reporter chemistry.

Results of additional experiments involving ternary complexes are shown in FIG. 30. In these experiments Oligo 1 is tested for its ability to bring together by hybridization two perfectly complementary oligonucleotides (Oligo5-AzC and Oligo-2TPP) versus its ability to bring together one perfectly complementary oligonucleotide (Oligo5-AzC) and one partially-complementary oligonucleotide (Oligo6-TPP). Oligo1 and Oligo5-AzC were at 200 nM final concentration, whereas Oligo2-TPP and Oligo6-TPP were employed at 400 nM final concentration. In FIG. 30, 001 denotes Oligo1, 002 denotes Oligo2-TPP, 005 denotes Oligo5-AzC, and 006 denotes Oligo6-TPP. The results show that fluorescence is generated only when the combination of fully complementary oligonucleotides is present (Oligo 1, Oligo5-AzC and Oligo2-TPP).

Example 17

Oligonucleotide Hybridization, Concentration and Melting Temperatures

A model system was prepared which included two twenty-mer oligonucleotides with a ten-base complementary region and ten-base single stranded spacer arms, further linked to a six carbon spacer arm. These oligos were synthesized both with and without a 5'-biotin (with a 6-carbon spacer arm). As shown below, the complementary region is underlined. A third oligo was identical to the (−) strand oligo but with 4 base mismatches (italicized) to the (+) strand.

```
                                          (SEQ. ID. NO. 24)
Oligo 26   (+) strand    5' CTTCGGCCCAGATATCGT (SEQ. ID. NO. 25)
Oligo 27   (−) strand    3' GTCTATAGCATCGACATC (SEQ. ID. NO. 26)
Oligo 28   (−) mismatch  3' TACTATAG TGTCGACATC
```

Melting curves of the 10-base pair oligonucleotide pair (oligo 26+oligo 27) were examined by measuring fluorescence of SYBR dye binding to double stranded DNA in a Bio-Rad iCycler (Lipsky, et al., Clinical Chemistry 2001, 47[4], 635-44). The binding curves are presented as the first derivative of the slope of the melting curve, such that a maximum value represents a point of inflection in the curve (a $T_m$, or in a mixed population of double stranded sites, a "local" $T_m$). Binding curves can be obtained up to at least 70° C. as avidin retains biotin binding activity up to this temperature and beyond.

Figure 31:
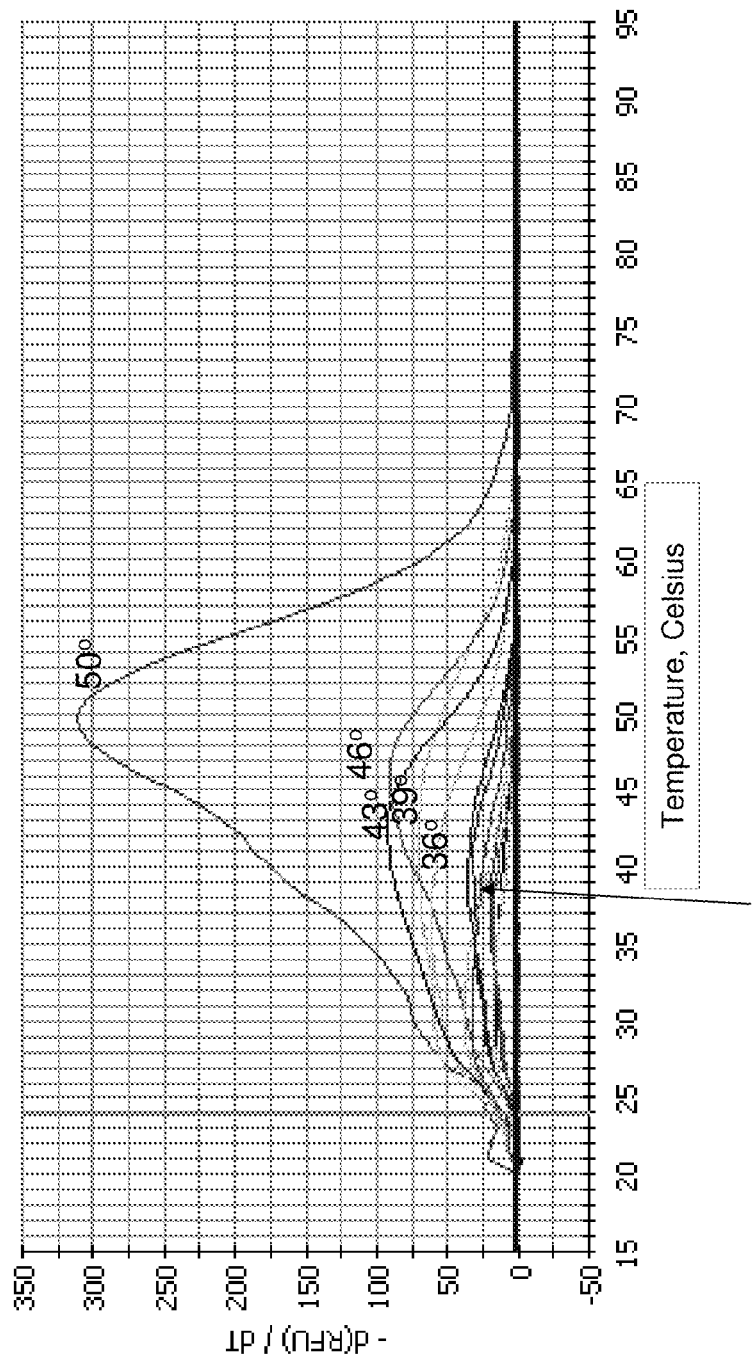
FIG. 31 shows certain examples of melt curves illustrating the effect of oligonucleotide concentration on $T_m$.

To check the dependence of this particular pair of oligonucleotides upon concentration, melting curves were generated for the oligonucleotide pair varied over the range from 500 to 20 nM (FIG. 31). (See, e.g., Lipsky, et al., Clinical Chemistry 2001, 47[4], 635-44). The observed $T_m$ dropped at the rate of about 10° C. per each ten-fold reduction in concentration (where RFU indicates relative fluorescence units) of the oligonucleotide pair, similar to prediction in the graph of FIG. 31. The melting curves were essentially identical for biotinylated and non biotinylated oligonucleotide pairs. The four base mismatched pair showed essentially no double stranded structure.

To test whether binding the (+) and (−) strands to a protein target would cause an increase in $T_m$, the biotinylated version of these oligonucleotides were incubated in the presence of avidin. Avidin contains 4 equivalent binding sites, which are spaced relatively close together and bind to biotin very tightly ($K_a \sim < 10^{-15}$ M) and non-cooperatively.

Presented with equal molar concentrations of oligonucleotides #26 and #27 in biotinylated form, it would be expected that about half of the biotin binding sites are occupied by complementary pairs of oligonucleotides, and about half with the same oligonucleotide (non-complementary pairs). The prediction is that one would observe two melting curve peaks in the presence of avidin. One peak would be the result of any pairs of oligonucleotides which were either not bound to avidin (free in solution) or which had only one partner of the two bound to avidin, which should not exhibit a proximity effect upon $T_m$. A second peak of significantly higher $T_m$ would represent a pair of biotinylated oligos both bound to avidin, which should exhibit a proximity effect.

Figure 33:
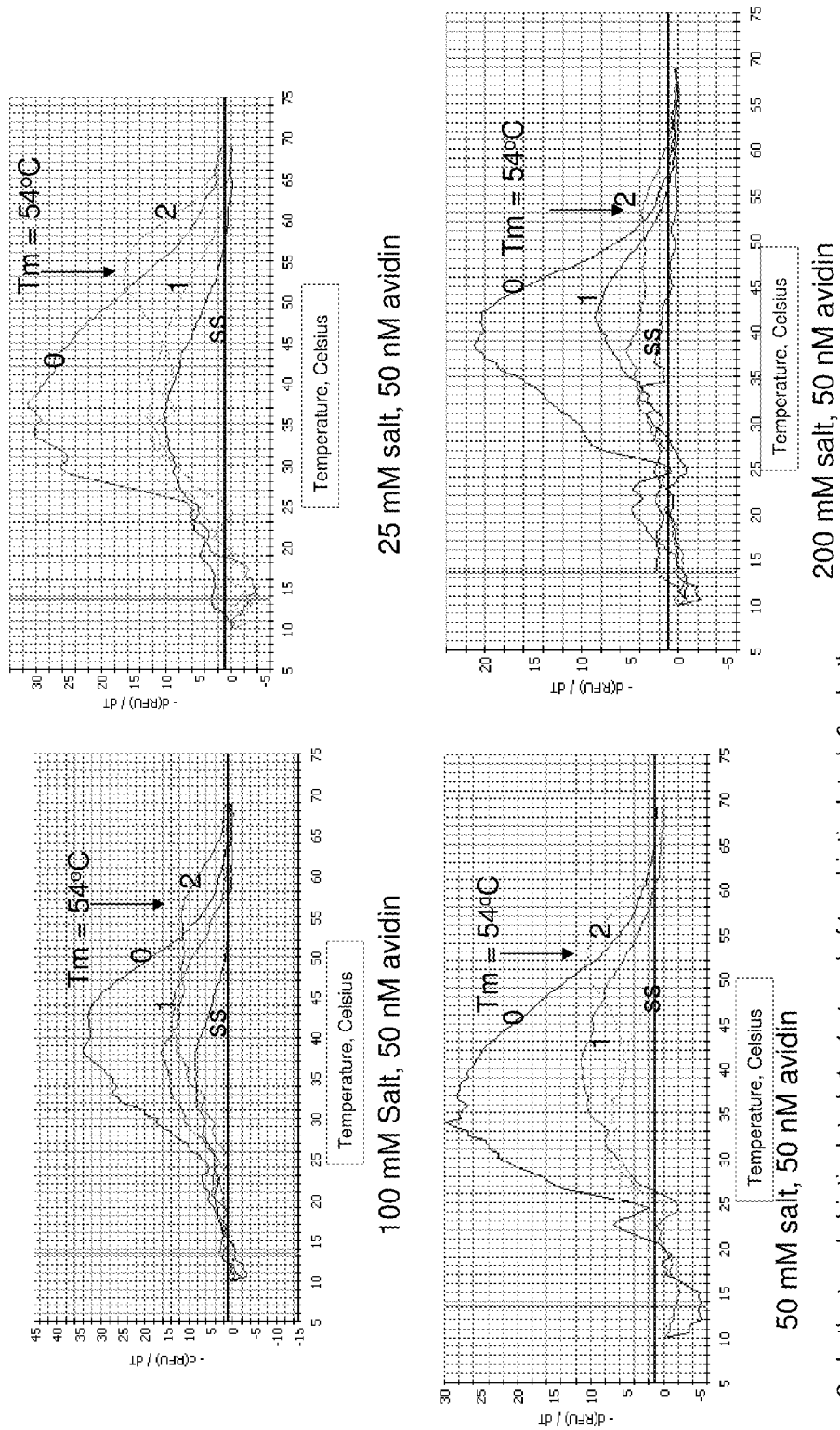
FIG. 33 shows certain examples of $T_m$ changes of complementary biotinylated oligos upon binding to avidin.
Figure 34:
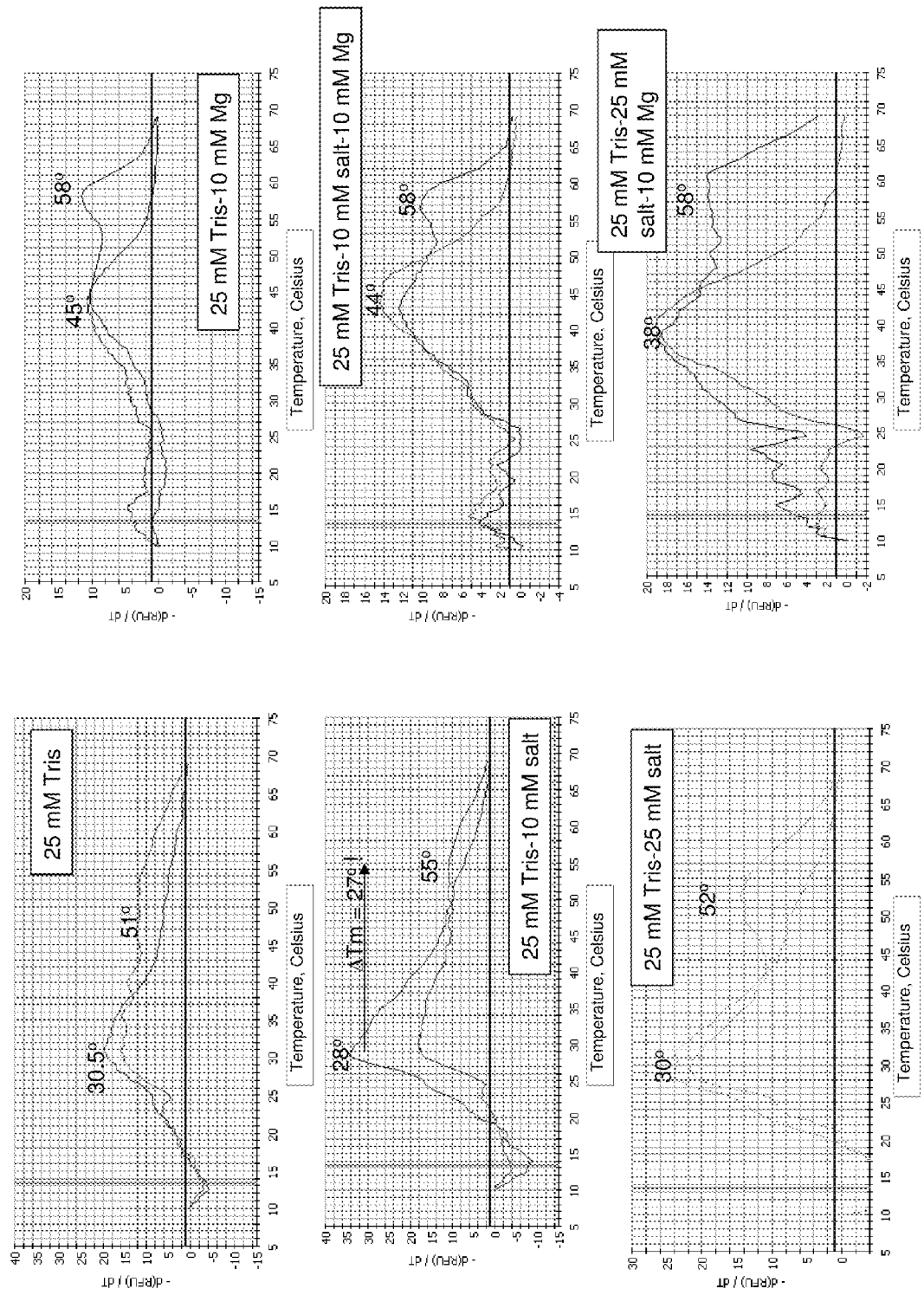
FIG. 34 shows certain examples of the effect of salt and magnesium concentrations upon $T_m$ of oligonucleotides +/−biotin.
Figure 35:
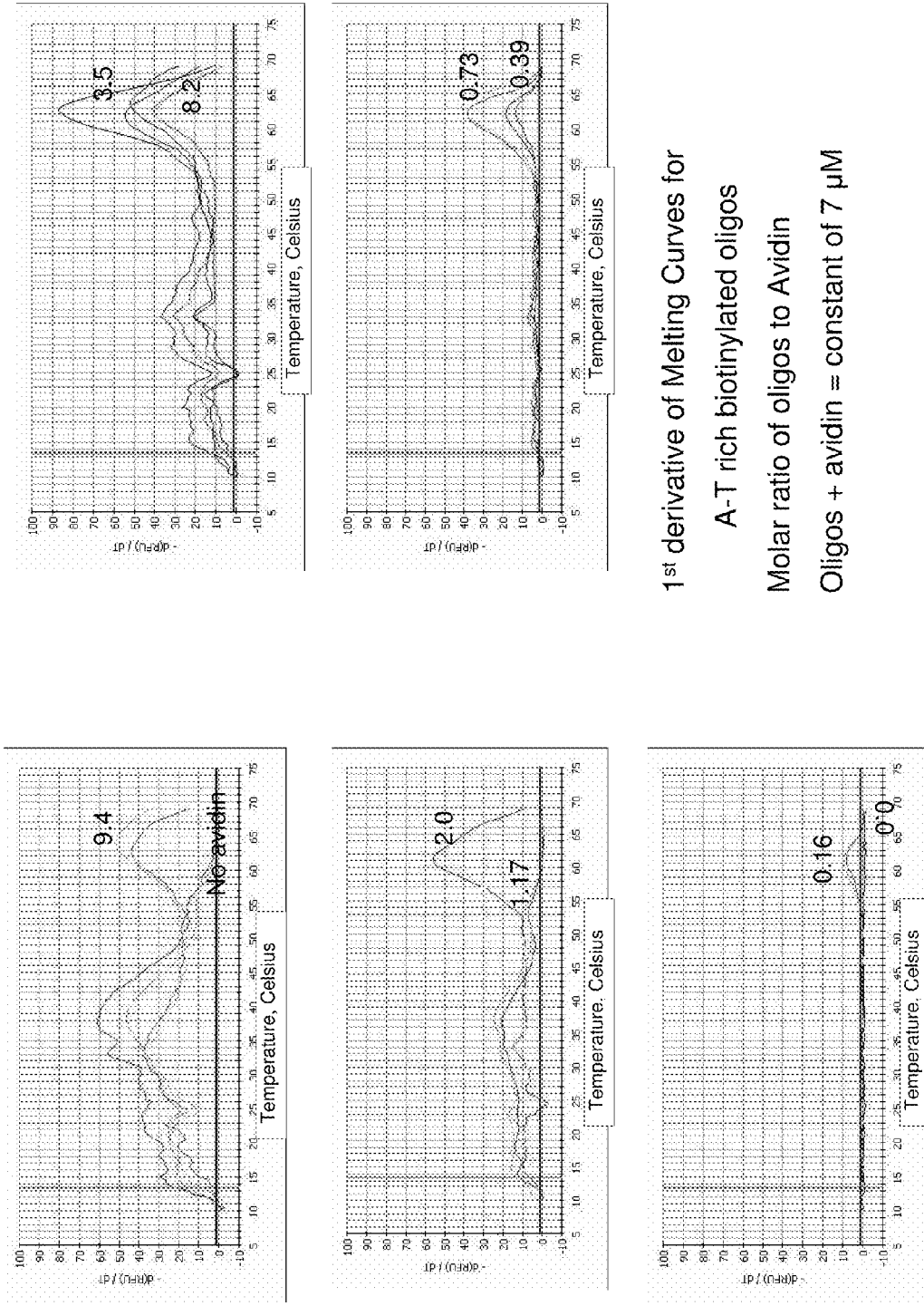
FIG. 35 shows certain examples of the melting temperature behavior of biotinylated oligonucleotides at different ratios of oligonucleotides to avidin.
Figure 36:
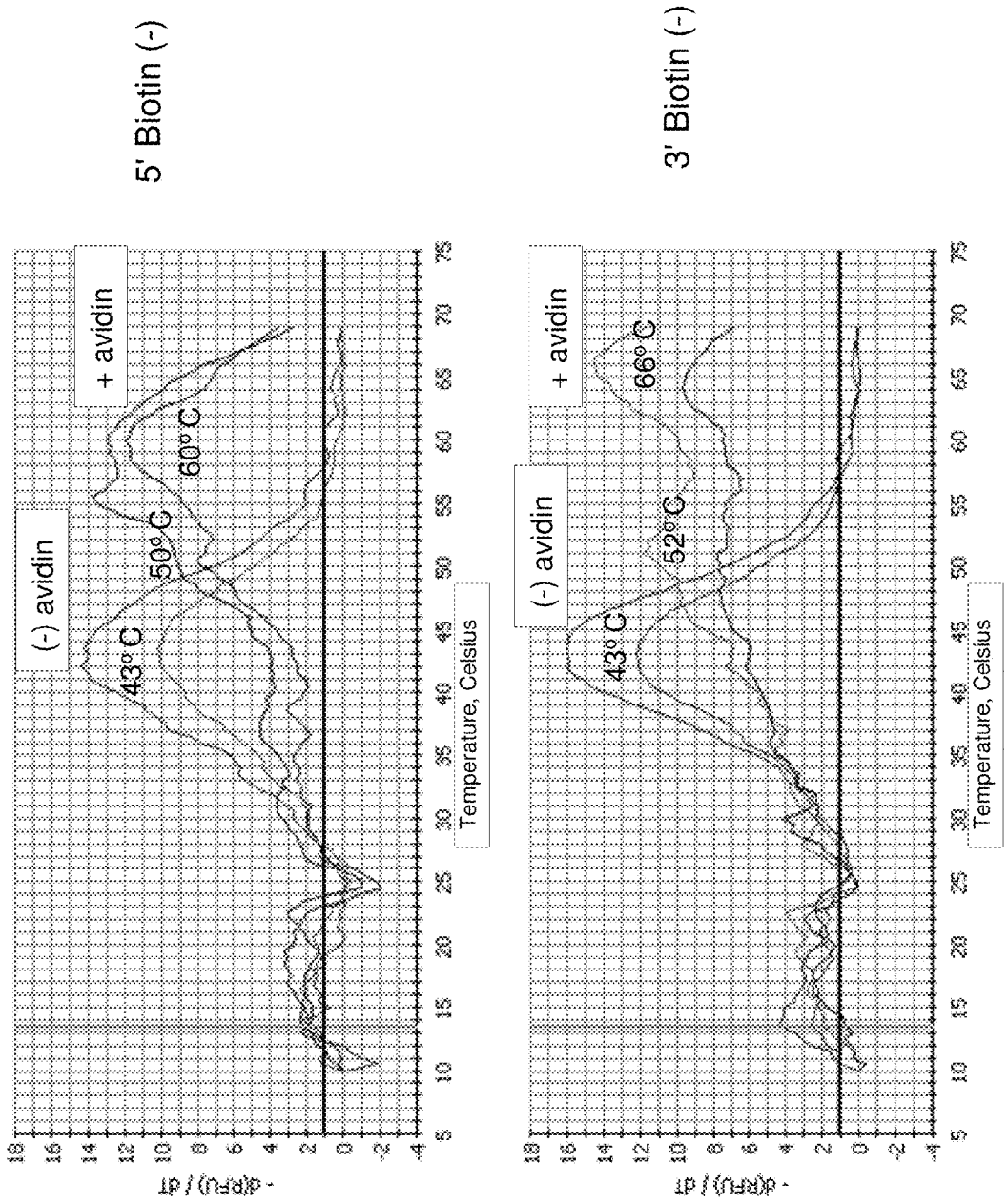
FIG. 36 shows certain examples of melting curves of 5' and 3' (−) biotin-strand oligos duplexed with biotin-5' (+) strand oligo in the absence and presence of avidin.

Such an experiment was conducted as shown in FIG. 32. The oligonucleotides were added to a solution in the presence or absence of avidin held at 60° C., a so-called hot start. In a "hot start," the oligonucleotides bind to the biotin binding sites at a temperature well above their $T_m$ in solution, assuring that they are single stranded. The solution was then ramped down to 10° C. and a melting curve analysis performed ascending to 70° C. As shown in FIG. 32, the melting curves of non-biotinylated oligo pair in the presence or absence of avidin showed a $T_m$ of 30-32° C. (where RFU indicates relative fluorescence units). In the presence of avidin, however, two well separated $T_m$ peaks were generated with $T_m$ values of 33° C. and 52° C. The elevated temperature peak ($T_m$ raised almost 20° C.) was observed only in the presence of two complementary biotinylated oligonucleotides in the presence of avidin. The difference in $T_m$+/−biotin tended to be greatest at lower salt concentrations (FIG. 33) and slightly higher in the presence of 10 mM magnesium chloride (FIG. 34) (where RFU indicates relative fluorescence units). The optimal molar ratio of biotinylated oligonucleotides to avidin was found to be about 3.5:1, (with total concentration of oligos+avidin=0.7 μM) consistent with avidin possessing four equivalent binding sites (FIG. 35) (RFU indicates relative fluorescence units). This is important because it substantiates that the requirement that the oligonucleotides bind to the same molecule of avidin for the $T_m$ effect to occur. The substitution of a 3' biotinylated (−) strand oligo for a 5' biotinylated strand oligonucleotide showed little difference in $T_m$ values (FIG. 36) (RFU indicates relative fluorescence units) with previous results in which both oligonucleotides were 5' biotinylated.

Results were essentially identical if the experiment was conducted by adding equimolar amounts of both the oligonucleotides at room temperature, ramping to 60° C., and then obtaining the melting curves. In this method (as well as the hot start method) suitable melting curves can be generated by adding an excess molar of each oligo relative to avidin if desired. (Large excesses of pairs of oligos increases the size of the low $T_m$ peak, however, as predicted.) This was not detrimental in forming high $T_m$ hybrid DNA since the pairs of oligos competed equally for biotin binding sites as long as they were added together in equal molar amounts. If oligos were added one at a time, it was important to add about a 2:1 molar ratio of the first oligo to avidin followed by a 2:1 ratio of the second oligo. With sequential addition, adding an excess molar amount of either oligo relative to avidin occupies all the binding sites of the avidin with the first oligo and prevents occupying adjacent sites with the second, complementary oligo and exhibiting the elevated $T_m$ effect. These observations are consistent with the mechanism being binding of adjacent pairs of complementary oligos to two adjacent biotin binding sites to obtain hybrids exhibiting the elevated $T_m$ peaks.

Figure 37:
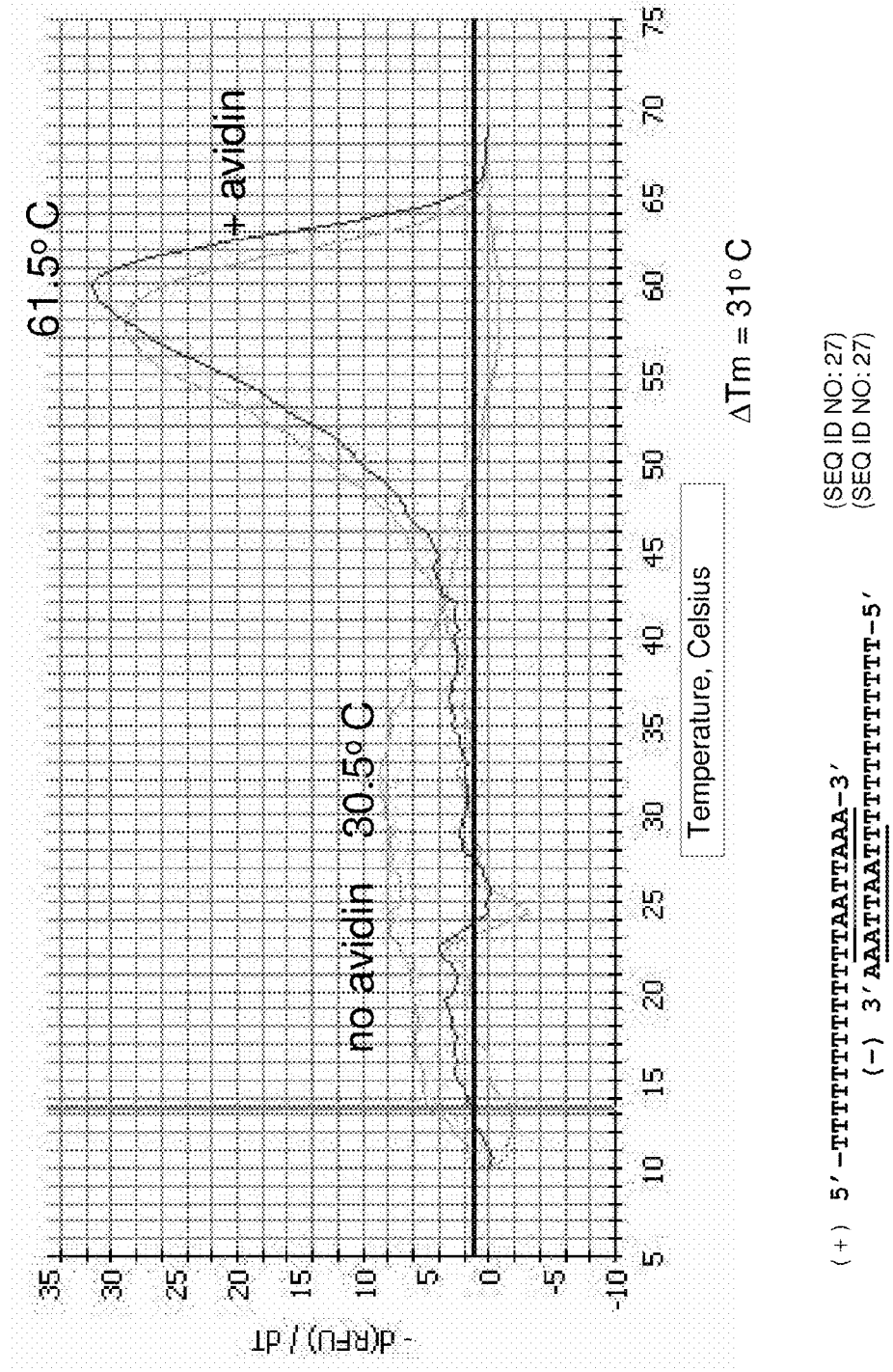
FIG. 37 shows certain examples of melting curves of AT-rich biotinylated oligo dimers with and without avidin.

Experiments were also conducted with a 10-base self-complementary oligonucleotide which was composed entirely of A and T. (Oligo 31: 5'-biotin-spacer arm-TTTTTTTTTTTTTAATTAAA) (SEQ. ID. NO. 27). Because this oligonucleotide was homogeneous in base composition and composed entirely of AT, it melted at a lower $T_m$ than the above-described model system and produced a fairly sharp melting curve. In the presence of avidin, its $T_m$ was increased from 30.5° C. to 61.5° C. (FIG. 37) (where RFU indicates relative fluorescence units). Since this oligonucleotide was self-complementary, all binding events lead to complementary strands, rather than only ½ of the events. Thus, only a single peak of increased $T_m$ was observed.

These experiments were repeated using anti-biotin antibody as a target rather than avidin. Anti-biotin antibody contains two biotin binding sites located near the ends of the Fab portion of the antibody, but the binding sites are much further apart than the biotin binding sites on avidin.

Example 18

Detection of Protein Targets—Aptamers as Target Binders

Here, an exemplary system was designed to utilize nucleic acid-templated azidocoumarin (AzC)-triphenylphosphine (TPP) chemistry to detect a protein target upon aptamer binding and annealing of the two complementary DNA probes.

Materials

Human PDGF-BB and PDGF-AA was obtained from R&D Systems (220-BB and 220-AA, respectively). Anti-human PDGF-B Subunit monoclonal antibody was obtained from R&D Systems (MAB2201). Buffers included Tris/Mg buffer, at 50 mM Tris/HCl, pH 8.0-10 mM MgCl$_2$. Oligonucleotides used were as follows:

Oligonucleotide Sequences Used in this Example

| Oligo #/ (SEQ. ID #) | Sequence (5' to 3') | 5'- Mod' f. | 3'- Mod 'f. | Description |
|---|---|---|---|---|
| 201 (28) | CAGGCTACGGCACGTAGAGCATCACC ATGATCCTGCCCCCCCCCCATATTTA AGC | TPP | none | DPC-aptamer probe |
| 202 (29) | GCTTAAATATCCCCCCCCCCAGGCT ACGGCACGTAGAGCATCACCATGATC CTG | none | AZC | DPC-aptamer probe |
| 203 (30) | GTGGGAATGGTGCCCCCCCCCCAGG CTACGGCACGTAGAGCATCACCATGA TCCTG | none | AZC | DPC-aptamer probe-mismatch |
| 204 (31) | GTGGTAGTTGGAGTCGTGGCGTAGGC AAGA | none | none | target |
| 205 (32) | GTGGTAGTTGGAGTCACACGTGGCGT AGGCAAGA | none | none | target |
| 206 (33) | GTGGTAGTTGGAGCTCACACCACACG TGGCGTAGGCAAGA | none | none | target |
| 207 (34) | GTGGTAGTTGGAGTCACACACACCAC ACACAGTGGCGTAGGCAAGA | none | none | target |
| 208 (35) | GTGGTAGTTGGAGCTCACACCACACC AACCACACCACACCACACACACCACA CGTGGCGTAGGCAAGA | none | none | target |
| 209 (36) | GTGTGGTGTGGTGTGGTGTG | none | none | splint |
| 210 (37) | GTGGCGTAGGCAAGAGTGGTAGTTGG AGCT | none | none | K-ras target outward facing |
| 211 (38) | GTGGGAATGGTG | none | TPP | TPP probe |
| 212 (39) | AGATCCCACTAGCAC | TPP | none | TPP probe |
| 213 (40) | AGCTCCAACTACCAC | TPP | none | TPP "mismatch" |
| 214 (41) | TCTTGCCTACGCCAC | none | AZC | AZC probe |
| 215 (42) | CAGGCTACGGCACGTAGAGCATCACC ATGATCCTG | none | none | aptamer |

Methods

DPC Reaction conditions. Except as noted, each 100 microliter reaction contained, in a total volume of 100 μl, 1×Tris/Mg buffer, 40 picomoles of TPP and AzC reaction probes, 40 picomoles of target oligonucleotide or of target protein, and typically 25-30% v/v of formamide. Samples were incubated at 25° C. in a Wallac Victor 1420 spectrophotometer and the increase in fluorescence monitored with excitation at 355 nm and emission at 460 nm.

Results: Detection of PDGF-BB by Aptamer-DPC Probes

Figure 38:
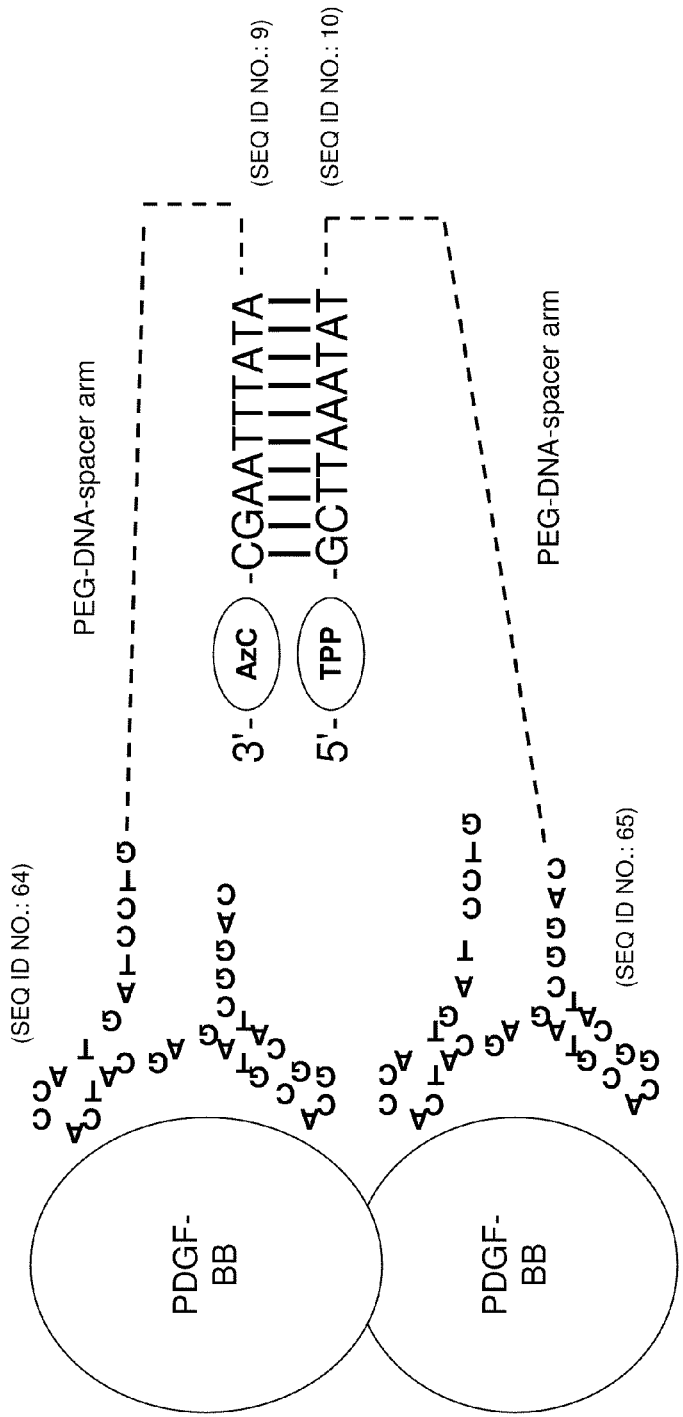
FIG. 38 is a schematic representation of a method for the detection of a biological target under one embodiment of the present invention.

As illustrated in FIG. 38, an aptamer sequence directed against platelet-derived growth factor (PDGF) B-subunits was selected (Fang, et al., Chem. BioChem. 2003, 4, 829-34.). This belongs to a family of aptamers with strong affinity for PDGF B subunit (~$10^{-9}$ M), and about ten-fold reduced affinity for PDGF A subunit. (Green, et al., Biochemistry 35, 14413-24. 1996) The probe sequences were synthesized, each containing a complementary 10-mer DNA sequence, a $C_{10}$ spacer sequence, and the same 35-mer aptamer sequence. (Oligos #201, #202). Each sequence contained a 5'-TPP or 3'-AZC group with the aptamer linked 3' or 5', respectively. A second AzC probe, oligo #203, was the same as oligo #202 except that its annealing sequence was entirely mismatched to the TPP oligo (#201).

Figure 39:
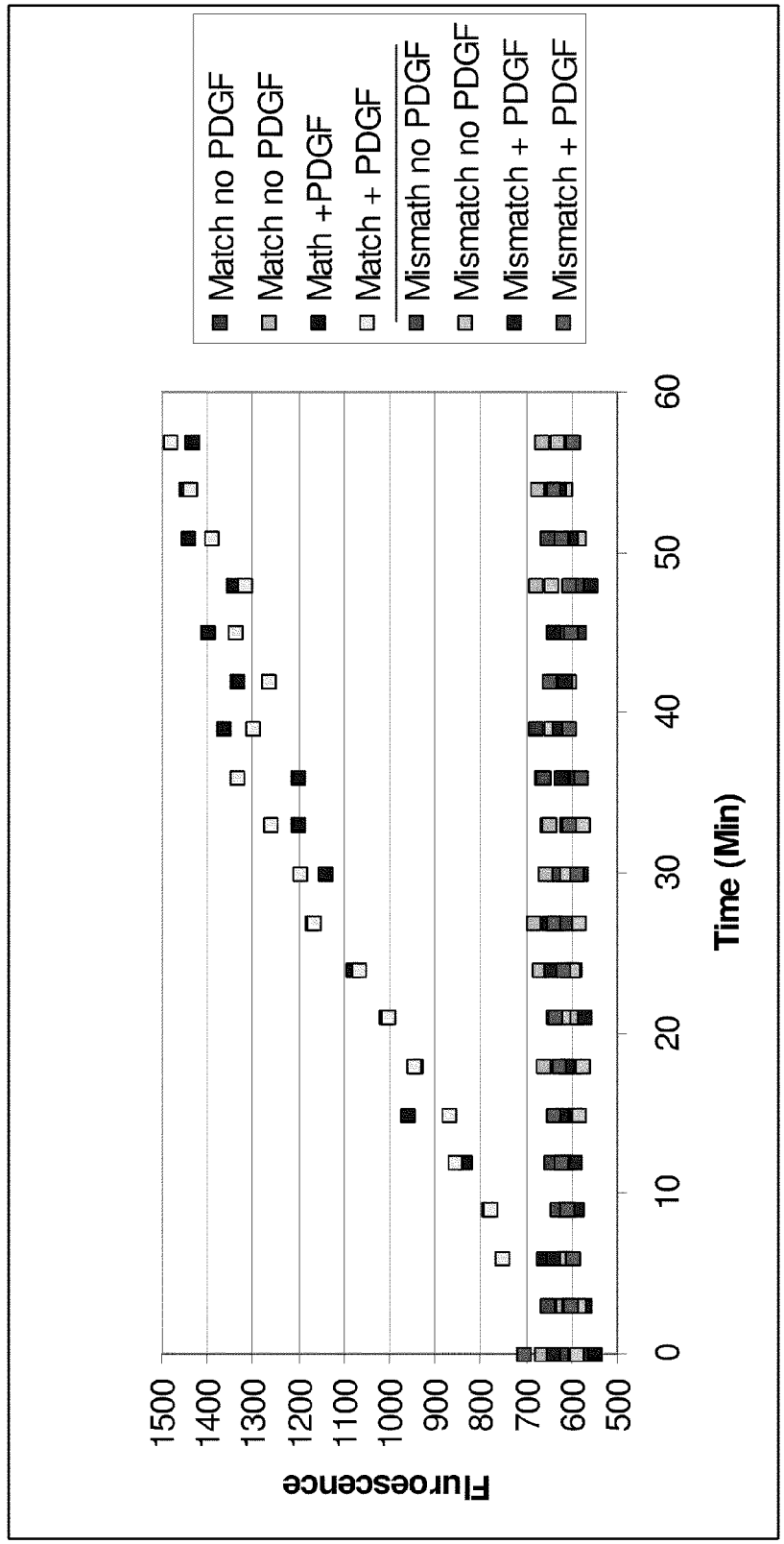
FIG. 39 shows examples of experimental results on detection of a biological target under one embodiment of the present invention.

As shown in FIG. 39, in the presence of 30% (volume) formamide, the reaction of the TPP and AzC probes with each other was entirely dependent upon the presence of PDGF-BB and complementary DNA sequences on the probes. The reaction failed in the absence of either probe.

Figure 40:
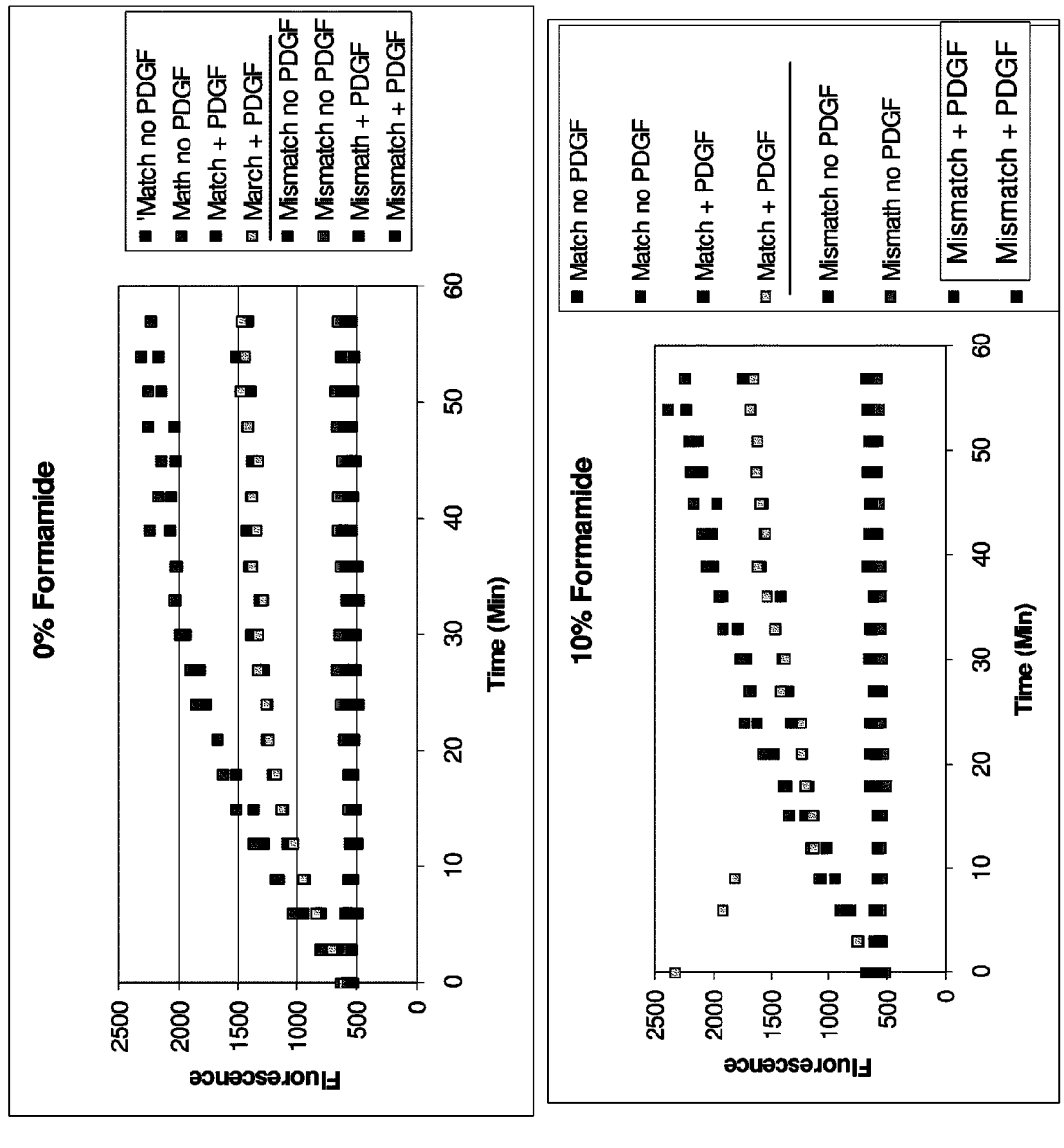
FIG. 40A and FIG. 40B show examples of experimental results (the effect of formamide in the reaction mixture) on detection of a biological target under one embodiment of the present invention.

The DNA-dependence of the reaction was critically dependent upon the melting temperature of the DNA relative to the assay temperature. In the presence of 0% formamide (with the calculated and observed $T_m > T_{assay}$, the reaction took place in the presence or absence of the target protein PDGF-BB (FIG. 40A). In fact, under these conditions, addition of PDGF-BB did not increase, but reduced the reaction rate by about 50%. In 10% formamide, PDGF-BB was less inhibitory (FIG.

Figure 41:
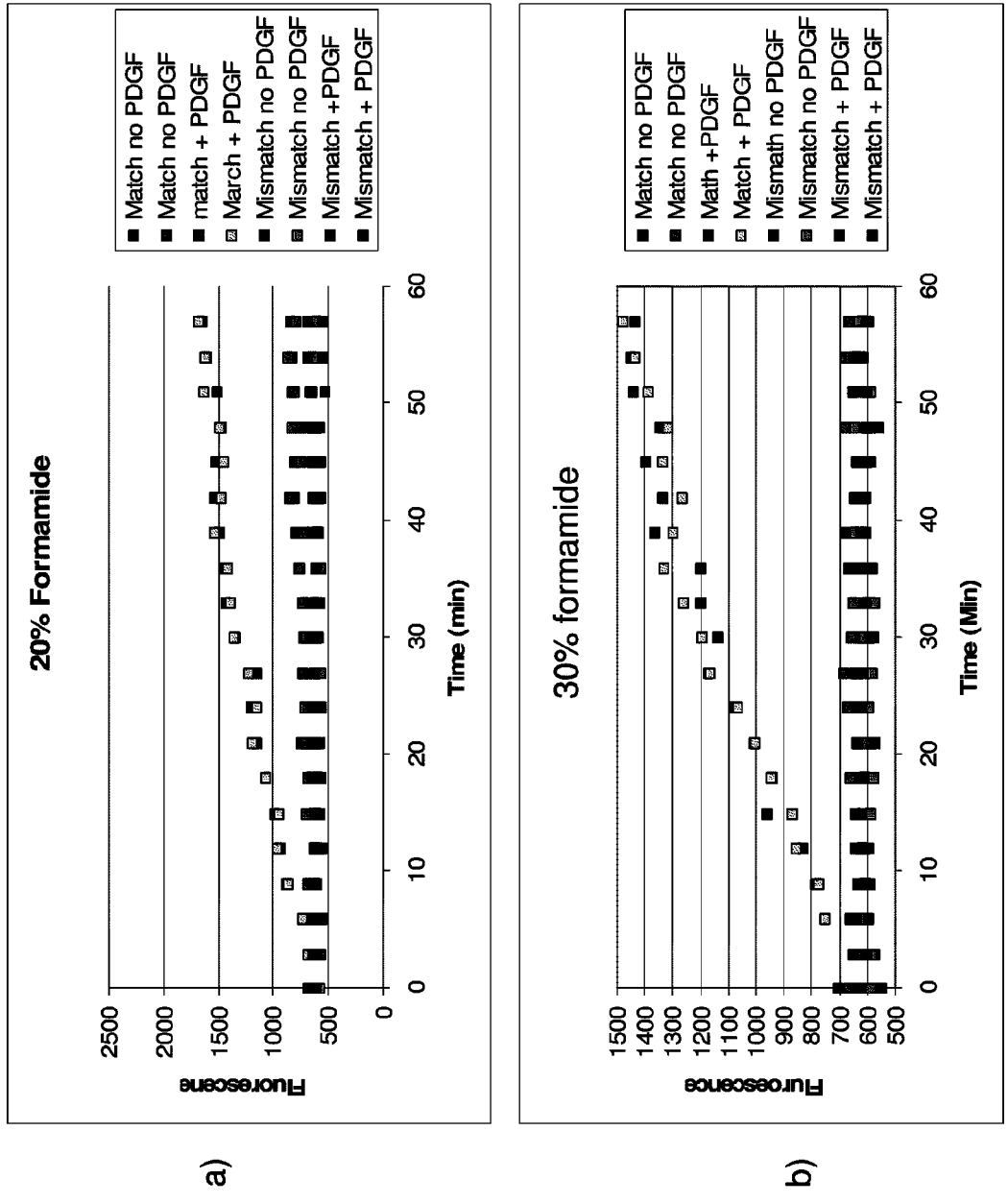
FIG. 41A and FIG. 41B show examples of experimental results (the effect of formamide in the reaction mixture) on detection of a biological target under one embodiment of the present invention.
Figure 42:
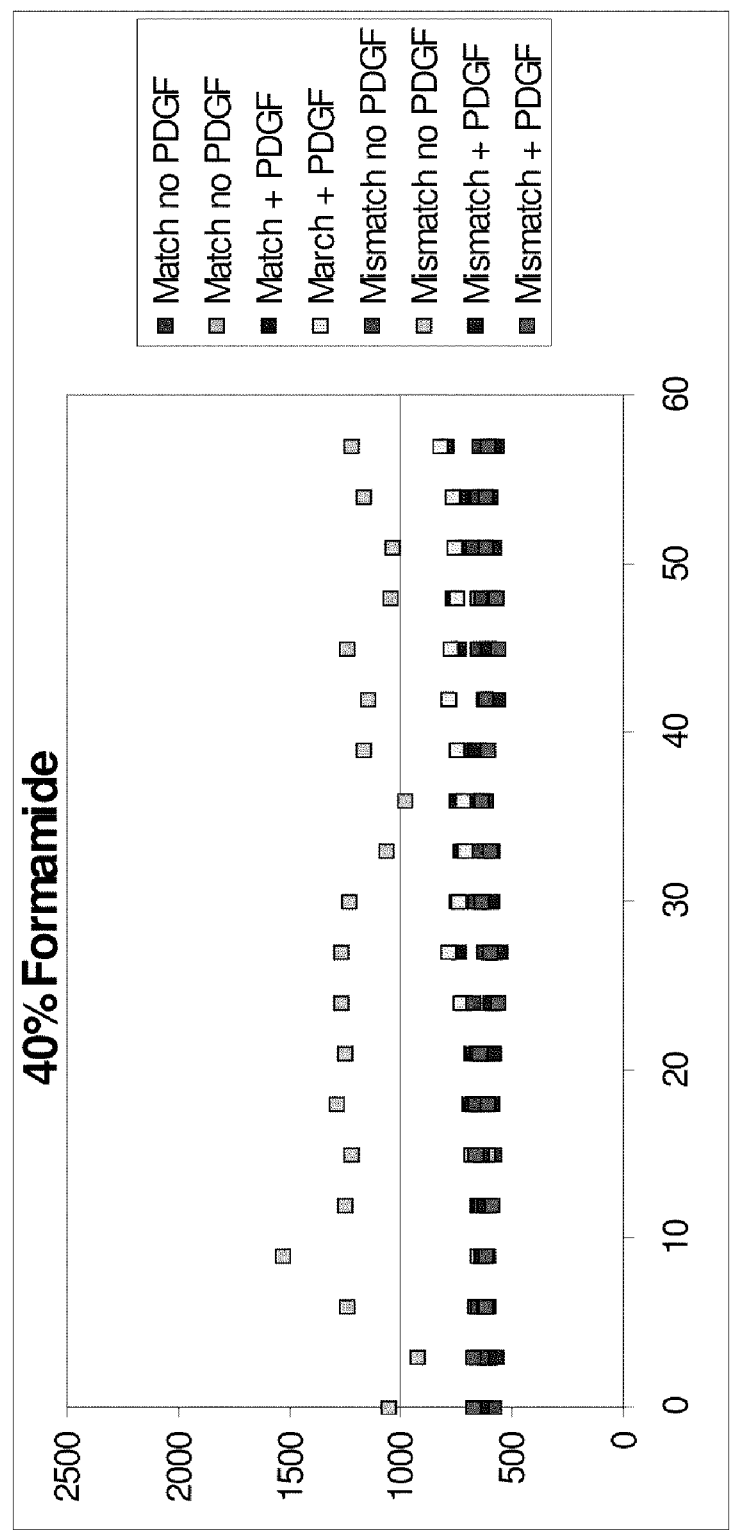
FIG. 42 shows examples of experimental results (the effect of formamide in the reaction mixture) on detection of a biological target under one embodiment of the present invention.

40B). In 20% formamide (FIG. 41A), the situation was completely reversed—the reaction rate was now weak except in the presence of PDGF-BB. In 30% formamide (FIG. 41B) the reaction was completely dependent upon the presence of PDGF-BB. In 40% formamide, the reaction was very slow with any set of reactants (FIG. 42). In all cases, the mismatched probes produced little or no reaction.

DNA melting experiments with the complementary sequences, monitored with SYBR Green had indicated a $T_m$ of the sequence of about 30° C. in the Tris/Mg buffer in the absence of formamide, and about 7° C. lower for every 10% increase in formamide. $T_m$ in the optimal formamide concentration for the detection assay, 30%, was 10° C.

In 0% formamide, the oligonucleotides can form at least a partial duplex even in the absence of PDGF-BB ($T_m$ slightly higher than $T_{assay}$). The DNA target-dependence of the reactions in 20% and 30% formamide is explained by the assay being conducted at a temperature greater than the $T_m$ in the absence of protein target. No reaction occurs unless the $T_m$ of the complex is increased by the binding of the two probes to the PDGF-BB target. At 40% formamide, the reaction doesn't occur with any set of reactions. The likely explanation is that either the $T_m$ had been reduced so low that binding to PDGF-BB could not raise it above $T_{assay}$, or that formamide had inhibited PDGF-BB binding to the aptamers. A more complex situation is the observed inhibition of reaction rate upon addition of PDGF-BB in the absence of formamide. Since half of the duplexes formed by PDGF-BB are non-productive (50% will be homoduplexes) the reduction in rate is likely due to PDGF-BB binding preventing these homoduplexes from disassociating and then reassociating in solution with complementary pairs to form heteroduplexes. This situation should not occur using pairs of probes specifically directed against different binding sites in a heterodimeric target.

Figure 43:
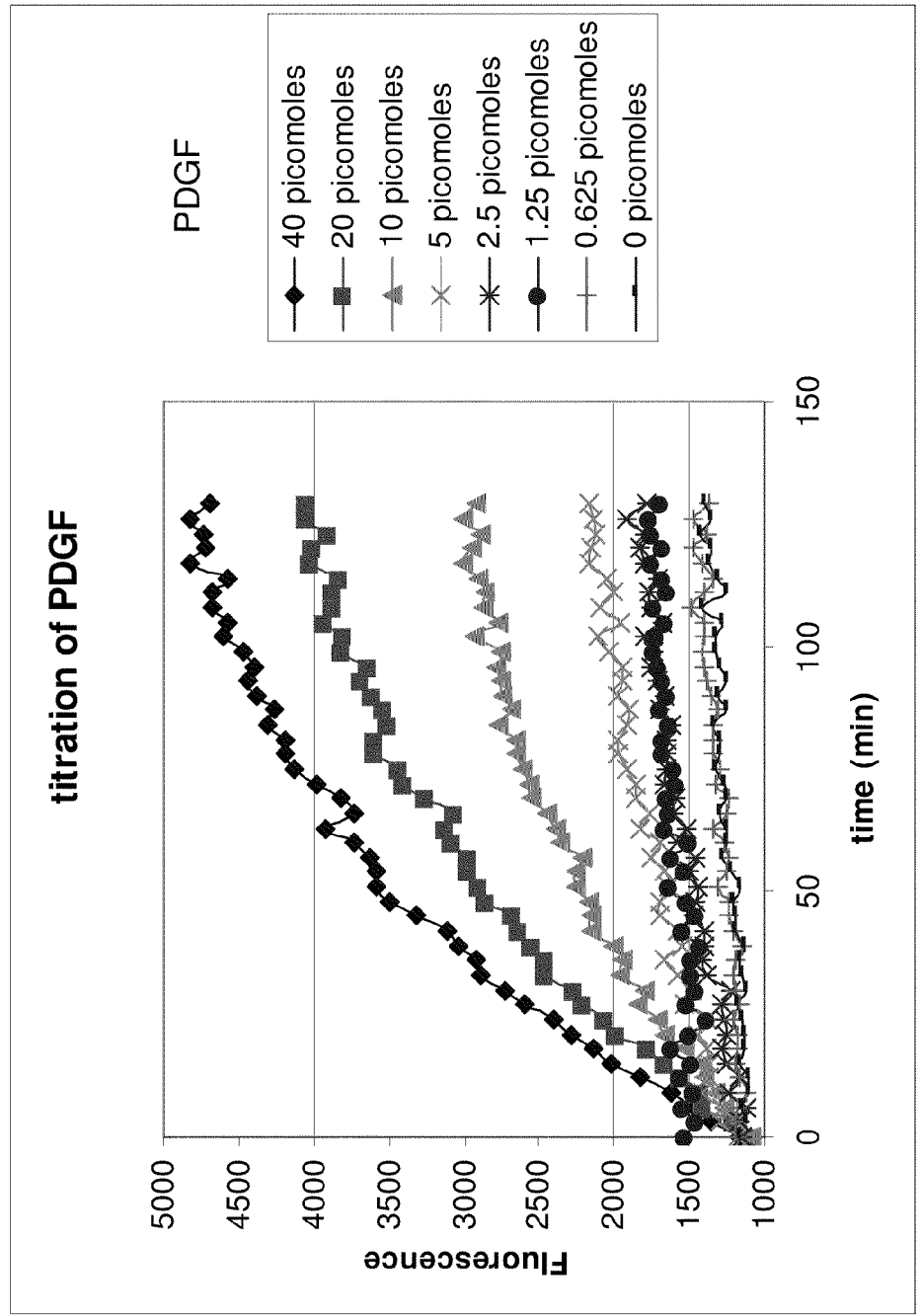
FIG. 43 shows examples of experimental results (time course of reaction mixtures) on detection of a biological target under one embodiment of the present invention.

The sensitivity of the assay (FIG. 43) was calculated by measuring reaction rates generated from a dilution series of PDGF-BB concentrations. The minimum detection level on the Wallac instrument was estimated at 0.8 picomoles in a 100 microliter assay volume, based upon the calculated value of three times the standard deviation of the background noise of the assay.

Figure 44:
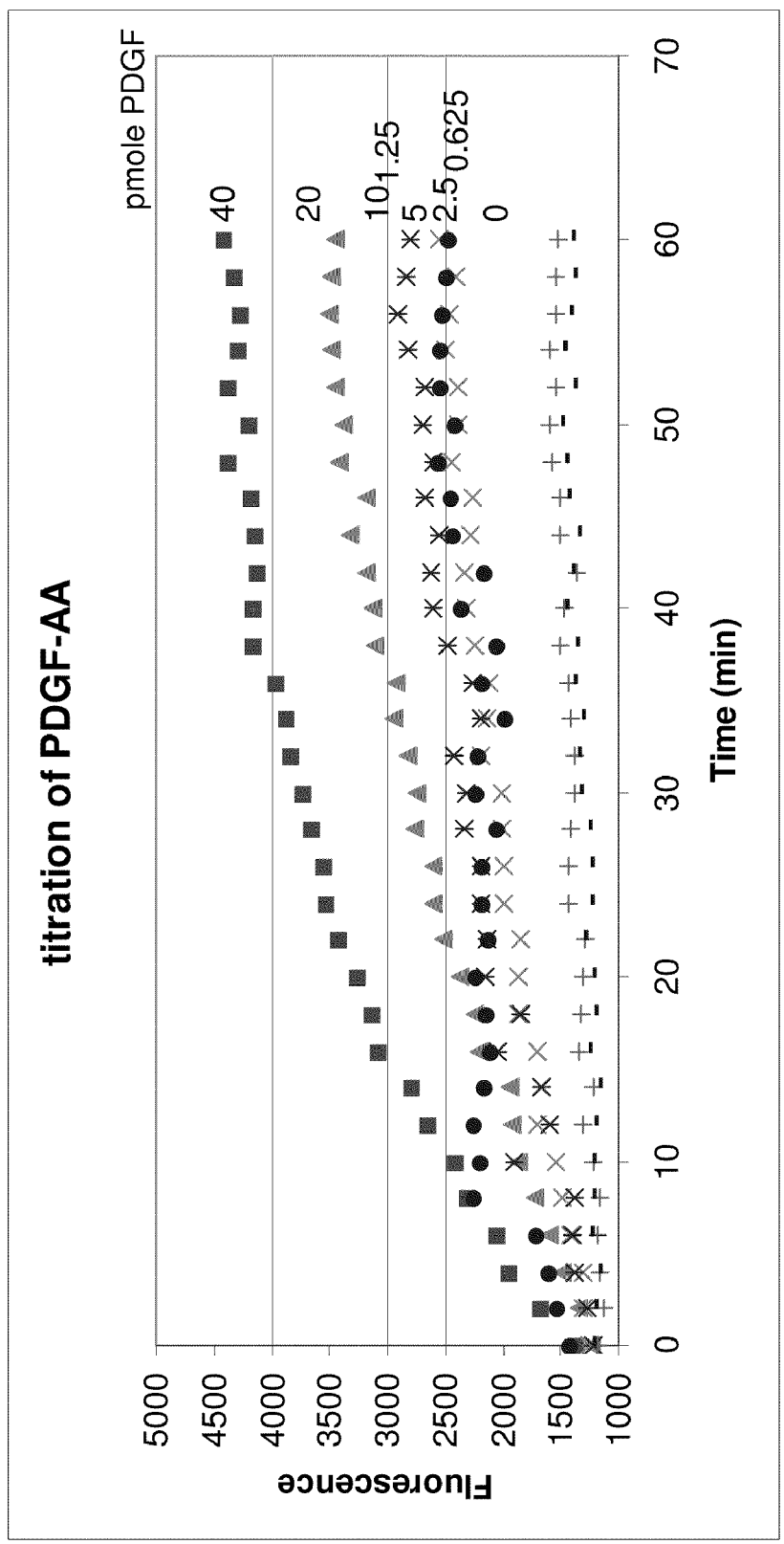
FIG. 44 shows examples of experimental results (time course of reaction mixtures) on detection of a biological target under one embodiment of the present invention.

The assay sensitivity was also determined using PDGF-AA as a target. The aptamer monomer is expected to have an affinity for PDGF-AA about ten times weaker than for PDGF-BB. However, since the assay involves forming a complex of two aptamer-dimers to either type of PDGF, the avidity of binding of the dimer is expected to be tighter than the affinity of the monomer, and its affinity should be substantially tighter (lower $K_i$) than the concentrations tested of the target PDGFs (down to about 1 nanomolar). As shown in FIG. 44, the reaction rates of the aptamer DPC probes to PDGF-AA at low or high concentrations (0, 1.25, 2.5, 5, 10, 20, and 40 pmole of PDGF-AA) were not substantially different than the reaction rates with PDGF-BB. This is consistent with the model of an aptamer pair binding as a dimer and exhibiting increased avidity.

Figure 45:
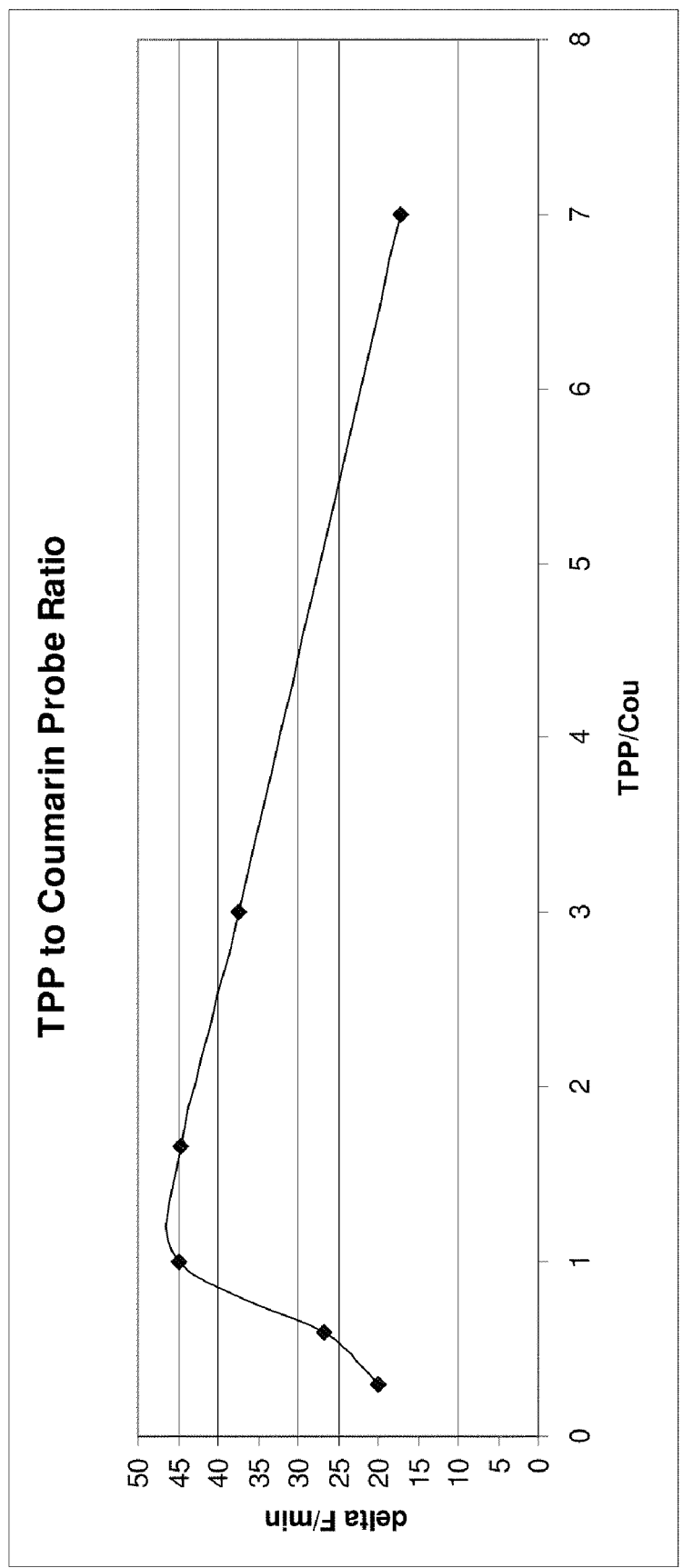
FIG. 45 shows examples of experimental results (probe ratios) on detection of a biological target under one embodiment of the present invention.

Ratios of TPP to AzC Probes. To confirm the model of the reaction mechanism (FIG. 8, the optimal ratio of TPP to AzC probes would be expected to be 1:1), FIG. 45 was an experiment in which the total amount of the two probes was kept constant, at 800 nMoles probes/reaction, while the ratio of the two probes was varied. The ratio producing the highest reaction rate was approximately 1:1, consistent with the expected mechanism.

Thus, in this model system fluorescence was not generated unless the aptamers bound and the complementary sequences in the two probes annealed to each other.

Example 19

Zip-Coded Architecture for Nucleic Acid-Templated Chemistry Based-Biodetection with Aptamer Binders FIG. 14 [15x] illustrates in more detail an exemplary zip-code architect. The TPP pair contained, first, a PDGF-aptamer on the 5'-end, a C18 polyethylene-glycol based spacer, and an 18-mer zip code sequence. The TPP reporter sequence contained a complementary anti-zip code sequence on its 3' terminus, a C18 PEG spacer, and a ten base pair reporter sequence terminating in a 5' TPP group. The pair of oligonucleotides comprising the AzC detection probe contained a 3'-aptamer linked through a C18 PEG spacer to a separate zip code, and a detection oligonucleotide linked to a 5' anti-zip code, a C18 PEG spacer, and a reporter oligonucleotide (complementary to the TPP oligonucleotide) terminating in a 3' AzC group.

Figure 46:
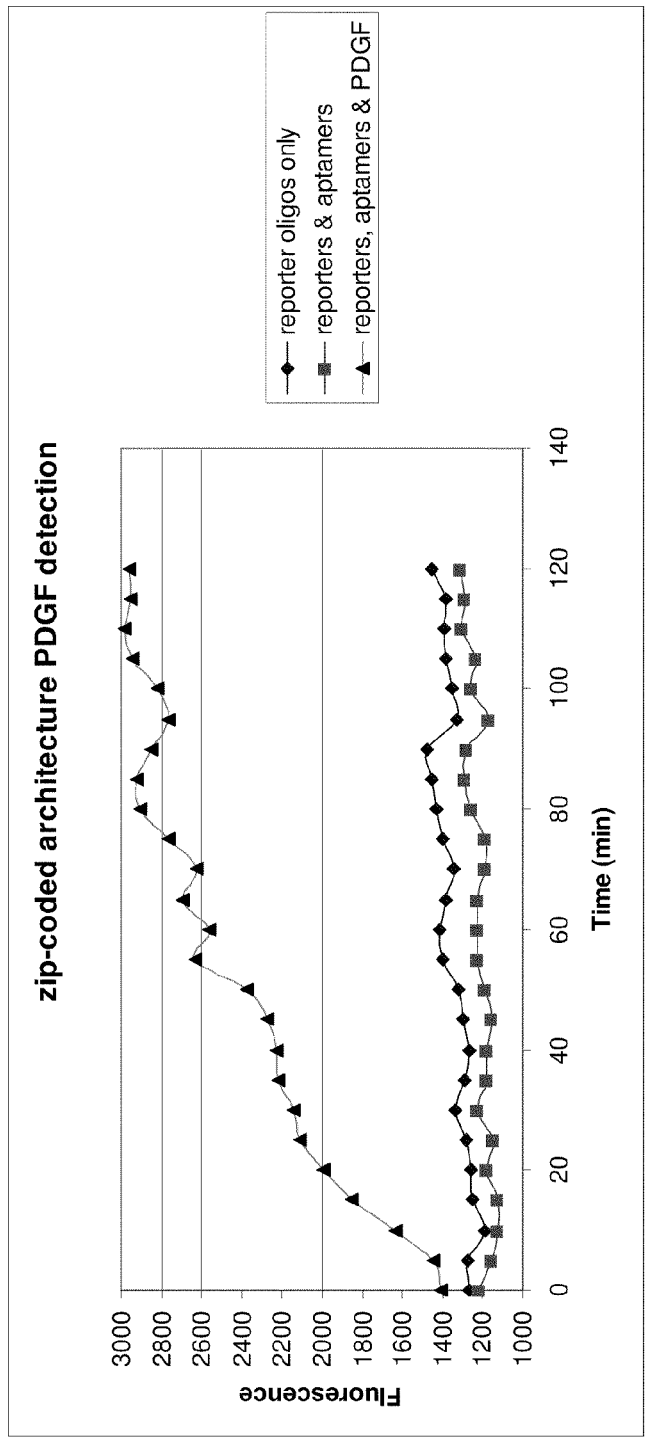
FIG. 46 shows an example of detection of PDGF by a zip-coded detection system.

The reaction, in 35% formamide at 22° C., was dependent upon the presence of both of the reporter oligonucleotides, both of the aptamer oligonucleotides, and the target, PDGF-BB (FIG. 46). At 22° C. in the absence of formamide, the reaction proceeded independently of the presence of PDGF. This is consistent with the behavior of the above-described "one-piece" architech, and reflects that the mechanism of fluorescence generation in 35% formamide is dependent the increased thermal stability of the reporter sequence duplex in formamide upon addition of PDGF. In the absence of formamide at 22° C., the reporter oligonucleotide duplex is stable both in the presence and absence of PDGF.

Figure 47:
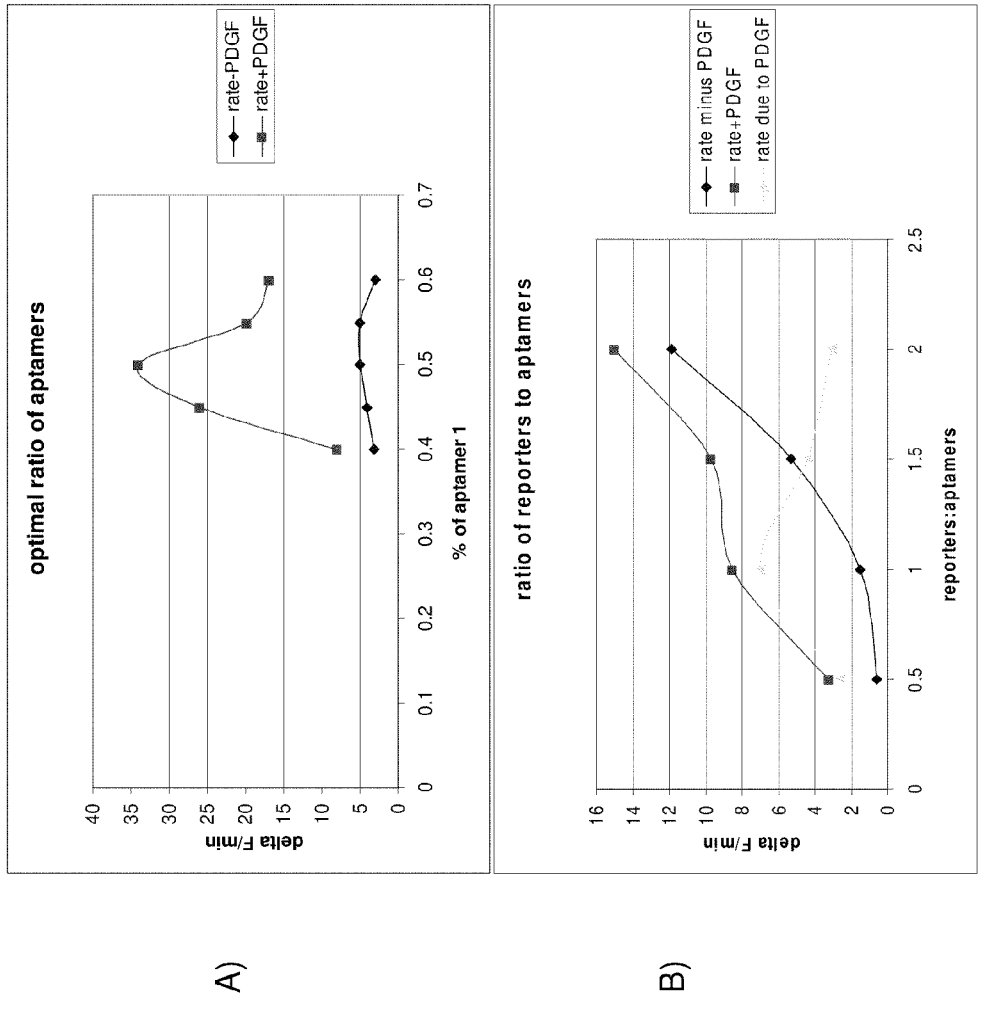
FIG. 47 shows experiments on ratios of aptamers and reporters.

Confirmation of the correctness of the model was obtained with experiments varying the ratio of the TPP and AzC aptamer oligos (FIG. 47). These experiments indicated that the optimal ratio of the aptamer oligos was the expected 1:1 ratio (i.e. 50% TPP oligo with a total concentration of PDGF and aptamer oligos of 0.4 μM). The optimal ratio of total reporter oligonucleotides to total aptamer oligos was also 1:1. No PDGF-dependent reaction occurred in the complete absence of either one of the reporter or aptamer oligonucleotides. At higher than stoicheometric concentrations of reporter oligonucleotides, the PDGF-independent signal increased (background) but the PDGF-dependent signal remained about constant. Both of these observations are consistent with the model that the complex is assembled in the ratio of 1:1:1 for each of the aptamer oligos, each of the reporter oligos, and PDGF.

These experiments indicate that the complex can self-assemble in solution, such that each zip code and its anti-zip code anneal to each other with minimal interference with the aptamer sequence or the reporter sequences.

Experiments were also conducted to determine if the order of addition, and thus assembly of the aptamer and reporter probes, was of any importance. Slightly slower reaction rates were obtained if the aptamer oligonucleotides were first incubated with PDGF before adding the reporter oligonucleotides, compared with adding all probes together as a mixture. Somewhat greater reaction rates were obtained if each pair of aptamer oligonucleotides and reporter oligonucleotides was first incubated and allowed to assemble with each other before the two sets were mixed together and incubated with PDGF. The reason for this may be that there is some steric hindrance to zip code-anti zip code annealing to aptamer probe if the aptamer probe is already bound to target.

As a control, a set of one-piece TPP and AzC probes was compared which contained only the zip code sequences and no zip code-anti zip code sequences (FIG. 48). The reaction rates of this one-piece system were similar to that of the two-piece system, except that the rate enhancement due to the addition of PDGF was typically slightly better than that of the two-piece system.

The sequence of the aptamer-containing TPP and AzC probes was also systematically varied to determine any constraints on the design. The aptamer-containing TPP and AzC oligos were synthesized, both having the same sequences as described in FIG. 14 but with the following changes: (1) omission of the C18-PEG spacer. (Oligos 119 & 122); (2) replacement of the C18-PEG spacer with the sequence $C_{10}$. (oligos 120 & 123); (3) replacement of the C18-PEG spacer with the sequence $C_{20}$. (oligos 121&124); (4) Omission of the C18-PEG spacer and omitting 3 3'-bases in the zip code region (reduction to 15 bases in length). (oligos 127 & 129); and (5) omission of the C18-PEG spacer and omitting 6 3'-bases in the zip code region (reduction to 12 bases in length). (oligos 128 & 130).

Oligonucleotides used in this example included:

| Oligo#/ | Sequence (5'-3') | Modification |
|---|---|---|
| | | (SEQ. ID NO. 43) |
| 106 | GGACTCGAGCACCAATAC-X-TATAAATT CG-AZC | X = C18 PEG; AZC = 3'-AzC. |
| | | (SEQ. ID NO. 44) |
| 109 | CGAATTTATA-X-CTGACCATCGATGGCA GC | X = C18 PEG, 5'-TPP |
| | | (SEQ. ID NO. 45) |
| 112 | CAGGCTACGGCACGTAGAGCATCACCATG ATCCTG-X-GCTGCCATCGATGGTCAG | X = C18 PEG |
| | | (SEQ. ID NO. 46) |
| 113 | GTATTGGTGCTCGAGTCC-X-CAGGCTAC GGCACGTAGAGCATCACCATGATCCTG | X = C18 PEG |
| | | (SEQ. ID NO. 47) |
| 119 | GTATTGGTGCTCGAGTCCCAGGCTACGGC ACGTAGAGCATCACCATGATCCTG | |
| | | (SEQ. ID NO. 48) |
| 120 | GTATTGGTGCTCGAGTCCCCCCCCCCCCC AGGCTACGGCACGTAGAGCATCACCATGA TCCTG | |
| | | (SEQ. ID NO. 49) |
| 121 | GTATTGGTGCTCGAGTCCCCCCCCCCCCC CCCCCCCCCCAGGCTACGGCACGTAGAGC ATCACCATGATCCTG | |
| | | (SEQ. ID NO. 50) |
| 122 | CAGGCTACGGCACGTAGAGCATCACCATG ATCCTGGCTGCCATCGATGGTCAG | |
| | | (SEQ. ID NO. 51) |
| 123 | CAGGCTACGGCACGTAGAGCATCACCATG ATCCTGCCCCCCCCCCGCTGCCATCGATG GTCAG | |
| | | (SEQ. ID NO. 52) |
| 124 | CAGGCTACGGCACGTAGAGCATCACCATG ATCCTGCCCCCCCCCCCCCCCCCCCCGCT GCCATCGATGGTCAG | |
| | | (SEQ. ID NO. 53) |
| 127 | CAGGCTACGGCACGTAGAGCATCACCATG ATCCTGGCTGCCATCGATGG | |
| | | (SEQ. ID NO. 54) |
| 128 | CAGGCTACGGCACGTAGAGCATCACCATG ATCCTGGCTGCCATCGAT | |
| | | (SEQ. ID NO. 55) |
| 129 | TTGGTGCTCGAGTCCCAGGCTACGGCACG TAGAGCATCACCATGATCCTG | |
| | | (SEQ. ID NO. 56) |
| 130 | GTGCTCGAGTCCCAGGCTACGGCACGTAG AGCATCACCATGATCCTG | |

None of these changes resulted in a significant difference in the performance of the system. Experiments 4) and 5) also resulted in a 3 and 6-base single stranded (not annealed to zip code) structure immediately upstream of the C18 spacer in the reporter oligonucleotides.

The results of these experiments indicate that the aptamer-based PDGF detection system can be assembled separating the binding and DPC functions into two separate oligonucleotides. Through the selection of appropriate zip code sequences, the detection format described in FIG. 13 self-assembled into pairs of annealed oligonucleotides which will function similarly to oligonucleotides synthesized in a single piece. The reporter and aptamer oligonucleotides may be separately assembled prior to introduction of target, or all species may be added together in almost any order. This process may be extended to the solution-phase assembly of more than one pair of annealed detection oligos, for example, to detect multiple targets. Detection of multiple targets may require using different reporter oligonucleotides which generate separately discernable signals (for example, different wavelengths of emitted light).

These results indicate that a zip-coded reporting approach can be effectively designed, for example, using aptamer-containing oligonucleotides.

While the results with the aptamer system indicate that a stable complex between binding and reporter sequences can be formed simply by annealing the zip code and anti-zip code regions, it should be noted that there are technologies to covalently and irreversibly link the two oligonucleotides together, with a high likelihood of retaining activity of the reporter reactive groups. For example, the oligonucleotides may be incubated in pairs (a binder oligonucleotide and a reactive oligonucleotide for nucleic acid-template chemistry) at a temperature at which the zip codes and anti-zip codes are mostly double stranded, but the rest of the sequences are single-stranded. Adding an intercalating, photoactivatable cross-linker such as Trioxalen, followed by UV irradiation, may irreversibly crosslink the two strands. Similarly, UV irradiation may introduce thymidine dimers between separate strands of annealed sequences. Alternately, a sequence may be introduced complementary to a short target (splice) DNA, abutting 3' and 5', which may then be ligated with DNA ligase. The splice oligonucleotide may alternately be composed of RNA, and removed after ligation with RNase H, which hydrolyzes RNA annealed to DNA. This can result in converting the two oligonucleotides into a single piece of single-stranded DNA. These methods can lead to cost-effective production of oligonucleotide reagents in detection kits against specific targets.

Relevant references for this example include Capaldi, et al., Nucleic Acid Res. 2000, 28[7], e21.; Castiglioni, et al., Appl. and Exper. Microbio. 2004, 7161-72; Fang, et al., Chem. BioChem. 2003, 4, 829-34.; Gerry, et al., J. Mol. Biol. 1999, 292, 251-62.

Example 20

Zip-Coded Architecture for DPC-based Biodetection—Antibody Binders

In another embodiment, the aptamer sequences are replaced with non-DNA binders such as antibodies. For PDGF and other protein targets, the aptamer sequences are replaced with chemically active groups, such as aldehydes, and reacted with non-DNA binder sequences such as antibodies or receptors to the protein targets (FIG. 16). The optimal design for the binder and reporter oligonucleotides may be achieved with considerations on the size and geometry of the binder and size and geometry of the binding sites of the target. A longer, or shorter spacer arms, for example, may be used to optimally span the distance between binding sites on the target and avoid steric hindrance due to the binders themselves.

Referring to FIG. 16, the zip-coded oligonucleotide designed to hybridize to the TPP reporter molecule was synthesized containing a 5'-amino group. The zip-coded oligonucleotide designed to hybridize to the AzC reporter molecule contained a 3'-amino group. Synthesis of the conjugates between the oligonucleotides and anti-PDGF-BB antibody were performed by SoluLink Biosciences (San Diego, Calif.).

The SoluLink technology for conjugation of the antibody and oligonucleotides first requires modification of the primary amino groups of the antibody with succinimidyl 2-hydrazinonicotinate acetone hydrazone) to incorporate an acetone hydrazone onto the antibody. The primary amines of the oligonucleotides are separately activated with succinimidyl 4-formylbenzoate. The two activated molecules are mixed in the desired ratio (typically 6:1) and reacted at a mildly acidic pH to form a stable hydrazone linkage. The details of this chemistry are available at www.SoluLink.com. Two conjugates were prepared: one containing the zip code to anneal to the AzC-containing reporter oligonucleotide, and the other containing the zip code to anneal to the TPP-containing reporter oligonucleotide.

The antibody-oligonucleotide conjugates received from SoluLink were further purified by gel chromatography on a 1.6×60 cm column of Superdex S-200 (Amersham Biosciences) in PBS buffer (0.01 M potassium phosphate, pH 7.4-0.138 M sodium chloride). The main antibody peak, eluting at about 0.6 times the column volume, was collected and a later eluting peak of contaminating non-conjugated oligonucleotide was discarded. The antibody conjugate was concentrated by reversed dialysis with a Pierce (Rockford, Ill.) 30 K molecular weight cut-off Slide-A-Lyzer using Pierce Concentrating Solution. The protein content was determined using the Bio-Rad Micro BCA Reagent Kit and the oligonucleotide content determined using SYBR Gold DNA binding dye (Molecular Probes (Eugene, Oreg.). The conjugates were both determined to contain an average of approximately 3 oligonucleotides per protein molecule.

Recombinant human PDGF-BB (220-BB) and mouse monoclonal anti-PDGF-BB (MAB220) were obtained from R&D Systems (Minneapolis Minn.).

Sequences used in this study included (where AzC indicates azidocoumarin and TPP indicates triphenylphosphine):

```
Name            Sequence (5'-3')

TPP reporter    TPP-(amino modifier C6)-CGAATTTATA-C18PEG-TCAGCATCGTACCTCAGC
                                        (SEQ ID NO.: 9)          (SEQ ID NO.: 58)

AzC reporter    GGACTCGAGCACCAATAC-C18 PEG-TATAAATTCG-(amino modifier C7)-AzC
                (SEQ ID NO.: 14)             (SEQ ID NO.: 10)

AzC zip code    TTGGTGCTCGAGTCCCCCCCCCCCCCCCCCCCCCC-(amino modifier C7)
                (SEQ ID NO.: 59)

TPP zip code    (amino modifier C6)-CCCCCCCCCCCCCCCCCCCCCGCTGAGGTACGATGCTGA
                                                         (SEQ ID NO.: 60)
```

In addition, the 5' amino modifier C6 was obtained from Glen Research (from Glen Research phosphoramidite 110-1906). The 3'-amino modifier C7 was obtained from Glen Research (from Glen Research CPG 20-2957). The C18 PEG was obtained from Glen Research (from Glen Research phosphoramidite 10-1918).

Assembly of Antibody-oligo Conjugates with Reporter Oligonucleotides.

The two antibody-oligo conjugates with their reporter were first assembled separately in a volume of 10 µl. Each assembly contained 0.5 µM (5 picomoles) of antibody-oligonucleotide conjugate and 0.15 µM of (15 pmoles) of complementary reporter oligonucleotide in 0.05 M Tris/HCl pH 8-0.01 M magnesium chloride. Each was incubated for at least 15 minutes at 4° C. before use in the detection reaction mixture.

Detection Reaction of Anti-PDGF-BB DPC Conjugates/Reporters with PDGF-BB

To conduct detection reaction, each reaction may contain in a volume of 50 µl: 10 µl of each conjugate assembly, prepared as described above, and variable amounts of PDGF-BB, in a buffer of 0.05 M Tris/HCl pH 8-0.01 M magnesium chloride-40% volume/volume formamide. The conjugates are present in this reaction mixture at 0.2 µM. Samples are incubated in the wells of a black 96-well microplate in a Wallac Victor Luminometer at 25° C. Fluorescence can be followed vs. time with excitation at 355 nm and emission at 460 nm.

Reactions typically may be carried out at 25° C., monitoring fluorescence generation at the wavelength optimums of the reaction product, 7-amino coumarin.

Incorporation by Reference

The entire disclosure of each of the publications and patent documents referred to herein is incorporated by reference in its entirety for all purposes to the same extent as if each individual publication or patent document were so individually denoted.

Equivalents

The invention may be embodied in other specific forms without departing form the spirit or essential characteristics thereof. The foregoing embodiments are therefore to be con-

The invention claimed is:

1. An improved in vitro method for detecting a target analyte having two or more binding sites via nucleic acid-templated chemistry, wherein the improvement comprises:
   a) detecting the target analyte by producing a hemicyanine dye having the chemical formula:

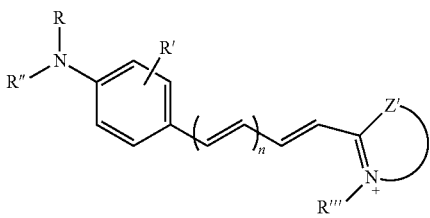

via an aldol condensation between an aldehyde having the chemical formula:

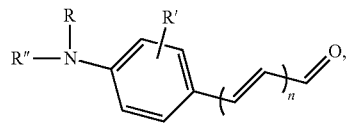

and an active hydrogen component having the chemical formula:

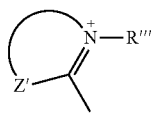

in an aqueous condition at room temperature in the presence of an organocatalyst
   wherein:
   Z' is O, S, Se, P, $NH_2$, N(alkyl), or $C(CH_3)_2$;
   n is 0, 1, or 2;
   R is H or alkyl;
   R' is phenyl, N-heterocycle, H, alkyl, —$SO_3H$, —OH, —CN, Cl, Br, —$NO_2$, —$NH_2$, —$N(alkyl)_2$, or —O-alkyl;
   R" is a linked nucleic acid;
   R''' is a linked nucleic acid; and
the organocatalyst is a secondary amine, a primary amine, or a bifunctional amine-acid catalyst, and
   b) detecting the hemicyanine dye, wherein production of the hemicyanine dye is indicative of the presence of the target analyte.

2. The method of claim 1, wherein the organocatalyst is a pyrrolidine, a piperidine, a nornicotine, or an analog thereof.

3. The method of claim 1, wherein the organocatalyst is a valine or a peptide having fewer than 3 amino acid units.

4. The method of claim 1, wherein the organocatalyst is pyrrolidine/AcOH.

5. The method of claim 1, wherein the organocatalyst is pyrrolidnylmethyl-pyrrolidine, aminomethylpyrrolidine, dimethylethane-1,2-diamine, propane-1,2-diamine, 1-(2-aminoethyl)-piperidine, or diethylethylene-1,2-diamine.

6. The method of claim 1, wherein Z' is $C(CH_3)_2$.

7. The method of claim 1, wherein the aldehyde has the following formula:

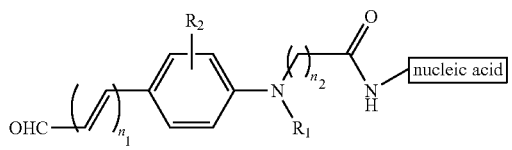

wherein:
   $n_1$ is 1 or 2;
   $n_2$ is 0 to 16;
   $R_1$ is H or alkyl; and
   $R_2$ is phenyl, N-heterocycle, H, alkyl, —$SO_3H$, OH, CN, Cl, Br, —$NO_2$, —$NH_2$, —$N(alkyl)_2$, or —O-alkyl, and the aldehyde produces the hemicyanine dye via the aldol condensation between the aldehyde and the active hydrogen component.

8. The method of claim 1, wherein the active hydrogen component has the following formula:

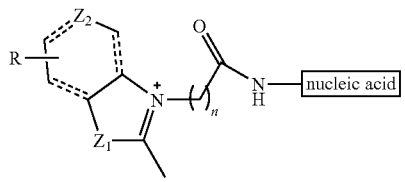

wherein:
   $Z_1$ is O, S, Se, P, $NH_2$, N(alkyl), or $C(CH_3)_2$;
   $Z_2$ is benzene or an N-heterocycle;
   n is 0 to 16; and
   R is any substituted benzyl or higher fused benzyl rings, H, alkyl, —$SO_3H$, —OH, CN, Cl, Br, —$NO_2$, —$NH_2$, —$N(alkyl)_2$, or —O-alkyl.

9. The method of claim 7, wherein the active hydrogen component has the following formula:

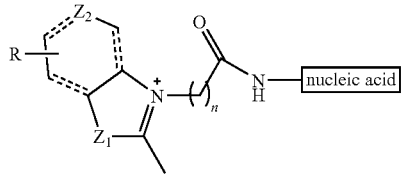

wherein:
   $Z_1$ is O, S, Se, P, $NH_2$, N(alkyl), or $C(CH_3)_2$;
   $Z_2$ is benzene or an N-heterocycle;
   n is 0 to 16; and
   R is any substituted benzyl or higher fused benzyl rings, H, alkyl, —$SO_3H$, —OH, CN, Cl, Br, —$NO_2$, —$NH_2$, —$N(alkyl)_2$, or —O-alkyl.

10. The method of claim 1, wherein the nucleic acid of R" hybridizes to a portion of the nucleic acid of R''' and the aldehyde reacts with the active hydrogen component to produce a hemicyanine dye.

11. The method of claim 1, wherein the nucleic acid of R" is hybridized to a portion of a zip-code oligonucleotide bearing a target binding moiety; and the nucleic acid of R''' is hybridized to a portion of a zip-code oligonucleotide bearing a target binding moiety.

12. The method of claim 1, wherein the target analyte is a protein.

13. The method of claim 1, wherein the target analyte is a nucleic acid.

* * * * *

SEQUENCE LISTING

<160> NUMBER OF SEQ ID NOS: 83

<210> SEQ ID NO 1
<211> LENGTH: 10
<212> TYPE: DNA
<213> ORGANISM: Artificial Sequence
<220> FEATURE:
<223> OTHER INFORMATION: Probe oligonucleotide

<400> SEQUENCE: 1
tgtaggtaac                                                          10

<210> SEQ ID NO 2
<211> LENGTH: 10
<212> TYPE: DNA
<213> ORGANISM: Artificial Sequence
<220> FEATURE:
<223> OTHER INFORMATION: Probe oligonucleotide

<400> SEQUENCE: 2
gttacctaca                                                          10

<210> SEQ ID NO 3
<211> LENGTH: 18
<212> TYPE: DNA
<213> ORGANISM: Artificial Sequence
<220> FEATURE:
<223> OTHER INFORMATION: Probe oligonucleotide

<400> SEQUENCE: 3
cttcttcatg taggtaac                                                 18

<210> SEQ ID NO 4
<211> LENGTH: 18
<212> TYPE: DNA
<213> ORGANISM: Artificial Sequence
<220> FEATURE:
<223> OTHER INFORMATION: Probe oligonucleotide

<400> SEQUENCE: 4
cttcttcagt tacctaca                                                 18

<210> SEQ ID NO 5
<211> LENGTH: 18
<212> TYPE: DNA
<213> ORGANISM: Artificial Sequence
<220> FEATURE:
<223> OTHER INFORMATION: Oligonucleotide

<400> SEQUENCE: 5
caatggatgt acttcttc                                                 18

<210> SEQ ID NO 6
<211> LENGTH: 18
<212> TYPE: DNA
<213> ORGANISM: Artificial Sequence
<220> FEATURE:
<223> OTHER INFORMATION: Oligonucleotide

<400> SEQUENCE: 6
acatccattg acttcttc                                                 18

```
<210> SEQ ID NO 7
<211> LENGTH: 18
<212> TYPE: DNA
<213> ORGANISM: Artificial Sequence
<220> FEATURE:
<223> OTHER INFORMATION: Oligonucleotide

<400> SEQUENCE: 7
caatggatgt acttcttc                                                        18

<210> SEQ ID NO 8
<211> LENGTH: 18
<212> TYPE: DNA
<213> ORGANISM: Artificial Sequence
<220> FEATURE:
<223> OTHER INFORMATION: Oligonucleotide

<400> SEQUENCE: 8
acatcctttg acttcttc                                                        18

<210> SEQ ID NO 9
<211> LENGTH: 10
<212> TYPE: DNA
<213> ORGANISM: Artificial Sequence
<220> FEATURE:
<223> OTHER INFORMATION: Oligonucleotide reporter sequence

<400> SEQUENCE: 9
cgaatttata                                                                 10

<210> SEQ ID NO 10
<211> LENGTH: 10
<212> TYPE: DNA
<213> ORGANISM: Artificial Sequence
<220> FEATURE:
<223> OTHER INFORMATION: Oligonucleotide reporter sequence

<400> SEQUENCE: 10
tataaattcg                                                                 10

<210> SEQ ID NO 11
<211> LENGTH: 34
<212> TYPE: DNA
<213> ORGANISM: Artificial Sequence
<220> FEATURE:
<223> OTHER INFORMATION: Oligonucleotide

<400> SEQUENCE: 11
caggctacgg cacgtagagc atcaccatga cctg                                      34

<210> SEQ ID NO 12
<211> LENGTH: 18
<212> TYPE: DNA
<213> ORGANISM: Artificial Sequence
<220> FEATURE:
<223> OTHER INFORMATION: oligonucleotide zip code

<400> SEQUENCE: 12
gctgccatcg atggtcag                                                        18

<210> SEQ ID NO 13
<211> LENGTH: 18
<212> TYPE: DNA
<213> ORGANISM: Artificial Sequence
<220> FEATURE:
<223> OTHER INFORMATION: Oligonucleotide anti-zip code
```

```
<400> SEQUENCE: 13
ctgaccatcg atggcagc                                            18

<210> SEQ ID NO 14
<211> LENGTH: 18
<212> TYPE: DNA
<213> ORGANISM: Artificial Sequence
<220> FEATURE:
<223> OTHER INFORMATION: Oligonucleotide anti-zip code

<400> SEQUENCE: 14
ggactcgagc accaatac                                            18

<210> SEQ ID NO 15
<211> LENGTH: 18
<212> TYPE: DNA
<213> ORGANISM: Artificial Sequence
<220> FEATURE:
<223> OTHER INFORMATION: Oligonucleotide zip code

<400> SEQUENCE: 15 gtattggt gctcgagtcc                                            18

<210> SEQ ID NO 16
<211> LENGTH: 15
<212> TYPE: DNA
<213> ORGANISM: Artificial Sequence
<220> FEATURE:
<223> OTHER INFORMATION: Oligonucleotide zip code

<400> SEQUENCE: 16
gctgccatcg atggt                                               15

<210> SEQ ID NO 17
<211> LENGTH: 15
<212> TYPE: DNA
<213> ORGANISM: Artificial Sequence
<220> FEATURE:
<223> OTHER INFORMATION: Oligonucleotide anti-zip code

<400> SEQUENCE: 17
accatcgatg gcagc                                               15

<210> SEQ ID NO 18
<211> LENGTH: 13
<212> TYPE: DNA
<213> ORGANISM: Artificial Sequence
<220> FEATURE:
<223> OTHER INFORMATION: Oligonucleotide zip code

<400> SEQUENCE: 18
ttggtgctcg agt                                                 13

<210> SEQ ID NO 19
<211> LENGTH: 31
<212> TYPE: DNA
<213> ORGANISM: Artificial Sequence
<220> FEATURE:
<223> OTHER INFORMATION: Oligo1 oligonucleotide

<400> SEQUENCE: 19
gtggtagttg gagctggtgg cgtaggcaag a                             31

<210> SEQ ID NO 20
<211> LENGTH: 15
```

```
<212> TYPE: DNA
<213> ORGANISM: Artificial Sequence
<220> FEATURE:
<223> OTHER INFORMATION: Oligo2 oligonucleotide

<400> SEQUENCE: 20
agctccaact accac                                                    15

<210> SEQ ID NO 21
<211> LENGTH: 15
<212> TYPE: DNA
<213> ORGANISM: Artificial Sequence
<220> FEATURE:
<223> OTHER INFORMATION: Oligo4 oligonucleotide

<400> SEQUENCE: 21
gtggtagttg gagct                                                    15

<210> SEQ ID NO 22
<211> LENGTH: 15
<212> TYPE: DNA
<213> ORGANISM: Artificial Sequence
<220> FEATURE:
<223> OTHER INFORMATION: Oligo5 oligonucleotide

<400> SEQUENCE: 22
tcttgcctac gccac                                                    15

<210> SEQ ID NO 23
<211> LENGTH: 15
<212> TYPE: DNA
<213> ORGANISM: Artificial Sequence
<220> FEATURE:
<223> OTHER INFORMATION: Oligo6 oligonucleotide

<400> SEQUENCE: 23
agatcccact agcac                                                    15

<210> SEQ ID NO 24
<211> LENGTH: 18
<212> TYPE: DNA
<213> ORGANISM: Artificial Sequence
<220> FEATURE:
<223> OTHER INFORMATION: Oligo 26 oligonucleotide

<400> SEQUENCE: 24
cttcggccca gatatcgt                                                 18

<210> SEQ ID NO 25
<211> LENGTH: 18
<212> TYPE: DNA
<213> ORGANISM: Artificial Sequence
<220> FEATURE:
<223> OTHER INFORMATION: Oligo 27 oligonucleotide

<400> SEQUENCE: 25
ctacagctac gatatctg                                                 18

<210> SEQ ID NO 26
<211> LENGTH: 18
<212> TYPE: DNA
<213> ORGANISM: Artificial Sequence
<220> FEATURE:
<223> OTHER INFORMATION: Oligo 28 oligonucleotide

<400> SEQUENCE: 26
ctacagctgt gatatcat                                                 18
```

<210> SEQ ID NO 27
<211> LENGTH: 20
<212> TYPE: DNA
<213> ORGANISM: Artificial Sequence
<220> FEATURE:
<223> OTHER INFORMATION: AT-rich oligonucleotide

<400> SEQUENCE: 27
tttttttttt tttaattaaa                                          20

<210> SEQ ID NO 28
<211> LENGTH: 55
<212> TYPE: DNA
<213> ORGANISM: Artificial Sequence
<220> FEATURE:
<223> OTHER INFORMATION: Oligo 201 oligonucleotide

<400> SEQUENCE: 28
caggctacgg cacgtagagc atcaccatga tcctgccccc ccccatatt taagc     55

<210> SEQ ID NO 29
<211> LENGTH: 55
<212> TYPE: DNA
<213> ORGANISM: Artificial Sequence
<220> FEATURE:
<223> OTHER INFORMATION: Oligo 202 oligonucleotide

<400> SEQUENCE: 29
gcttaaatat cccccccccc caggctacgg cacgtagagc atcaccatga tcctg     55

<210> SEQ ID NO 30
<211> LENGTH: 57
<212> TYPE: DNA
<213> ORGANISM: Artificial Sequence
<220> FEATURE:
<223> OTHER INFORMATION: Oligo 203 oligonucleotide

<400> SEQUENCE: 30
gtgggaatgg tgcccccccc cccaggctac ggcacgtaga gcatcaccat gatcctg   57

<210> SEQ ID NO 31
<211> LENGTH: 30
<212> TYPE: DNA
<213> ORGANISM: Artificial Sequence
<220> FEATURE:
<223> OTHER INFORMATION: Oligo 204 oligonucleotide

<400> SEQUENCE: 31
gtggtagttg gagtcgtggc gtaggcaaga                                30

<210> SEQ ID NO 32
<211> LENGTH: 34
<212> TYPE: DNA
<213> ORGANISM: Artificial Sequence
<220> FEATURE:
<223> OTHER INFORMATION: Oligo 205 oligonucleotide

<400> SEQUENCE: 32
gtggtagttg gagtcacacg tggcgtaggc aaga                           34

<210> SEQ ID NO 33
<211> LENGTH: 40
<212> TYPE: DNA
<213> ORGANISM: Artificial Sequence
<220> FEATURE:
<223> OTHER INFORMATION: Oligo 206 oligonucleotide

```
<400> SEQUENCE: 33
gtggtagttg gagctcacac cacacgtggc gtaggcaaga                           40

<210> SEQ ID NO 34
<211> LENGTH: 46
<212> TYPE: DNA
<213> ORGANISM: Artificial Sequence
<220> FEATURE:
<223> OTHER INFORMATION: Oligo 207 oligonucleotide

<400> SEQUENCE: 34
gtggtagttg gagtcacaca caccacacac agtggcgtag gcaaga                   46

<210> SEQ ID NO 35
<211> LENGTH: 68
<212> TYPE: DNA
<213> ORGANISM: Artificial Sequence
<220> FEATURE:
<223> OTHER INFORMATION: Oligo 208 oligonucleotide

<400> SEQUENCE: 35
gtggtagttg gagctcacac cacaccaacc acaccacacc acacacacca cacgtggcgt    60
aggcaaga                                                             68

<210> SEQ ID NO 36
<211> LENGTH: 20
<212> TYPE: DNA
<213> ORGANISM: Artificial Sequence
<220> FEATURE:
<223> OTHER INFORMATION: Oligo 209 oligonucleotide

<400> SEQUENCE: 36
gtgtggtgtg gtgtggtgtg                                                20

<210> SEQ ID NO 37
<211> LENGTH: 30
<212> TYPE: DNA
<213> ORGANISM: Artificial Sequence
<220> FEATURE:
<223> OTHER INFORMATION: Oligo 210 oligonucleotide

<400> SEQUENCE: 37
gtggcgtagg caagagtggt agttggagct                                     30

<210> SEQ ID NO 38
<211> LENGTH: 12
<212> TYPE: DNA
<213> ORGANISM: Artificial Sequence
<220> FEATURE:
<223> OTHER INFORMATION: Oligo 211 oligonucleotide

<400> SEQUENCE: 38
gtgggaatgg tg                                                        12

<210> SEQ ID NO 39
<211> LENGTH: 15
<212> TYPE: DNA
<213> ORGANISM: Artificial Sequence
<220> FEATURE:
<223> OTHER INFORMATION: Oligo 212 oligonucleotide

<400> SEQUENCE: 39
agatcccact agcac                                                     15
```

```
<210> SEQ ID NO 40
<211> LENGTH: 15
<212> TYPE: DNA
<213> ORGANISM: Artificial Sequence
<220> FEATURE:
<223> OTHER INFORMATION: Oligo 213 oligonucleotide

<400> SEQUENCE: 40
agctccaact accac                                                    15

<210> SEQ ID NO 41
<211> LENGTH: 15
<212> TYPE: DNA
<213> ORGANISM: Artificial Sequence
<220> FEATURE:
<223> OTHER INFORMATION: Oligo 214 oligonucleotide

<400> SEQUENCE: 41
tcttgcctac gccac                                                    15

<210> SEQ ID NO 42
<211> LENGTH: 35
<212> TYPE: DNA
<213> ORGANISM: Artificial Sequence
<220> FEATURE:
<223> OTHER INFORMATION: Oligo 215 oligonucleotide

<400> SEQUENCE: 42
caggctacgg cacgtagagc atcaccatga tcctg                              35

<210> SEQ ID NO 43
<211> LENGTH: 28
<212> TYPE: DNA
<213> ORGANISM: Artificial Sequence
<220> FEATURE:
<223> OTHER INFORMATION: Oligo 106 oligonucleotide
<220> FEATURE:
<221> NAME/KEY: misc_feature
<222> LOCATION: (18)..(19)
<223> OTHER INFORMATION: C18 PEG

<400> SEQUENCE: 43
ggactcgagc accaatacta taaattcg                                      28

<210> SEQ ID NO 44
<211> LENGTH: 28
<212> TYPE: DNA
<213> ORGANISM: Artificial Sequence
<220> FEATURE:
<223> OTHER INFORMATION: Oligo 109 oligonucleotide
<220> FEATURE:
<221> NAME/KEY: misc_feature
<222> LOCATION: (10)..(11)
<223> OTHER INFORMATION: C18 PEG

<400> SEQUENCE: 44
cgaatttata ctgaccatcg atggcagc                                      28

<210> SEQ ID NO 45
<211> LENGTH: 53
<212> TYPE: DNA
<213> ORGANISM: Artificial Sequence
<220> FEATURE:
<223> OTHER INFORMATION: Oligo 112 oligonucleotide
<220> FEATURE:
<221> NAME/KEY: misc_feature
<222> LOCATION: (35)..(36)
<223> OTHER INFORMATION: C18 PEG

<400> SEQUENCE: 45
```
caggctacgg cacgtagagc atcaccatga tcctggctgc catcgatggt cag            53

<210> SEQ ID NO 46
<211> LENGTH: 53
<212> TYPE: DNA
<213> ORGANISM: Artificial Sequence
<220> FEATURE:
<223> OTHER INFORMATION: Oligo 113 oligonucleotide
<220> FEATURE:
<221> NAME/KEY: misc_feature
<222> LOCATION: (18)..(19)
<223> OTHER INFORMATION: C18 PEG

<400> SEQUENCE: 46
gtattggtgc tcgagtccca ggctacggca cgtagagcat caccatgatc ctg            53

<210> SEQ ID NO 47
<211> LENGTH: 53
<212> TYPE: DNA
<213> ORGANISM: Artificial Sequence
<220> FEATURE:
<223> OTHER INFORMATION: Oligo 119 oligonucleotide

<400> SEQUENCE: 47
gtattggtgc tcgagtccca ggctacggca cgtagagcat caccatgatc ctg            53

<210> SEQ ID NO 48
<211> LENGTH: 63
<212> TYPE: DNA
<213> ORGANISM: Artificial Sequence
<220> FEATURE:
<223> OTHER INFORMATION: Oligo 120 oligonucleotide

<400> SEQUENCE: 48
gtattggtgc tcgagtcccc ccccccccca ggctacggca cgtagagcat caccatgatc    60
ctg                                                                   63

<210> SEQ ID NO 49
<211> LENGTH: 73
<212> TYPE: DNA
<213> ORGANISM: Artificial Sequence
<220> FEATURE:
<223> OTHER INFORMATION: Oligo 121 oligonucleotide

<400> SEQUENCE: 49
gtattggtgc tcgagtcccc cccccccccc ccccccccca ggctacggca cgtagagcat    60
caccatgatc ctg                                                        73

<210> SEQ ID NO 50
<211> LENGTH: 53
<212> TYPE: DNA
<213> ORGANISM: Artificial Sequence
<220> FEATURE:
<223> OTHER INFORMATION: Oligo 122 oligonucleotide

<400> SEQUENCE: 50
caggctacgg cacgtagagc atcaccatga tcctggctgc catcgatggt cag            53

<210> SEQ ID NO 51
<211> LENGTH: 63
<212> TYPE: DNA
<213> ORGANISM: Artificial Sequence
<220> FEATURE:
<223> OTHER INFORMATION: Oligo 123 oligonucleotide

<400> SEQUENCE: 51

```
caggctacgg cacgtagagc atcaccatga tcctgccccc ccccgctgc catcgatggt    60 cag                                                                 63

<210> SEQ ID NO 52
<211> LENGTH: 73
<212> TYPE: DNA
<213> ORGANISM: Artificial Sequence
<220> FEATURE:
<223> OTHER INFORMATION: Oligo 124 oligonucleotide

<400> SEQUENCE: 52
caggctacgg cacgtagagc atcaccatga tcctgccccc cccccccccc ccccgctgc    60 catcgatggt cag                                                      73

<210> SEQ ID NO 53
<211> LENGTH: 50
<212> TYPE: DNA
<213> ORGANISM: Artificial Sequence
<220> FEATURE:
<223> OTHER INFORMATION: Oligo 127 oligonucleotide

<400> SEQUENCE: 53
caggctacgg cacgtagagc atcaccatga tcctggctgc catcgatggt              50

<210> SEQ ID NO 54
<211> LENGTH: 47
<212> TYPE: DNA
<213> ORGANISM: Artificial Sequence
<220> FEATURE:
<223> OTHER INFORMATION: Oligo 128 oligonucleotide

<400> SEQUENCE: 54
caggctacgg cacgtagagc atcaccatga tcctggctgc catcgat                 47

<210> SEQ ID NO 55
<211> LENGTH: 50
<212> TYPE: DNA
<213> ORGANISM: Artificial Sequence
<220> FEATURE:
<223> OTHER INFORMATION: Oligo 129 oligonucleotide

<400> SEQUENCE: 55
ttggtgctcg agtcccaggc tacggcacgt agagcatcac catgatcctg              50

<210> SEQ ID NO 56
<211> LENGTH: 47
<212> TYPE: DNA
<213> ORGANISM: Artificial Sequence
<220> FEATURE:
<223> OTHER INFORMATION: Oligo 130 oligonucleotide

<400> SEQUENCE: 56
gtgctcgagt cccaggctac ggcacgtaga gcatcaccat gatcctg                 47

<210> SEQ ID NO 57
<211> LENGTH: 18
<212> TYPE: DNA
<213> ORGANISM: Artificial Sequence
<220> FEATURE:
<223> OTHER INFORMATION: Oligonucleotide zip code

<400> SEQUENCE: 57
gctgaggtac gatgctga                                                 18
```

```
<210> SEQ ID NO 58
<211> LENGTH: 18
<212> TYPE: DNA
<213> ORGANISM: Artificial Sequence
<220> FEATURE:
<223> OTHER INFORMATION: Oligonucleotide anti-zip code

<400> SEQUENCE: 58
tcagcatcgt acctcagc                                                    18

<210> SEQ ID NO 59
<211> LENGTH: 35
<212> TYPE: DNA
<213> ORGANISM: Artificial Sequence
<220> FEATURE:
<223> OTHER INFORMATION: Oligonucleotide

<400> SEQUENCE: 59
ttggtgctcg agtcccccccc ccccccccccc ccccc                               35

<210> SEQ ID NO 60
<211> LENGTH: 38
<212> TYPE: DNA
<213> ORGANISM: Artificial Sequence
<220> FEATURE:
<223> OTHER INFORMATION: Oligonucleotide

<400> SEQUENCE: 60
cccccccccc cccccccccc gctgaggtac gatgctga                              38

<210> SEQ ID NO 61
<211> LENGTH: 15
<212> TYPE: DNA
<213> ORGANISM: Artificial Sequence
<220> FEATURE:
<223> OTHER INFORMATION: Oligo EDC1 oligonucleotide

<400> SEQUENCE: 61
gtggtagttg gagct                                                       15

<210> SEQ ID NO 62
<211> LENGTH: 15
<212> TYPE: DNA
<213> ORGANISM: Artificial Sequence
<220> FEATURE:
<223> OTHER INFORMATION: Oligo EDC2 oligonucleotide

<400> SEQUENCE: 62
agctccaact accac                                                       15

<210> SEQ ID NO 63
<211> LENGTH: 15
<212> TYPE: DNA
<213> ORGANISM: Artificial Sequence
<220> FEATURE:
<223> OTHER INFORMATION: Oligo EDC3 oligonucleotide

<400> SEQUENCE: 63
agatcccact agcac                                                       15

<210> SEQ ID NO 64
<211> LENGTH: 35
<212> TYPE: DNA
<213> ORGANISM: Artificial Sequence
<220> FEATURE:
<223> OTHER INFORMATION: Aptamer oligonucleotide

<400> SEQUENCE: 64
```

-continued

```
caggctacgg cacgtagagc atcaccatga tcctg                              35

<210> SEQ ID NO 65
<211> LENGTH: 35
<212> TYPE: DNA
<213> ORGANISM: Artificial Sequence
<220> FEATURE:
<223> OTHER INFORMATION: Aptamer oligonucleotide

<400> SEQUENCE: 65
caggctacgg cacgtagagc atcaccatga tcctg                              35

<210> SEQ ID NO 66
<211> LENGTH: 35
<212> TYPE: DNA
<213> ORGANISM: Artificial
<220> FEATURE:
<223> OTHER INFORMATION: Zip2

<400> SEQUENCE: 66
ttggtgctcg agtcccccccc cccccccccc ccccc                             35

<210> SEQ ID NO 67
<211> LENGTH: 35
<212> TYPE: DNA
<213> ORGANISM: Artificial
<220> FEATURE:
<223> OTHER INFORMATION: Zip3

<400> SEQUENCE: 67
cccccccccc cccccccccc gctgccatcg atggt                              35

<210> SEQ ID NO 68
<211> LENGTH: 35
<212> TYPE: DNA
<213> ORGANISM: Artificial
<220> FEATURE:
<223> OTHER INFORMATION: Zip5

<400> SEQUENCE: 68
cccccccccc ccccccccgt gccatccata gtcag                              35

<210> SEQ ID NO 69
<211> LENGTH: 28
<212> TYPE: DNA
<213> ORGANISM: Artificial
<220> FEATURE:
<223> OTHER INFORMATION: Antizip2 reporter 1

<400> SEQUENCE: 69
ggactcgagc accaatacta taaattcg                                      28

<210> SEQ ID NO 70
<211> LENGTH: 28
<212> TYPE: DNA
<213> ORGANISM: Artificial
<220> FEATURE:
<223> OTHER INFORMATION: Antizip3 reporter

<400> SEQUENCE: 70
cgaatttata ctgaccatcg atggcagc                                      28

<210> SEQ ID NO 71
<211> LENGTH: 28
<212> TYPE: DNA
<213> ORGANISM: Artificial
```

```
<220> FEATURE:
<223> OTHER INFORMATION: Antizip5 reporter mismatch

<400> SEQUENCE: 71
ccaattaata ctgactatgg atggcacg                                            28

<210> SEQ ID NO 72
<211> LENGTH: 29
<212> TYPE: DNA
<213> ORGANISM: Artificial
<220> FEATURE:
<223> OTHER INFORMATION: Chemically synthesized, Antizip5 reporter
<220> FEATURE:
<221> NAME/KEY: misc_feature
<222> LOCATION: (11)..(11)
<223> OTHER INFORMATION: n is a, c, g, t or u

<400> SEQUENCE: 72
cgaatttata nctgactatg gatggcacg                                           29

<210> SEQ ID NO 73
<211> LENGTH: 32
<212> TYPE: DNA
<213> ORGANISM: Artificial
<220> FEATURE:
<223> OTHER INFORMATION: Chemically synthesized, Antizip2 report2
<220> FEATURE:
<221> NAME/KEY: misc_feature
<222> LOCATION: (19)..(19)
<223> OTHER INFORMATION: n is a, c, g, t or u

<400> SEQUENCE: 73
ggactcgagc accaatacnt ataaattcgc cc                                       32

<210> SEQ ID NO 74
<211> LENGTH: 30
<212> TYPE: DNA
<213> ORGANISM: Artificial
<220> FEATURE:
<223> OTHER INFORMATION: Chemically synthesized

<400> SEQUENCE: 74
gtggtagttg gagctggtgg cgtaggcaag                                          30

<210> SEQ ID NO 75
<211> LENGTH: 15
<212> TYPE: DNA
<213> ORGANISM: Artificial
<220> FEATURE:
<223> OTHER INFORMATION: Chemically synthesized, EDC2

<400> SEQUENCE: 75
agctccaact accac                                                          15

<210> SEQ ID NO 76
<211> LENGTH: 15
<212> TYPE: DNA
<213> ORGANISM: Artificial
<220> FEATURE:
<223> OTHER INFORMATION: Chemically  synthesized, EDC3

<400> SEQUENCE: 76
agatcccact agcac                                                          15

<210> SEQ ID NO 77
<211> LENGTH: 15
<212> TYPE: DNA
<213> ORGANISM: Artificial
```

-continued

```
<220> FEATURE:
<223> OTHER INFORMATION: Chemically synthesized, EDC4

<400> SEQUENCE: 77
gtggtagttg gagct                                                      15

<210> SEQ ID NO 78
<211> LENGTH: 15
<212> TYPE: DNA
<213> ORGANISM: Artificial
<220> FEATURE:
<223> OTHER INFORMATION: Chemically synthesized, EDC5

<400> SEQUENCE: 78
tcttgcctac gccac                                                      15

<210> SEQ ID NO 79
<211> LENGTH: 15
<212> TYPE: DNA
<213> ORGANISM: Artificial
<220> FEATURE:
<223> OTHER INFORMATION: Chemically synthesized, EDC7

<400> SEQUENCE: 79
acccttgaac acgtc                                                      15

<210> SEQ ID NO 80
<211> LENGTH: 15
<212> TYPE: DNA
<213> ORGANISM: Artificial
<220> FEATURE:
<223> OTHER INFORMATION: Chemically synthesized, EDC8

<400> SEQUENCE: 80
tctccgttgc cgctc                                                      15

<210> SEQ ID NO 81
<211> LENGTH: 31
<212> TYPE: DNA
<213> ORGANISM: Artificial
<220> FEATURE:
<223> OTHER INFORMATION: Chemically synthesized, EDC10

<400> SEQUENCE: 81
gtggtagttg gagctggagc ggcaacggag a                                    31

<210> SEQ ID NO 82
<211> LENGTH: 31
<212> TYPE: DNA
<213> ORGANISM: Artificial
<220> FEATURE:
<223> OTHER INFORMATION: Chemically synthesized, EDC11

<400> SEQUENCE: 82
gacgtgttca agggtggtgg cgtaggcaag a                                    31

<210> SEQ ID NO 83
<211> LENGTH: 31
<212> TYPE: DNA
<213> ORGANISM: Artificial
<220> FEATURE:
<223> OTHER INFORMATION: Chemically synthesized, EDC12

<400> SEQUENCE: 83
gacgtgttca agggtggagc ggcaacggag a                                    31
```